US010152569B2

(12) United States Patent
Yin et al.

(10) Patent No.: US 10,152,569 B2
(45) Date of Patent: Dec. 11, 2018

(54) ALGORITHMS FOR SEQUENCE DETERMINATIONS

(71) Applicant: Gen-Probe Incorporated, San Diego, CA (US)

(72) Inventors: Tongjia Yin, San Diego, CA (US); Steve Brentano, San Diego, CA (US); Jennifer Bungo, San Diego, CA (US); Xianqun Wang, San Diego, CA (US); Michael Hadjisavas, San Diego, CA (US)

(73) Assignee: GEN-PROBE INCORPORATED, San Diego, CA (US)

(*) Notice: Subject to any disclaimer, the term of this patent is extended or adjusted under 35 U.S.C. 154(b) by 164 days.

(21) Appl. No.: 14/346,954

(22) PCT Filed: Sep. 26, 2012

(86) PCT No.: PCT/US2012/057237
§ 371 (c)(1),
(2) Date: Mar. 24, 2014

(87) PCT Pub. No.: WO2013/049135
PCT Pub. Date: Apr. 4, 2013

(65) Prior Publication Data
US 2014/0235461 A1    Aug. 21, 2014

Related U.S. Application Data

(60) Provisional application No. 61/539,440, filed on Sep. 26, 2011.

(51) Int. Cl.
G06F 19/22    (2011.01)

(52) U.S. Cl.
CPC .................................... *G06F 19/22* (2013.01)

(58) Field of Classification Search
None
See application file for complete search history.

(56) References Cited

U.S. PATENT DOCUMENTS

2003/0200033 A1    10/2003    Segal et al.
2010/0169026 A1    7/2010    Sorenson et al.

OTHER PUBLICATIONS

Jeck et al. Bioinformatics vol. 23 No. 21 pp. 2942-2944.*
(Continued)

*Primary Examiner* — Joseph Woitach
(74) *Attorney, Agent, or Firm* — Alston & Bird LLP

(57) ABSTRACT

The invention provides methods of determining a consensus sequence from multiple raw sequencing reads of a nucleic acid target. The nucleic acid target includes an anchor segment of known sequence and an adjacent segment of unknown sequence. The anchor segment provides a means to assess the quality of a raw target sequencing read. Raw target sequencing reads meeting or exceeding a threshold are assigned to an accepted class. The consensus sequence of the adjacent segment can be determined from raw target sequencing reads in the accepted class. Successive polling steps determine successive consensus nucleobases in a nascent sequence of the adjacent segment. Raw target sequencing reads can be removed or reintroduced from the accepted class depending on their correspondence to the most recently determined consensus nucleobase and/or the nascent sequence.

34 Claims, 8 Drawing Sheets

Specification includes a Sequence Listing.

(56) References Cited

OTHER PUBLICATIONS

Jeck et al., "Extending assembly of short DNA sequences to handle error," *Bioinformatics*, 23(21): 2942-2944, (2007).
Bryant Jr. et al., "QSRA â a quality-value guided de novo short read assembler," *BMC Bioinformatics*, Biomed Central, 10(1): 69, (2009).
Dohm et al., "SHARCGS, a fast and highly accurate short-read assembly algorithm for de novo genomic sequencing," *Genome Research*, Cold Spring Harbor Laboratory Press, 17(1): 1697-1706, (2007).

* cited by examiner

A
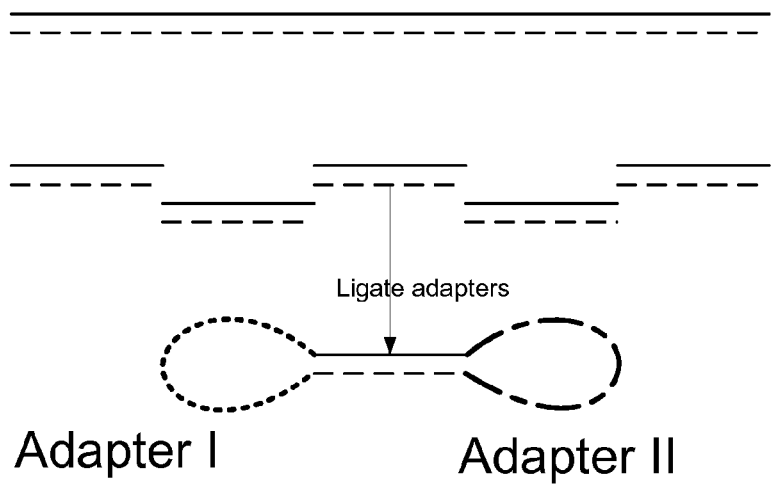
B
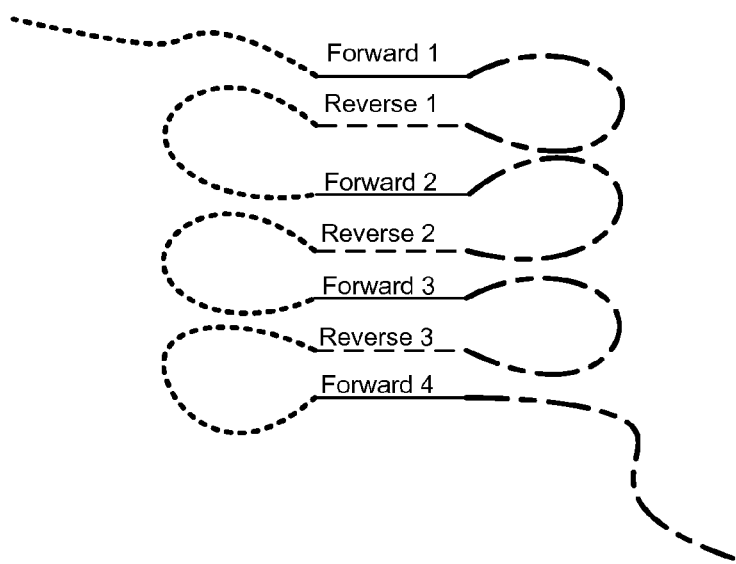
FIGS. 3A, B

C
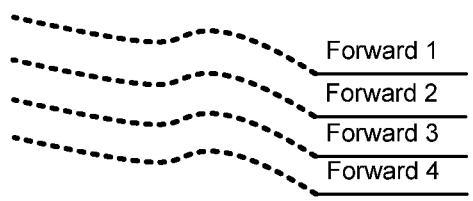
D
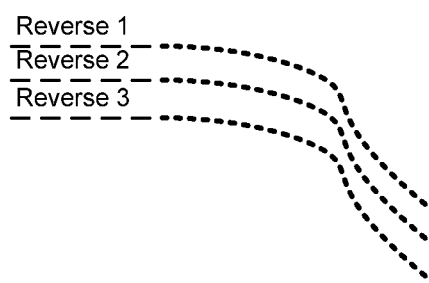
E
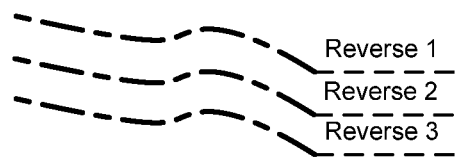
F
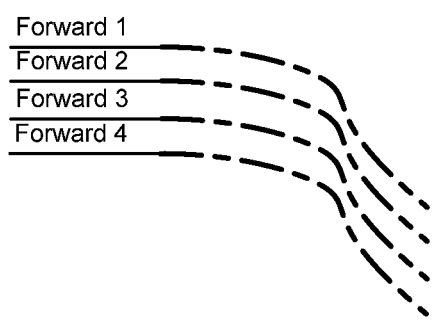
*FIGS. 3C-F*

ALGORITHMS FOR SEQUENCE DETERMINATIONS

CROSS-REFERENCE TO RELATED APPLICATIONS

The present applications is a US national stage of PCT/US2012/057237 filed Sep. 26, 2012, which claims the benefit of claims the benefit of 61/539,440 filed Sep. 26, 2011 incorporated by reference in its entirety for all purposes.

REFERENCE TO A "SEQUENCE LISTING"

The sequence listing in file 424273SEQLIST.TXT was created Sep. 7, 2012 and is 34,407 bytes. This sequence listing is hereby incorporated by reference.

BACKGROUND

Over the past decade, DNA sequencing throughput has increased over 50-fold. Advances in DNA sequencing have revolutionized the fields of cellular and molecular biology. High-throughput sequencing platforms include the 454 FLX™ or 454 TITANIUM™ (Roche), the SOLEXA™ Genome Analyzer (Illumina), the HELISCOPE™ Single Molecule Sequencer (Helicos Biosciences), the SOLID™ DNA Sequencer (Life Technologies/Applied Biosystems) instruments), SMRT™ technology developed by Pacific Biosystems, as well as other platforms still under development by companies such as Intelligent Biosystems.

Although such sequencing platforms generate vast amounts of sequencing data including multiple reads of the same target sequence, difficulties remain in deducing correct sequences present in a sample due to errors introduced by the high-throughput sequencing methods. With the high error rate, it is difficult to identify the majority species consistently and reliably. It is even more difficult to identify the minority species that differ little from the majority species and to determine their prevalence. Most sequence alignment-based methods alone cannot overcome high frequencies of error.

SUMMARY OF THE CLAIMED INVENTION

The invention provides computer-implemented methods of developing a consensus sequence from a plurality of sequencing reads of a nucleic acid target. Such methods involve (a) receiving a population of raw target sequencing reads of a nucleic acid target comprising an anchor segment and an adjacent segment; the anchor segment being of known sequence and the adjacent segment being of unknown sequence; and at least some of the raw target sequencing reads containing sequencing errors; (b) evaluating the accuracy of sequencing of the anchor segment in different raw target sequencing reads by comparing raw target sequencing reads of the anchor segment with the known sequence of the anchor segment; (c) assigning a subset of the raw target sequencing reads into an accepted class based on reaching at least a threshold level of accuracy of the sequencing of the anchor segment; (d) polling nucleobases at a position equidistant to the anchor segment sequence in raw target sequencing reads in the accepted class to determine a consensus nucleobase, which consensus nucleobase is assigned as the first nucleobase of a nascent sequence of the adjacent segment; (e) assigning raw target sequencing reads having the consensus nucleobase determined in the prior polling step to remain in an accepted class and assigning raw target sequencing reads lacking the consensus nucleobase determined in the prior polling step to the rejected class; (f) optionally reassigning a raw target sequencing read from the rejected class to the accepted class by scoring similarity of the raw target sequencing read to the nascent sequence and reintroducing the raw target sequencing read if the sequence similarity reaches at least a threshold level of similarity; and (g) repeating steps (d), (e) and optionally (f), except that a repetition polls a position adjacent the position poled in the previous polling step for raw target sequencing reads having the consensus nucleobase polled in the previous step or in the case of a raw target sequencing read reassigned from the rejected class to the accepted class and not polled in the previous polling step or if polled not having the consensus nucleobase in the previous polling step, the polling polls a position adjacent the position aligned with the last nucleobase of the nascent sequence to determine a consensus nucleobase, and the consensus nucleobases determined in successive repetitions are assigned as successive nucleobases in the nascent sequence of the adjacent segment.

In some methods, step (f) is performed at least once. In some methods, step (g) is performed at least 20 times and step (f) at least 5 times. In some methods, step (g) is performed at least 100 times and step (f) at least 20 times. In some methods, the threshold for step (f) is at least 80% identity between the raw target sequencing read and nascent sequence when maximally aligned and a match between the last assigned nucleobase of the nascent sequence and corresponding nucleobase of the raw targeting sequencing read. In some methods, the threshold level of accuracy of the sequencing the anchor segment is based on percentage of sequence identity and/or location of matched nucleobases between a raw target sequencing read and the known anchor segment. In some methods the threshold level of accuracy requires a raw target sequencing read to have the correct nucleobase corresponding to the nucleobase of the anchor segment immediately adjacent the adjacent segment. In some methods, the nucleic acid target includes a nucleobase variation at a position and when step (g) polls the position it determines two consensus nucleobases for the position, wherein the nascent sequence is branched into two nascent sequences differing between the two consensus nucleobases and the consensus nucleobase determined in further repetitions of step (g) is assigned to both nascent sequences. In some methods, the nucleic acid target comprises first and second anchor segments at opposing ends of the nucleic acid target and the raw target sequencing reads include a first group of raw target sequencing reads of the first anchor segment and an adjacent segment and a second group of raw target sequencing reads of the second anchor segment and an adjacent segment; the first and second groups being raw sequencing reads of opposing strands of the nucleic acid target and the method is performed on the first and second groups of raw target sequencing reads to determine consensus sequences of opposing strands of the target nucleic acid.

In some methods, the raw sequencing reads comprise raw sequencing reads of first and second nucleic acid targets, the first nucleic acid target comprising the anchor segment linked to a first adjacent segment and the second nucleic acid target comprising the anchor segment linked to a second adjacent segment. In some methods, the first and second adjacent segments are overlapping segments. In some methods, the first and second adjacent segments are fragments of the same contiguous polynucleotide. In some methods, the first and second adjacent segments are nonoverlapping segments. In some methods, the raw sequencing reads comprising raw sequence reads of a plurality of nucleic acid targets, the different nucleic acid targets comprising the anchor segment linked to different adjacent segments; the different adjacent segments including overlapping and non-overlapping segments. In some methods, a strand of the anchor segment is a primer or primer binding site incorporated into the nucleic acid target. In some methods, a strand of the anchor segment has 4-120 nucleobases, or 8-30 nucleobases. In some methods, the anchor segment is an oligonucleotide ligated to a nucleic acid fragment to be sequenced. In some methods, the anchor segment and adjacent segment are contiguous segments in a nucleic acid from nature. In some methods, the anchor segment is a repeat sequence.

Some methods also involve outputting the sequence of at least part of the adjacent segment. Some methods also involve synthesizing a nucleic acid sequence having a sequence comprising at least part of the adjacent segment. Some methods also include experimentally determining the population of raw target sequencing reads of the target nucleic acid.

In some methods, the population of raw target sequencing reads is determined by a sequencing-by-synthesis method. In some methods, the sequencing method is single-molecule sequencing. In some methods, the sequencing method is single-molecule real time sequencing. In some methods, the nucleic acid target is in the form of a circular template. In some methods, the nucleic acid target is a homogeneous population of the same nucleic acid molecule.

In some methods the nucleic acid target is a heterogeneous population of variant nucleic acid molecules. In some methods, the variant nucleic acid molecules are variant nucleic acid molecules of the same virus. In some method, the virus is HIV or HCV. In some methods, the variants are allelic variants. In some methods, the nucleic acid target is a circular DNA molecule and the raw target sequencing reads comprise alternating reads of the anchor segment and the adjacent segment. In some methods, the reads of the adjacent segment comprise reads of alternating strands of the adjacent segment. In some methods, the circular DNA molecule is formed by ligating first and second hairpin anchor segments to the adjacent segment. In some methods, the first and second hairpin anchor segments are the same. In some methods, the first and second hairpin anchors are different and the raw target sequencing reads comprise alternating reads of the first and second hairpin anchor segments.

Some methods also involve designating a segment of the nascent sequence of the adjacent segment as a new anchor segment and repeating the method to determine a consensus sequence of an adjacent segment adjacent the new anchor segment.

The invention further provides a computer program product for analyzing a nucleic acid target, comprising (a) code for receiving a population of raw target sequencing reads of a nucleic acid target comprising an anchor segment and an adjacent segment; the anchor segment being of known sequence and the adjacent segment being of unknown sequence; and at least some of the raw target sequencing reads containing sequencing errors; (b) code for evaluating the accuracy of sequencing of the anchor segment in different raw target sequencing reads by comparing the raw target sequencing reads of the anchor segment with the known sequence of the anchor segment; (c) code for assigning a subset of the raw target sequencing reads into an accepted class based on reaching at least a threshold level of accuracy of the sequencing of the anchor segment; (d) code for polling nucleobases at a position equidistant to the anchor segment sequence in raw target sequencing reads in the accepted class to determine a consensus nucleobase, which consensus nucleobase is assigned as the first nucleobase of a nascent sequence of the adjacent segment; (e) code for assigning raw target sequencing reads having the consensus nucleobase determined in the prior polling step to remain in an accepted class and assigning raw target sequencing reads lacking the consensus nucleobase determined in the prior polling step to the rejected class; (f) code for optionally reassigning a raw target sequencing read from the rejected class to the accepted class by scoring similarity of the raw target sequencing read to the nascent sequence and reintroducing the raw target sequencing read if the sequence similarity reaches at least a threshold level of similarity; and (g) code for repeating steps coded in (d), (e) and optionally (f), except that a repetition polls a position adjacent the position poled in the previous polling step for raw target sequencing reads having the consensus nucleobase polled in the previous step or in the case of a raw target sequencing read reassigned from the rejected class to the accepted class and not polled in the previous polling step or if polled not having the consensus nucleobase in the previous polling step, the polling polls a position adjacent the position aligned with the last nucleobase of the nascent sequence to determine a consensus nucleobase, and the consensus nucleobases determined in successive repetitions are assigned as successive nucleobases in the nascent sequence of the adjacent segment.

In some computer program products, the threshold in (f) is at least 80% identity between the raw target sequencing read and nascent sequence when maximally aligned and a match between the last assigned nucleobase of the nascent sequence and corresponding nucleobase of the raw targeting sequencing read. In some computer program products, the threshold level of accuracy of the sequencing the anchor segment is based on percentage of sequence identity and/or location of matched nucleobases between a raw target sequencing read and the known anchor segment. In some computer program products, the threshold level of accuracy requires a raw target sequencing read to have the correct nucleobase corresponding to the nucleobase of the anchor segment immediately adjacent the adjacent segment. In some computer program products, the raw sequencing reads comprise raw sequencing reads of first and second nucleic acid targets, the first nucleic acid target comprising the anchor segment linked to a first adjacent segment and the second nucleic acid target comprising the anchor segment linked to a second adjacent segment. In some computer program products, the first and second adjacent segments are overlapping segments. In some computer program products, the first and second adjacent segments are fragments of the same contiguous polynucleotide. In some computer program products, the first and second adjacent segments are non-overlapping segments. In some computer program products, the raw sequencing reads comprise raw sequencing reads of a plurality of nucleic acid targets, the different nucleic acid targets comprising the anchor segment linked to different adjacent segments; the different adjacent segments including overlapping and nonoverlapping segments. In some computer program products, the strand of the anchor segment is a primer incorporated into the nucleic acid target. In some computer program products, the strand of the anchor segment has 4-120 nucleobases, or 8-30 nucleobases. In some computer program products, the anchor segment is an oligonucleotide ligated to a nucleic acid fragment to be sequenced. In some computer program products, the anchor segment and adjacent segment are contiguous segments in a nucleic acid from nature. In some computer program products, the anchor segment is a repeat sequence. Some computer program products further comprise code for outputting the sequence of at least part of the adjacent segment. In some computer program products, the nucleic acid target is a homogeneous population of the same nucleic acid molecule. In some computer program products, the nucleic acid target is a heterogeneous population of variant nucleic acid molecules. In some computer program products, the variant nucleic acid molecules are variant nucleic acid molecules of the same virus. In some computer program products, the virus is HIV or HCV. In some computer program products, the variants are allelic variants.

The invention further provides a system for analyzing a nucleic acid target, comprising: (1) a system bus; (2) a memory coupled to the system bus; and (3) a processor coupled to the system bus operatively disposed to: (a) receive a population of raw target sequencing reads of a nucleic acid target comprising an anchor segment and an adjacent segment; the anchor segment being of known sequence and the adjacent segment being of unknown sequence; and at least some of the raw target sequencing reads containing sequencing errors; (b) evaluate the accuracy of sequencing of the anchor segment in different raw target sequencing reads by comparing raw target sequencing reads of the anchor segment with the known sequence of the anchor segment; (c) assign a subset of the raw target sequencing reads into an accepted class based on reaching at least a threshold level of accuracy of the sequencing of the anchor segment; (d) poll nucleobases at a position equidistant to the anchor segment sequence in raw target sequencing reads in the accepted class to determine a consensus nucleobase, which consensus nucleobase is assigned as the first nucleobase of a nascent sequence of the adjacent segment; (e) assign raw target sequencing reads having the consensus nucleobase determined in the prior polling step to remain in an accepted class and assigning raw target sequencing reads lacking the consensus nucleobase determined in the prior polling step to the rejected class; (f) optionally reassign a raw target sequencing read from the rejected class to the accepted class by scoring similarity of the raw target sequencing read to the nascent sequence and reintroducing the raw target sequencing read if the sequence similarity reaches at least a threshold level of similarity; and (g) repeat steps (d), (e) and optionally (f), except that a repetition polls a position adjacent the position poled in the previous polling step for raw target sequencing reads having the consensus nucleobase polled in the previous step or in the case of a raw target sequencing read reassigned from the rejected class to the accepted class and not polled in the previous polling step or if polled not having the consensus nucleobase in the previous polling step, the polling polls a position adjacent the position aligned with the last nucleobase of the nascent sequence to determine a consensus nucleobase, and the consensus nucleobases determined in successive repetitions are assigned as successive nucleobases in the nascent sequence of the adjacent segment.

In some systems, the threshold in (f) is at least 80% identity between the raw target sequencing read and nascent sequence when maximally aligned and a match between the last assigned nucleobase of the nascent sequence and corresponding nucleobase of the raw targeting sequencing read. In some systems, the threshold level of accuracy of sequencing the anchor segment is based on percentage of sequence identity and/or location of matched nucleobases between a raw target sequencing read and the known anchor segment. In some systems, the threshold level of accuracy requires a raw target sequencing read to have the correct nucleobase corresponding to the nucleobase of the anchor segment immediately adjacent the adjacent segment. In some systems, the raw sequencing reads comprise raw sequencing reads of first and second nucleic acid targets, the first nucleic acid target comprising the anchor segment linked to a first adjacent segment and the second nucleic acid target comprising the anchor segment linked to a second adjacent segment. In some systems, the first and second adjacent segments are overlapping segments. In some systems, the first and second adjacent segments are fragments of the same contiguous polynucleotide. In some systems, the first and second adjacent segments are nonoverlapping segments. In some systems, the raw sequencing reads comprising raw sequence reads of a plurality of nucleic acid targets, the different nucleic acid targets comprising the anchor segment linked to different adjacent segments; the different adjacent segments including overlapping and nonoverlapping segments. In some systems, the strand of the anchor segment is a primer incorporated into the nucleic acid target. In some systems, the strand of the anchor segment has 4-120 nucleobases. In some systems, the strand of the anchor segment has 8-30 nucleobases. In some systems, the anchor segment is an oligonucleotide ligated to a nucleic acid fragment to be sequenced. In some systems, the anchor segment and adjacent segment are contiguous segments in a nucleic acid from nature. In some systems, the anchor segment is a repeat sequence. In some systems, the processor is operatively disposed to outputting the sequence of at least part of the adjacent segment. In some systems, the nucleic acid target is a homogeneous population of the same nucleic acid molecule. In some systems, the nucleic acid target is a heterogeneous population of variant nucleic acid molecules. In some systems, the variant nucleic acid molecules are variant nucleic acid molecules of the same virus. In some systems, the virus is HIV or HCV. In some systems, the variants are allelic variants.

The invention further provides methods of differentially treating a patient population. Such methods involve sequencing samples from members of the patient population; wherein for each sample the sequencing comprises: (a) receiving a population of raw target sequencing reads of a nucleic acid target comprising an anchor segment and an adjacent segment; the anchor segment being of known sequence and the adjacent segment being of unknown sequence; and at least some of the raw target sequencing reads containing sequencing errors; (b) evaluating the accuracy of sequencing of the anchor segment in different raw target sequencing reads by comparing raw target sequencing read of the anchor segment with the known sequence of the anchor segment; (c) assigning a subset of the raw target sequencing reads into an accepted class based on reaching at least a threshold level of accuracy of the sequencing of the anchor segment; (d) polling nucleobases at a position adjacent the anchor segment sequence in raw target sequencing reads in the accepted class to determine a consensus nucleobase, which consensus nucleobase is assigned as the first nucleobase of a nascent sequence of the adjacent segment; (e) assigning raw target sequencing reads having the consensus nucleobase determined in the prior polling step to remain in an accepted class and assigning raw target sequencing reads lacking the consensus nucleobase determined in the prior polling step to the rejected class; (f) optionally reassigning a raw target sequencing read from the rejected class to the accepted class by scoring similarity of the raw target sequencing read to the nascent sequence and reintroducing the raw target sequencing read if the sequence similarity reaches at least a threshold level of similarity; and (g) repeating steps (d), (e) and optionally (f), except that a repetition polls a position adjacent the position poled in the previous polling step for raw target sequencing reads having the consensus nucleobase polled in the previous step or in the case of a raw target sequencing read reassigned from the rejected class to the accepted class and not polled in the previous polling step or if polled not having the consensus nucleobase in the previous polling step, the polling polls a position adjacent the position aligned with the last nucleobase of the nascent sequence to determine a consensus nucleobase, and the consensus nucleobases determined in successive repetitions are assigned as successive nucleobases in the nascent sequence of the adjacent segment. Different members of the patient population receive different treatment regimes depending on the determined sequence for the sample from each member.

The invention further provides computer-implemented methods of analyzing a nucleic acid target. Such methods involve (a) receiving a population of raw target sequencing reads of a nucleic acid target comprising an anchor segment and an adjacent segment; the anchor segment being of known sequence and the adjacent segment being of unknown sequence; and at least some of the raw target sequencing reads containing sequencing errors; (b) evaluating the accuracy of sequencing of the anchor segment in different raw target sequencing reads by comparing raw target sequencing reads of the anchor segment with the known sequence of the anchor segment; (c) assigning a subset of the raw target sequencing reads into an accepted class based on the accuracy of sequencing of the anchor segment in the raw target sequencing reads; and (d) determining a sequence of the anchor segment from raw target sequencing reads in the accepted class.

In some methods, step (d) comprises polling nucleobases at corresponding positions in raw target sequencing reads in the accepted class to determine a consensus nucleobase, which consensus nucleobase is assigned as the first nucleobase of a nascent sequence of the adjacent segment and wherein step (d) is repeated and the consensus nucleobases determined in successive repetitions are assigned as successive nucleobases in the nascent sequence of the adjacent segment. Some methods also involve assigning raw target sequencing reads having the consensus nucleobase determined in the prior polling step to remain in an accepted class and assigning raw target sequencing reads lacking the consensus nucleobase determined in the prior polling step to a rejected class. Some methods also involve designating a segment of the sequence of the adjacent segment as a new anchor segment and repeating the method to determine a sequence of an adjacent segment adjacent the new anchor segment.

The invention further provides a computer program product for analyzing a nucleic acid target, comprising code for receiving a population of raw target sequencing reads of a nucleic acid target comprising an adapter segment and an adjacent segment; the adapter segment being of known correct sequence and the adjacent segment being of unknown sequence; and at least some of the raw target sequences containing sequencing errors; code for evaluating the accuracy of sequencing of the adapter segment in different raw target sequences by comparing raw target sequencing reads of the anchor segment with the known correct sequence of the adapter segment; code for assigning a subset of the raw target sequences into an accepted class based on the accuracy of sequencing of the adapter segment in the raw target sequences; code for aligning at least some of the raw target sequences from the accepted class; and code for determining a sequence of at least part of the adjacent segment from the aligned sequences.

The invention further provides a system for analyzing a nucleic acid target, comprising: (a) a system bus; (b) a memory coupled to the system bus; and (c) a processor coupled to the system bus for receiving a population of raw target sequencing reads of a nucleic acid target comprising an adapter segment and an adjacent segment; the adapter segment being of known correct sequence and the adjacent segment being of unknown sequence; and at least some of the raw target sequences containing sequencing errors; evaluating the accuracy of sequencing of the adapter segment in different raw target sequences by comparing the raw target sequencing reads of the anchor segment with the known correct sequence of the adapter segment; assigning a subset of the raw target sequences into an accepted class based on the accuracy of sequencing of the adapter segment in the raw target sequences; aligning at least some of the raw target sequences from the accepted class; and determining a sequence of at least part of the adjacent segment from the aligned sequences.

The invention further provides methods of differentially treating a patient population. Such methods involve sequencing samples from members of the patient population; wherein for each sample the sequencing comprises receiving a population of raw target sequencing reads of a nucleic acid target comprising an adapter segment and an adjacent segment; the adapter segment being of known correct sequence and the adjacent segment being of unknown sequence; and at least some of the raw target sequences containing sequencing errors; evaluating the accuracy of sequencing of the adapter segment in different raw target sequences by comparing raw target sequencing reads of the anchor segment with the known correct sequence of the adapter segment; assigning a subset of the raw target sequences into an accepted class based on the accuracy of sequencing of the adapter segment in the raw target sequences; aligning at least some of the raw target sequences from the accepted class; and determining a sequence of at least part of the adjacent segment from the aligned sequences; wherein different members of the patient population receive different treatment regimes depending on the determined sequence for the sample from each member.

DEFINITIONS

Brief descriptions of some of the terms used in this application appear below. Some of these terms are further described in the rest of the specification.

A nucleobase is the base component of a nucleotide including any of the natural bases adenine (A), cytosine (C), guanine (G) and thymine (T) (for DNA) and A, C, G, and uracil (U) (for RNA) or analogs thereof subjectable to a sequencing reaction (e.g., support template-dependent incorporation of a complementary nucleobase). Nucleobases are sometimes referred to simply as bases.

A nucleobase attached to a sugar, can be referred to as a nucleobase unit, or monomer. Sugar moieties of a nucleic acid can be ribose, deoxyribose, dideoxyribose or similar compounds, e.g., with 2' methoxy or 2' halide substitutions. Nucleotides and nucleosides are examples of nucleobase units.

A nucleic acid target is the nucleic acid unit that is the subject of a sequencing reaction and gives rise to a sequencing read. A nucleic acid target comprises an anchor segment of known sequence and an adjacent sequence whose sequence is to be determined.

A raw target sequencing read is a contiguous sequence of nucleobases assigned during a sequencing reaction on a nucleic acid target. A raw target sequencing read may contain sequencing error(s). Thus raw target sequencing reads of the same nucleic acid target can differ from one another by virtue of sequencing errors.

Raw target sequencing reads can be assigned into an accepted class or rejected class. Raw target sequencing reads in the accepted class have passed a quality control measure. The quality control measure can be that the accuracy of sequencing of the anchor segment at least reaches a defined threshold, or that a raw target sequencing read contains a consensus nucleotide at an immediately previously polled position or a raw target sequencing read exceeds a threshold level of sequence similarity with the nascent sequence. Conversely raw target sequencing reads in the rejected class have failed a quality control measure. Typically, this quality control measure is failure to contain a consensus nucleobase at a polled position. Raw target sequencing can be assigned from the accepted class to the rejected class and vice versa as described below.

Polling compares the nucleobase occupying corresponding positions among raw target sequencing reads to determine a consensus nucleobase for that position.

A nascent sequence refers to a string of contiguous nucleobases identified by repeated polling cycles. The nascent sequence is the sequence of at least part of the adjacent segment of a nucleic acid target.

A threshold relates to one or more criteria for evaluating a nucleotide sequence, such as a raw target sequencing read. Such a threshold can be stored as code or provided by user input, or selected from a menu of possible thresholds when the method is performed.

In pairwise comparisons between two nucleic acid sequences, the nucleic acids are maximally aligned when the number of nucleobase matches is greatest. Percentage sequence identity can be defined as the number of matched nucleobases between aligned sequences divided by the number of nucleobases in one of the sequences (usually the known sequence if one sequence is known and the other is not). Extra nucleobases in an unknown sequence flanking the part of the unknown aligned with a known sequence are not scored.

Some or all of a raw target sequence read corresponds with the nucleic acid target (i.e., has the same sequence as a strand of the nucleic acid target other than sequence errors). The portion of a raw target sequencing read corresponding to an anchor segment of a nucleic acid target is the portion of the raw target sequencing aligned with the known sequence of the anchor segment when the raw target sequencing read is maximally aligned with the anchor segment. A portion of the raw targeting sequencing read adjacent to the segment corresponding to the anchor segment corresponds with the adjacent segment of the nucleic acid target.

A corresponding position in two or more nucleic acid sequences is a position aligned between the sequences when the sequences are maximally aligned over their entire length or at least a defined window thereof including the corresponding position (e.g., at least 10 or 20 nucleotides).

A "primer" is an oligonucleotide, typically between about 10 to 100 nucleotides in length, capable of selectively binding to a specified nucleic acid or "template" by hybridizing with the template. The primer provides a point of initiation for polymerase-mediated template-directed synthesis of a nucleic acid complementary to the template. Primers hybridizing to opposing strands of a double-stranded sequence are referred to as forward and reverse primers. An oligonucleotide primer used to initiate a sequencing reaction is referred to as a sequencing primer.

A "sequence variation" refers to a point or region of variation between two related nucleic acid molecules (e.g., at least 50% sequence identity and usually, at least 75%, 90, 95 or 99% sequence identity). A variation can be an insertion, deletion or substitution of one or more nucleobase differences between two nucleic acid molecules. A variation can be natural, such as allelic, or between species, strains or isolates or induced. Variations can be between different molecules of viral nucleic acids in a sample. Variations can be germline or somatic. A variation in nucleotide sequence can have no effect on an encoded amino acid sequence due to degeneracy of the code or can result in a corresponding amino acid change. If there is an amino acid change, the change may or may not affect the function of the encoded protein. If the change is to a stop codon, the encoded protein becomes prematurely truncated.

A copy of an anchor segment or adjacent segment or read thereof means an identical copy or substantially identical copy (e.g., at least 80% sequence identity) differing as a result of nucleobase unit misincorporations in template-dependent extension or sequencing errors.

Description of a range by integers representing the boundaries of the range also refers to all subranges defined by integers within the range.

BRIEF DESCRIPTION OF THE DRAWINGS

FIGS. 3A-F show sequencing using hairpin anchor segments.

DETAILED DESCRIPTION

I. General

Figure 1:
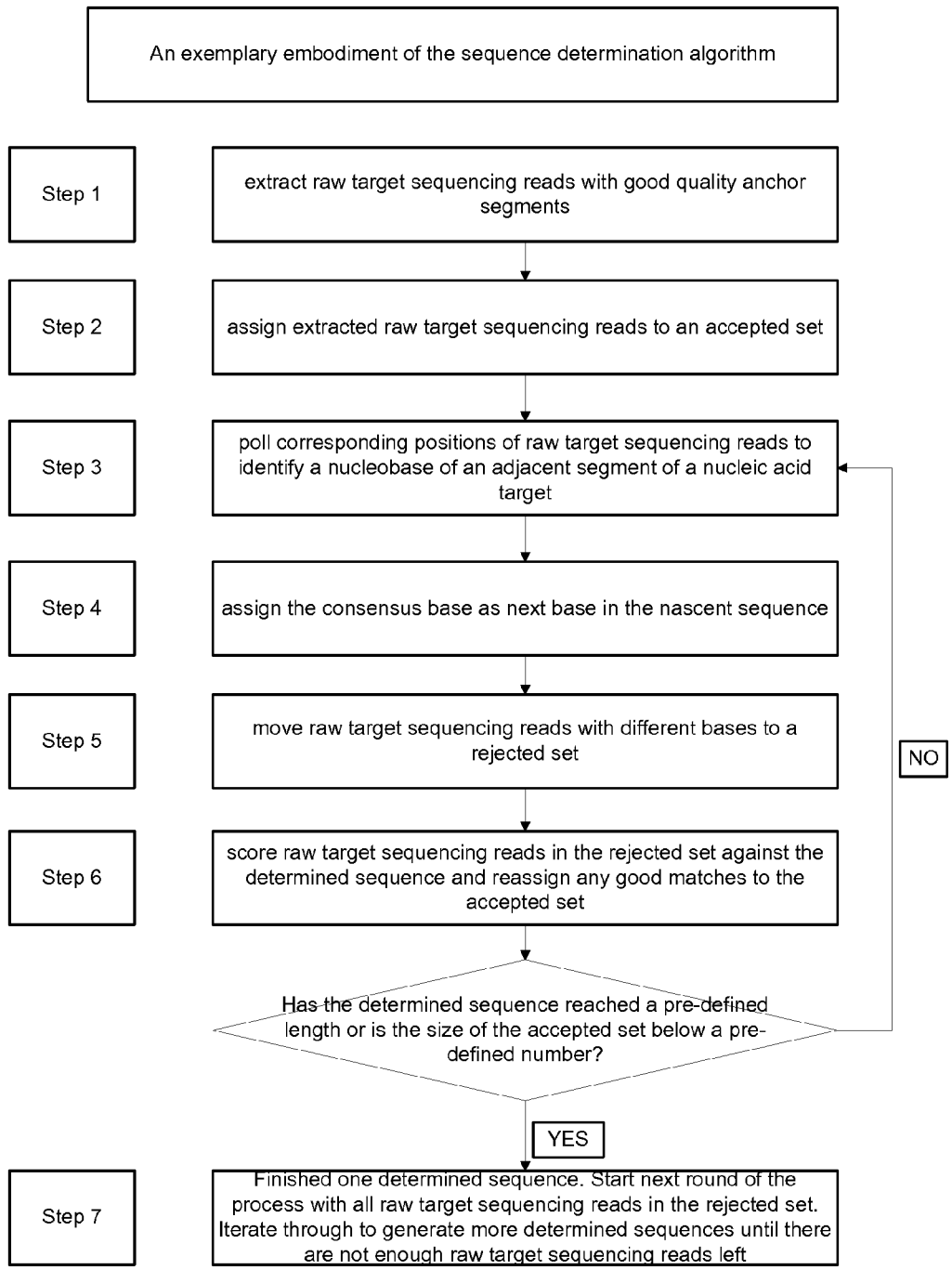
FIG. 1 shows a sequence determination algorithm.

The invention provides methods of determining a consensus sequence from multiple raw sequencing reads of a nucleic acid target. The nucleic acid target includes an anchor segment of known sequence and an adjacent segment of unknown sequence. The anchor segment provides a means to assess the quality of a raw target sequencing read. Because the anchor segment is of known sequence, comparison of the portion of the raw target sequencing read corresponding to the anchor segment provides a measure of quality of the raw target sequencing read. Raw target sequence reads exceeding a threshold level of accuracy are used in determining a consensus sequence for the adjacent target sequence. Raw target sequencing reads not meeting the threshold level of accuracy can be excluded from subsequent analysis.

The consensus sequence of the adjacent segment can be determined from raw target sequencing reads passing the threshold test by polling the target sequence reads at a corresponding position starting with a position adjacent the anchor segment. Successive polling steps can determine successive consensus nucleobases in a nascent sequence of the adjacent segment. Raw target sequencing reads can be removed or reintroduced from the accepted class depending on their correspondence to the most recently determined consensus nucleobase and/or the nascent sequence.

II. Nucleic Acid Target and Sequencing Read Thereof

The nucleic acid unit that is subject of a sequencing reaction and gives rise to a sequencing read (or two sequencing reads from opposing strands) is referred to as a nucleic acid target. A nucleic acid target can be single- or double-stranded, RNA or DNA. A nucleic acid target can be linear or circular. A nucleic acid target includes an anchor segment of known sequence and an adjacent segment whose sequence is to be determined. The adjacent segment can have a single unique sequence, can be a simple mixture of two variants (e.g., bi-allelic variants) or a complex mixture of variant sequences (e.g., a particular mRNA from a viral sample in which multiple viral strains are represented). The nucleic acid target can be of any length but preferably less than 200%, more preferably from 50% to 200%, of the maximum length of raw target sequencing read obtainable with whatever methodology is used. For example, the length of the nucleic acid target is sometimes from 20-50,000 nucleobases or by for a double stranded nucleic acid target. The nucleic acid target or its adjacent segment can be part of a larger target molecule, such as a gene, viral genome, chromosome or full genome. In this case, as in other sequencing methods, the larger target molecule can be broken down into fragments each of which can constitute a nucleic acid target or an adjacent segment of a nucleic acid target for purposes of the present methods. The sequences of multiple nucleic acid targets or adjacent segments thereof can be compiled from overlaps to provide the sequence of a larger nucleic acid molecule.

The anchor segment refers to a segment of known sequence present in the nucleic acid target. Anchors can be or various lengths, e.g., 8-30, 4-10, 4-20, 4-30, 4-50, or 4-120 nucleobases or base pairs). Anchor segments can be formed from deoxyribonucleotides or ribonucleotides or in some cases nucleotide analogs that can be subject of sequencing reactions.

Anchor segments can be nucleic acid sequences that are heterologous (i.e., not naturally associated with adjacent segment). Examples of heterologous anchor segments include primers or portions thereof used in amplifying adjacent segments, binding sites for sequencing primers, oligonucleotides ligated or otherwise attached to adjacent segments, such as SMRT Bell™ hairpin structures. Such ligated oligonucleotides including SMRT Bell structures can also serve as primer binding sites. Anchor segments can also be nucleic acid sequences naturally associated with the adjacent nucleic acid segment. Examples of anchor segments that are endogenous to the nucleic acid template include portions of a gene of known sequence, regulatory sequences, and repetitive sequences. The anchor segment preferably has a single (i.e., without sequence variation) completely known sequence. However, anchor segments which are of substantially completely known sequences, i.e., at least 80, 95, or 99% of nucleobases are known and without nucleobase variation can also be used.

Many sequencing methods already incorporate a segment that can serve as an anchor segment in the course of preparing a sequence template. In SMRT™ technology, a nucleic acid to be sequenced is ligated to hairpin structures (the same or different from each other), which can serve as anchor segments, one anchor segment joining at each end, forming circular template. The circular template includes strands of the nucleic acid to be sequenced (adjacent segment) and the hairpin anchor segments. Such a circular template can be sequenced in a single well to generate a sequencing read including alternating target strand and anchor segments (e.g., anchor segment 1, first strand of adjacent segment, anchor segment 2, second strand of target segment, anchor segment 1, first strand of adjacent segment, anchor segment 2, second strand of target segment and so forth) Oligonucleotide anchors can be ligated to libraries of nucleic acids to be sequenced (Illumina, Inc., 454 Corporation, SOLiD). Primers for the extension of a polynucleotide complementary to a nucleic acid to be sequenced e.g., poly (T) oligonucleotides, can also be used as anchors. Target nucleic acids can contain one, two or more copies of an anchor segment, each copy interspersed between copies of the adjacent segment (and/or its complement).

Performing a sequencing reaction on a nucleic acid target gives rise to a population of raw target sequencing reads of the nucleic acid target. A raw target sequencing read includes sequence of both the adapter segment and adjacent segment. The length of raw target sequencing of the same target can show some variation. A raw target sequencing read of an anchor segment and an adjacent segment can include the complete anchor segment or a designated portion of at least 10, 15, 20 or 30 nucleotides thereof abutting an adjacent sequence, and at least some, and preferably at least 25, 50, 75, 95 or 100% of the adjacent segment. A raw target sequence read refers to a contiguous nucleobase sequence assigned during a sequencing reaction performed on nucleic acid target. If the nucleic acid is double-stranded, the raw target sequencing read can correspond to either strand of the nucleic acid target. If the nucleic acid target is single-stranded, the raw target sequencing read can correspond to the nucleic acid target strand or its complement. The sequencing reaction can be performed using any type of sequencing methodology. Depending on the type of sequencing methodology used, the reaction provides a series of signals that are individually interpreted to mean one of A, C, T, G or U (or analogs thereof). This initial assignment of contiguous nucleobases forming the raw target sequence read may contain one or more errors (i.e., insertions, deletions, substitutions and combinations thereof). Different raw target sequences of the same nucleic acid target typically contain errors in different positions. Errors can result from misincorporation of nucleotides in amplification or sequencing, reading errors associated with instrumentation and the enzymatic sequencing process, and errors introduced in base-calling.

Raw target sequencing reads can be in the form first generated by a sequencing reaction without any processing to remove errors or can have been subject to partial processing to remove some errors but in which some sequencing errors remain.

A population of raw target sequencing reads of a nucleic acid target can be generated by repeatedly sequencing the same nucleic acid target molecule, sequencing a nucleic acid containing multiple copies of the nucleic acid target (e.g., repeats generated by rolling circle replication), or by sequencing multiple individual copies of the nucleic acid target or larger molecule containing some or all of the nucleic acid target. Examples of methods of generating replicate sequence information from a single molecule are provided, e.g., in U.S. Pat. No. 7,476,503; US 2009/0298075, 2010/0075309, 2010/0075327, 2010/0081143. For example, a circular template can be used to generate replicate sequence reads of the target sequence by allowing a polymerase to synthesize a linear concatemer by continuously generating a nascent strand from multiple passes around the template molecule. The nascent strand can contain alternating reads of an anchor segment and adjacent segment. Optionally, the anchor segment itself alternates between first and second anchor segment and the adjacent segment alternates between its two strands. The population of raw target sequencing reads of a nucleic acid target may or may not begin and end at the same position as each other. However, a nucleic acid read should include at least sufficient numbers of nucleobases of the anchor segment to permit evaluation of accuracy of sequencing of the anchor segment, and at least some of the adjacent segment. Preferably raw target sequencing reads of the same target nucleic acid begin at the same point, include all of an anchor segment and as much of an adjacent segment as is compatible with the sequencing technology. Often there is some variation in the read length of different raw sequencing reads, which is preferably reflected in variation of the length of adjacent segment included in the read. The read lengths of different sequencing technology vary widely. Thus, the amount of adjacent sequence included in a read length can vary from e.g., 10 nucleobases to 50,000 nucleobases.

Raw target sequencing reads may or may not be provided with additional information as well as pure sequence data. Additional information can include estimations of per-position accuracy, features of underlying sequencing technology output (e.g., trace characteristics, integrated counts per peak, shape/height/width of peaks, distance to neighboring peaks), signal-to-noise ratios, power-to-noise ratio, signal strength, and the like.

III. Generation of a Population of Raw Target Sequencing Reads of a Nucleic Acid Target (a) Template Preparation Nucleic acid targets can be amplified before sequencing, or not amplified and used directly in sequencing. Amplification can be performed with a pair of forward and reverse primers as in conventional PCR. Optionally the forward and reverse primers include 5' tails lacking complementary to the nucleic acid being amplified. Such tails can serve to provide a binding site for sequencing primers. Some or all of the forward and/or reverse primer can be used as the anchor segment of the nucleic acid target. The forward and reverse primers can serve as anchor segments for the opposing strands of a double-stranded nucleic acid target.

In other methods, after fragmenting a nucleic acid and repairing fragment ends, if needed, hairpin anchors can be ligated onto the ends of these fragments therefore forming a circularized template for sequencing. FIG. 3A shows a sample preparation using two hairpin anchors termed anchors I and II.

A DNA polymerase can be used to open the anchor-ligated fragments into circularized templates. The anchors serve as binding sites for sequencing primer(s) as well as their role in assessing quality of sequencing reads in the present methods. FIG. 3B shows generation of continuous reads of both strands of a fragment interspersed with anchors I and II. The reads, then, include multiple reads of the same fragment by the polymerase reading around the circular template multiple times. In FIG. 3B, four reads of forward strand and three reads of reverse strand have been generated before the sequencing reaction is terminated.

For analysis, the different sequencing reads can be segregated by an anchor segment. In this example, raw target sequences can be grouped into four subsets. In the first set, anchor I segments are aligned to provide a framework for base-polling sequences of forward strands adjacent to the 3' end of the anchor I segment (FIG. 3C). In the second set, anchor II segments are aligned to provide a framework for base-polling sequences of reverse strands adjacent to the 3' end of the anchor II (FIG. 3E). In the third and fourth sets, anchor I or II segments are aligned to provide frameworks for base-polling sequences of forward strands (FIG. 3F) and reverse strands (FIG. 3D) adjacent to the 5' end of the anchor I and II. Anchors I and II can be the same or different from one another in terms of sequence.

Some amplification methods amplify many nucleic acid molecules in parallel. One such method is amplification on beads using emulsion PCR methods (see, e.g., US US2005/0042648, US2005/0079510, and US2005/0130173 and WO 05/010145). Another such method is amplification on a surface using bridge amplification to form nucleic acid clusters. Methods of generating nucleic acid clusters for use in high-throughput nucleic acid sequencing have been described (see, e.g., U.S. Pat No. 7,115,400, US 2005/0100900 and 2005/0059048, and WO 98/44151, WO 00/18957, WO 02/46456, WO 06/064199, and WO 07/010251. Bridge amplification refers to a solid phase replication method in which primers are bound to a solid phase, e.g., flow cell, microarray, and the like. The extension product from one bound primer forms a bridge to the other bound primer.

(b) Sequencing

One class of sequencing reactions that can be used are sequencing-by-synthesis (SBS) methods. Sequencing by synthesis refers to the sequencing of a nucleic acid sequence by synthesis of the complementary strand (see US 2007/0166705, 2006/0188901, 2006/0240439, 2005/0100900, 2006/0281109; U.S. Pat. No. 7,057,026; WO 05/065814, WO 06/064199 and WO 07/010251).

SBS techniques can utilize nucleotide monomers that have a label moiety or those that lack a label moiety. If a label is present, the monomers can have the same or different label as each other. If present, incorporation events can be detected based on a characteristic of the label(s), such as fluorescence of the label(s); a characteristic of the nucleotides such as molecular weight or charge; a byproduct of incorporation of the nucleotides, such as release of pyrophosphate or a hydrogen ion; or the like.

In some methods, the incorporation of nucleobase units is detected by measuring the release of a label from the nucleobase unit being incorporated. A preferred approach as with SMRTbell™ template sequence is to use nucleobase units fluorescently labeled on the terminal phosphate of the nucleobase unit. (Korlach et al., *Nucleosides, Nucleotides and Nucleic Acids*, 27:1072-1083, 2008. The label is cleaved from the nucleotide monomer on incorporation of the nucleotide into the polynucleotide. Accordingly, the label is not incorporated into a nascent nucleic acid, increasing the signal:background ratio.

Pyrosequencing detects the release of inorganic pyrophosphate (PPi) as particular nucleotides are incorporated into the nascent strand (Ronaghi, et al., *Analytical Biochemistry* 242(1):84-9, 1996; Ronaghi, M., *Genome Res.* 11(1): 3-11, 2001; Ronaghi, et al., *Science* 281(5375):363, 1998; U.S. Pat. Nos. 6,210,891, 6,258,568 and 6,274,320). Released PPi can be detected by, e.g., a process in which the released PPi is immediately converted to adenosine triphosphate (ATP) by ATP sulfurylase, and the level of ATP generated is detected via luciferase-produced photons.

A hydrogen ion released on incorporation of a nucleotide can be detected as a change in voltage by for example the Ion Torrent machine (Life Technologies, Inc).

In another example, cycle sequencing is accomplished by stepwise addition of reversible terminator nucleotides containing, for example, a cleavable or photobleachable dye label. The technique was commercialized by Solexa (now Illumina Inc.), and described, for example, in U.S. Pat. Nos.

7,427,67, 7,414,163 and 7,057,026, and WO 91/06678 and WO 07/123744. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides. In cases where two or more different nucleotides are present in a sequencing reagent, the different nucleotides can be distinguishable from each other. For example, the different nucleotides present in a sequencing reagent can have different labels and they can be distinguished using appropriate optics as exemplified by the sequencing methods developed by Solexa (now Illumina, Inc.).

SBS can utilize nucleotide monomers that have a terminator moiety or those that lack any terminator moieties. For SBS techniques that utilize nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed by Solexa (now Illumina, Inc.). Methods utilizing nucleotide monomers lacking terminators include, for example, pyrosequencing and sequencing using γ-phosphate-labeled nucleotides. In methods using nucleotide monomers lacking terminators, the number of different nucleotides added in each cycle can be dependent upon the template sequence and the mode of nucleotide delivery. Reversible terminators/cleavable fluors can include fluor linked to the ribose moiety via a 3' ester linkage (Metzker, *Genome Res.* 15:1767-1776 (2005). Other approaches have separated the terminator chemistry from the cleavage of the fluorescence label (Ruparel et al., *Proc. Natl. Acad. Sci. USA* 102: 5932-7 (2005). Ruparel et al. described the development of reversible terminators that used a small 3' allyl group to block extension, but could easily be deblocked by a short treatment with a palladium catalyst. The fluorophore was attached to the nucleobase via a photocleavable linker that could easily be cleaved by a 30 second exposure to long wavelength UV light. Thus, either disulfide reduction or photocleavage can be used as a cleavable linker. Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluor and effectively reverses the termination (see U.S. Pat. Nos. 7,427,673 and 7,057,026).

Another class of sequencing reactions that can be used are nanopore sequencing methods. In nanopore sequencing, (Deamer, & Akeson, *Trends Biotechnol.* 18:147-151 (2000); Deamer & Branton, *Acc. Chem. Res.* 35:817-825 (2002); Li, et al., *Nat. Mater.* 2:611-615 (2003)), the target nucleic acid or nucleotides released from the target nucleic acid pass through a nanopore. The nanopore can be a synthetic pore or biological membrane protein, such as α-hemolysin. As the target nucleic acid or nucleotides pass through the nanopore, each base-pair (or base) can be identified by measuring fluctuations in the electrical conductance of the pore. (U.S. Pat. No. 7,001,792; Soni, G. V. & Meller, *Clin. Chem.* 53:1996-2001 (2007); Healy, K., *Nanomed.* 2:459-481 (2007); Cockroft, et al., *J. Am. Chem. Soc.* 130:818-820 (2008)).

Another class of sequencing reactions is sequencing by ligation (see U.S. Pat. Nos. 6,969,488, 6,172,218, and 6,306, 597). A target nucleic acid is hybridized to an oligonucleotide and contacted with several probes and a ligase. Only a probe complementary to the target nucleic acid can be ligated to the oligonucleotide. The identity of the probe indicates part of the sequence of the target nucleic acid.

(c) Sequencing Platforms

Examples of sequencing platforms include the Genome Sequencer FLX System (Roche) that employs pyrosequencing to provide long read lengths and very high single-read accuracy, 454 FLX™ or 454 TITANIUM™ (Roche), the SOLEXA™ Genome Analyzer (Illumina), the HELISCOPE™ Single Molecule Sequencer (Helicos Biosciences), the SOLID™ DNA Sequencer (Life Technologies/Applied Biosystems) instruments) which performs sequencing by ligation, SMRT™ technology (Pacific Biosystems), Ion Torrent (LifeTech) as well as other platforms still under development by companies such as Intelligent Biosystems. Other sequencing platforms include OmniMoRA (Reveo, Inc. (Elmsford, N.Y.)), VisiGen® (VisiGen Biotechnologies, Inc. (Houston, Tex.), now Life Technologies (Carlsbad, Calif.)), SBS technology (Intelligent Bio-Systems (Waltham, Mass.)), or Hybridization-Assisted Nanopore Sequencing (HANS; NABsys Inc. (Providence, R.I.)), or the target fragment isolated may be sent to a third party for further analysis and/or sequencing (e.g., Really Tiny Stuff, Inc., Cohasset, Mass.).

A sequencing platform provided by Helicos Biosciences Corp. uses TRUE SINGLE MOLECULE SEQUENCING (tSMS)™ technique (Harris et al., *Science* 320:106-109 (2008). The tSMS™ technique uses a library of target nucleic acids prepared by the addition of a 3' poly(A) tail to each target nucleic acid. The poly(A) tail hybridizes to poly(T) oligonucleotides anchored on a glass cover slip. The poly(T) oligonucleotide can be used as a primer for the extension of a polynucleotide complementary to the target nucleic acid.

Sequencing platforms implementing real-time monitoring of DNA polymerase activity can be used. For example, nucleotide incorporations can be detected through fluorescence resonance energy transfer (FRET) interactions between a fluorophore-bearing polymerase and γ-phosphate-labeled nucleotides as described, for example, in U.S. Pat. Nos. 7,329,492 and 7,211,414. Nucleotide incorporations can also be detected with zero-mode waveguides as described, for example, in U.S. Pat. No. 7,315,019 and using fluorescent nucleotide analogs and engineered polymerases as described, for example, in U.S. Pat. No. 7,405,281 and US 2008/0108082. The illumination can be restricted to a zeptoliter-scale volume around a surface-tethered polymerase such that incorporation of fluorescently labeled nucleotides can be observed with low background (Levene et al., *Science* 299:682-686 (2003); Lundquist et al., *Opt. Lett.* 33:1026-1028 (2008); Korlach et al., *Proc. Natl. Acad. Sci. USA* 105:1176-1181 (2008).

Single-molecule, real-time (SMRT™) DNA sequencing technology is described in U.S. Pat. Nos. 7,181,122, 7,302, 146, and 7,313,308. SMRT chips and similar technology can be used in association with nucleotide monomers fluorescently labeled on the terminal phosphate of the nucleotide (Korlach et al., *Nucleosides, Nucleotides and Nucleic Acids,* 27:1072-1083, 2008). The label is cleaved from the nucleotide monomer on incorporation of the nucleotide into the polynucleotide. Accordingly, the label is not incorporated into the polynucleotide, increasing the signal:background ratio.

(d) Multiplexing

As already described, some amplification methods amplify multiple nucleic acids in parallel. Sequencing reactions can also be carried out in multiplex formats such that multiple different nucleic acid targets are manipulated simultaneously. For example, different nucleic acid targets can be treated in a common reaction vessel or on a surface of a particular substrate. This allows convenient delivery of sequencing reagents, removal of unreacted reagents and detection of incorporation events in a multiplex manner. Nucleic acid targets can also be in an array format in a spatially distinguishable manner. The target nucleic acids can be bound by direct covalent attachment, attachment to a bead or other particle or binding to a polymerase or other molecule that is attached to the surface. The array can include a single copy of a nucleic acid target at each site (also referred to as a feature) or multiple copies having the same sequence can be present at each site or feature.

In deep sequencing a plurality of related or identical nucleic acids are attached to the surface of a reaction platform (e.g., flow cell, microarray, and the like) (see e.g., Bentley et al., *Nature* 2008, 456:53-59). The attached DNA molecules can be amplified in situ and used as templates for synthetic sequencing (i.e., sequencing by synthesis) using a detectable label (e.g. fluorescent reversible terminator deoxyribonucleotide). Representative reversible terminator deoxyribonucleotides include 3'-O-azidomethyl-2'-deoxynucleoside triphosphates of adenine, cytosine, guanine and thymine, each labeled with a different recognizable and removable fluorophore, optionally attached via a linker. When fluorescent tags are employed, after each cycle of incorporation, the identity of the inserted base may be determined by excitation (e.g., laser-induced excitation) of the fluorophores and imaging of the resulting immobilized growing duplex nucleic acid. The fluorophore, and optionally linker, can be removed by conventional methods, thereby regenerating a 3' hydroxyl group ready for the next cycle of nucleotide addition.

IV. Determining a Consensus Sequence

The present methods can be used to provide a consensus sequence of at least part of the adjacent segment in a nucleic acid target from a population of raw target sequencing reads of the target. If an initial population of raw target sequences do not all contain the same anchor segment, the population can be sorted to give a population of raw target sequencing reads in which part of the sequencing read is of the same anchor segment. The members of this population are then evaluated for accuracy of sequencing of the anchor segment. Members of the population in which the accuracy at least reaches (and preferably exceeds) a threshold value are carried forward for subsequent consensus sequence determination. The raw target sequencing reads carried forward are designated in a class of accepted raw sequencing reads and can be literally or conceptually assigned to an accepted class. This class is usually in the form of stored information in computer system. Members of the population failing to reach the threshold value are typically discarded and not further used in the analysis. The threshold value can be based on the percentage sequence identity between the segment of a raw target sequencing read and corresponding known sequence of an anchor segment and/or the location of matched and mismatched nucleotides between. Sequence identity is preferably determined over the full length of the known sequence of the anchor segment maximally aligned with the raw target sequencing read. Sequence identity is scored as the number of matched nucleotides divided by the number of nucleotides in the anchor segment. The sequence identity is preferably at least 80, 85, 90, 95, 99 or 100%. The threshold can additionally or alternatively be defined by the location of matched nucleotides. The nucleotide immediately adjacent to the first nucleobase of the portion of the sequencing read corresponding to the adjacent segment is particularly significant. Thus, the threshold can require this nucleobase to be accurately determined. The threshold can require a contiguous segment of at least 2, 3, 4, 5, 6, 7, 8, 9 or 10 nucleobases adjacent the first nucleobase of corresponding to the adjacent segment to be correctly determined.

Having selected a subset of raw target sequencing reads in which the accuracy of the portion of the read corresponding to an anchor segment exceeds a threshold, a consensus of the portions of the sequencing reads corresponding to the adjacent segment can be determined by a method including any or all of the polling, discarding or reassigning steps described below.

Preferred methods assign successive nucleobases to a nascent sequence of the adjacent sequence by a process referred to as polling. Polling compares nucleobases occupying a corresponding position among raw target sequencing reads to determine a consensus nucleobase at the corresponding position. A consensus nucleobase is the most represented nucleobase in the different raw target sequencing reads being polled at the polled position. If two or more nucleobases are tied for most represented, any of the tied bases can be regarded as the consensus nucleobase. The other tied nucleobases can be treated as non-consensus or can be treated as potential sites of sequences variations as discussed in more detail below. Nucleobases that are not tied, but less represented, can also be treated as potential sites of sequences variations. In most cases, the sites for sequence variations are not tied bases. The position for the initial polling step is defined by reference to the anchor segment so the position is equidistant from the sequence of the anchor segment in the raw target sequencing being polled. Typically the position is immediately adjacent the sequence of the anchor segment in the direction in which the sequencing read is performed (typically beginning at the adapter segment and moving into the adjacent segment). Polling determines the consensus nucleobase at this position and this nucleobase is assigned as a nucleobase of a sequence of the adjacent segment, typically the first base. Raw target sequencing reads having the consensus nucleobase at the position polled are retained as accepted sequences. Raw target sequencing reads lacking the consensus nucleobase at the position polled are designated as rejected raw target sequencing reads. The rejected sequencing reads can literally or conceptually be assigned to a rejected class. The rejected class, like the accepted class, is typically electronic information in computer memory. At this point, some rejected raw target sequencing reads may be reassigned as accepted sequences in a process that will be described in more detail below.

For raw target sequencing reads polled in the previous step and retained as accepted sequences, a further polling step is performed on the next nucleobase (adjacent the nucleobase polled in the previous step). The directionality is usually the same as that in which the raw target sequencing read is developed beginning at or before the anchor segment and moving into the adjacent segment. Thus, for a sequencing-by-synthesis method, the raw target sequencing read is determined in a 5'-3' direction and nucleobases in successive polling steps also usually move along the raw targeting sequences in a 5'-3' direction. However, successive polling steps can also be performed in the opposite directed to that of synthesis (i.e., 3'-5'). Again, a consensus nucleobase is determined at a corresponding position between the accepted raw target sequencing reads, and this nucleobase is assigned as the next nucleobase of the nascent sequence of the adjacent segment. Again, raw target sequencing reads having the consensus nucleobase at the polled position are retained as accepted sequences. Raw target sequencing reads lacking the consensus nucleobase at the polled position are designated as rejected sequences.

Further iterations of the poling step can be performed. A repetition polls a position adjacent the position polled in the previous polling step for accepted raw target sequencing read. The determined consensus nucleobase in successive repetitions form successive nucleobases in the nascent segment of the adjacent segment. After a polling step, raw target sequencing reads having the consensus nucleobase at the polled position are retained as accepted and raw target sequencing reads lacking the consensus nucleobase are designated as rejected.

As mentioned above, in any cycle of the above methods, rejected raw target sequencing reads can be considered for reassignment as accepted raw target sequencing reads. Usually, reassignment, if performed, occurs after the polling step and after any raw target sequencing reads not having the consensus nucleobase in the polling step are assigned as rejected sequencing reads. Reassignment allows the consensus sequence determination to make use of information from raw target sequencing reads that do not conform to the consensus sequence of the adjacent segment in one region but do in one or more other regions. Such lack of conformity may be the result of a sequencing error, a polymorphism, deletions of part of the adjacent segment of the nucleic acid target or a heterogeneous mixture of nucleic acid targets in which adjacent segments do not necessarily begin and end at the same point of a large molecule. Rejected raw target sequencing reads are reassigned based on overall sequence identity with the nascent sequence and/or the location of matched nucleobases between the rejected raw target sequencing read and the nascent sequence. A rejected raw target sequencing read is aligned with the nascent sequence to maximize matched nucleotides. The alignment can be performed over the entire length of the nascent sequence or a window of e.g., the last 10 or 20 nucleotides. Percentage sequence identity can be calculated as the number of matched nucleobases with the nascent sequence minus deletions or insertions divided by the number of nucleobases of the nascent sequence. The calculation can be performed over the entire nascent sequence or a window thereof, for example, the last 20 or 10 nucleotides. The threshold for sequence identity can be defined as at least 80, 85, 90, 95, 99 or 100% over the defined window. Additionally, or alternatively, the threshold can require identity between the last nucleotide determined for the nascent sequence and the corresponding nucleotide of the rejected raw target sequence. The threshold can alternatively require identity between the last 2, 3, 4, 5, 6, 7, 8, 9 or 10 determined nucleotides of the nascent sequence and the corresponding nucleotides of the raw target sequencing read. An exemplary criterion for reassigning a rejected raw target sequencing read to be an accepted raw target sequencing read is an overall sequence identity of at least 80% and identity between the last determined nucleobase of the nascent sequence and corresponding nucleobase of the raw target sequencing read.

Rejected raw targeting sequencing reads can be assessed for reassignment to accepted status in any iteration of the method. The fact that rejected raw targeting sequencing are assessed may or may not result in one or more of them being found to meet the threshold for reassignment to accepted status. In some methods, a reassignment is made in at least one cycle. In some methods, a reassignment is performed at least 5 times in at least 20 cycles. In some methods, a reassignment is performed at least 20 times in at least 100 cycles. Reassignment or at least assessment of rejected raw target sequencing reads for reassignment can also performed at regular intervals, e.g., every 5 or 10 polling steps, or after the first 20 polling steps, and then after each 5 or ten polling steps thereafter.

The interval between a raw target sequencing read being assigned from the accepted to rejected class and then back to accepted can be as short of one cycle. For example, a raw target sequencing read having a single nucleobase insertion can be assigned from accepted to rejected because the inserted nucleobase is not the consensus nucleobase at the relevant position being polled. However, the same raw target sequencing read can then be immediately reassigned because its next nucleobase is the last polled nucleobase in the consensus sequence and it overall meets the threshold criteria for reassignment to accepted status. In this case, the raw target sequence read effectively misses only one nucleobase being read corresponding to the nucleobase insertion. For raw target sequencing reads having a single nucleobase substitution, when the nucleobase occupied by the substitution is polled, the raw target sequencing read does not have the consensus nucleobase and is assigned to the rejected class. However, after the next round of polling, the raw target sequencing read does have a nucleobase the same as the most recently determined nucleobase of the nascent sequence and can be returned to the accepted class (assuming other threshold criteria are met). In this case, the raw target sequencing read has effectively missed two nucleobases being read in determining the consensus sequence, the substituted nucleobase and the next adjacent nucleobase. Other raw target sequencing reads are present in the rejected class of sequences for longer periods or may never be returned to the accepted raw target sequencing reads.

Returning raw target sequencing reads either were not polled in the previous polling cycle, of if polled, yielded a non-consensus nucleobase. In the polling cycle immediately after a raw targeting sequencing read is returned to the accepted class of sequencing reads, the position polled is that immediately adjacent to the position aligned with the last nucleobase determined in the nascent sequence so as to permit assessment of the next nucleobase in the nascent sequence Immediately returning raw sequencing reads are polled together with raw target sequences already having accepted status to determine a consensus nucleobase. If a returning raw target sequencing read remains in the accepted category following its initial return, positions for subsequent polling can be determined as for other raw targeting reads in the accepted category. That is, the position for one polling cycle is the position adjacent that in the previous polling cycle preserving a directionality throughout polling such that successive nucleobases in the nascent sequence are determined. For raw sequencing reads generated in a 5'-3' orientation, the directionality of polling successive nucleobases is also usually 5'-3' but can also be 3'-5'.

The steps of polling, and assigning raw target sequencing reads are continued assigning successive nucleobases to the nascent sequence until a sufficient length of nascent sequence has been determined or the complete length of the adjacent segment has been determined or the number of raw target sequencing reads in the accepted class falls below a threshold limit. The accuracy of raw target sequencing reads typically reduces further along the read. As the accuracy is reduced, more raw target sequencing reads are designated as rejected sequencing reads and fewer, if any, are returned to the accepted class. The number of cycles of polling (and auxiliary assigning and reassigning steps) depends on the length of the adjacent segment and the length of reasonably accurate sequencing read, which in turn depends on the sequencing technique. Depending on the sequencing technique, the number of polling cycles can be e.g., at least 2, 5, 10, 50, 100, 200, 1000, 10,000 or 50,000.

The process described above identifies the consensus nucleobases occupying successive positions of the nascent sequence. The process can be varied or extended to determine variants of the consensus sequence as well. The variations can be allelic variations, variations between isolates, strains or species, or sequence variations between a population of viral molecules in a clinical sample, among others. Such variations can be identified by forming branched consensus sequences as the method described above is performed or by repeating the method on raw target sequencing reads that have been rejected at one or more cycles of the method. Branching starts by identifying two (or more) consensus nucleobases in a polling step. The nucleobases may have the same or similar representation in the accepted raw target sequencing reads, or one nucleobase may have higher representation than the other but both nucleobases still have a representation exceeding a threshold. In this situation, the nascent sequence is branched into two nascent sequences with the two consensus nucleobases being the first nucleobases in the two branched arms of the nascent sequence. Raw target sequencing reads having either of the consensus nucleobases are retained in the accepted class. Subsequent consensus nucleobases are assigned to both branched nascent sequences. A branched nascent sequence can itself be subject of further branching at a further position of sequence variation.

Alternatively of additionally, a consensus sequence of the adjacent segment can be determined without branching and the process repeated using raw targeting sequences that have been rejected in at least one cycle and preferably returned to the accepted class subsequently. These sequences are a likely source of sequence variants because a raw targeting sequencing read will be rejected if it includes one or more nucleobase differing from the consensus but can then be returned to the accepted class based on identity between one or more subsequently determined nucleobases and the consensus nucleobase. Performing further iterations of the method on raw targeting sequencing reads that have returned to the accepted class can thus be used to identify one or more variants of the initially determined consensus sequence of the adjacent segment.

Once the sequence of an unknown adjacent segment has been determined by repeated polling and discarding subreads as described above, the process can be repeated starting with raw target sequencing reads in the rejected class after performing the process. If the initial population of raw target sequencing reads including sequencing reads of multiple nucleic acid targets includes the same anchor segment linked to different adjacent segments, repeating the method can be used to determine the sequence of a different adjacent segment. The method initially determines the sequence of the predominant adjacent segment in such a mixture, with nucleic acid targets containing other adjacent segments being designated as rejected sequences. Repeating the method on the rejected sequences, thus allows determination of a consensus sequence for a second and different adjacent segment. The method can be repeated multiple times to determine the consensus sequence of multiple different adjacent segments.

An initial population of raw target sequencing reads sometimes includes sequencing reads of nucleic acid target incorporating different anchor segments. Different anchor segments can be used to distinguish reads of opposing strands of an adjacent segment or different adjacent segments. If different segments, the segments can be overlapping or part of the same larger nucleic acid molecule (e.g., a genome or chromosome). In this case, the raw target sequencing reads can usually be segregated by anchor segment so as to be in groups in which the read is that of the same anchor segment. The above methods can be applied separately to the raw target sequencing reads in the same group.

In a further variation, after determining a consensus sequence of an adjacent segment, part of the consensus sequence is itself used as an anchor segment in an additional iteration of the method. The additional iteration can start with sequences in the rejected class and/or any sequences remaining in the accepted class. The adjacent segment for the new anchor segment can overlap in full, in part or not at all with adjacent segment from the first iteration. If the adjacent segment overlaps completely, then the additional iteration provides a check and possible identification and correction of errors in the consensus sequence. If the adjacent segment is completely beyond the prior adjacent segment, then an additional consensus sequence is determined contiguous with the consensus sequence initially determined. If the additional adjacent segment is partially within and partially beyond the prior adjacent segment, then it both checks and extends the consensus read from the prior adjacent segment.

The result of the above method is at least a consensus sequence of a part of an adjacent segment. Sometimes alternative consensus sequences including a sequence variation are also provided. Sometimes consensus sequences for both strands of an adjacent segment are provided. Sometimes consensus sequences of multiple adjacent segments are provided. If consensus sequences are provided for both strands of an adjacent segment and there are any discrepancies, the discrepancies can be rechecked, optionally using an alternative sequencing method. As already noted forward and reverse sequences can be readily generated using certain sequencing platforms such as SMRT technology. Discrepancies sometimes arise from reading a particular nucleobase but not its complementary nucleobase. If consensus sequences are provided for multiple adjacent segments that are part of the same larger nucleic acid molecule the sequences can be combined based on overlaps by conventional methods.

Determining sequence variations requires distinguishing between sequencing errors and true sequence variations. Such a distinction can be made by setting certain filtering criteria, or by setting a rank threshold such as a quality score. One example of a filter for identifying error or variant at any given position is to quantify the number of times each nucleobase appeared at a given position. The nucleobase that occurs the majority of the time is likely the correct residue for that position. For the remaining non-majority nucleobases that appeared at a given position, if their occurrence is relatively even meaning about 33% for each, then is can be determined that for this given position, the mismatches were errors. On the other hand, should one of the remaining non-majority nucleobases appear more frequently than the others, then that nucleobase is likely the correct nucleobase of a minority species variant. Of course, quantifying the relative occurrence of the non-majority nucleobases should take into account the statistical significance of any differences in occurrences. An example of a quality metric is a Phred score (Hillier et al., Genome Res. 8(3):175-185, 1998). for Sanger sequencing, which is calculated based on fluorescent signal characteristics for the 4 nucleobase channels at a given position. A high Phred score for a predominant non-majority nucleobase at a given position would be an indication that the variant is present in a legitimate minority species. It is often useful to calculate a log odds ratio based on quality scores for each potential nucleobase. The log odds ratio is the natural log of the ratio of odds that a nucleobase is present based on experimental data, and represents the likelihood that a particular nucleobase was correctly read at a given position. Thus, a high log odds ratio for the predominant non-majority nucleobase at a given position suggests that it is a valid nucleobase at that position in a legitimate minority species.

Sequencing errors and true sequence variations can be further distinguished by comparing determined sequences of multiple adjacent segments. For example, adjacent segments covering different but partially overlapping regions of a larger nucleic acid molecule suspected of having the sequence variations can be compared. True sequence variations are more likely to appear in most, if not all, partially overlapping sequences. Special care should be taken, however, when phasing multiple SNPs within chromosomes. For example, when phasing multiple SNPS within chromosomes, it is possible that all SNPs are located in only one allele. In these cases, data generated from each allele should not be combined. Preferably, determined sequences from each allele should be compared against each other to phase multiple SNPs.

FIG. 1 provides an overview of an exemplary analysis schema for analyzing a target nucleic acid. At step 1, raw target sequencing reads were selected to create a class of raw target sequencing reads having high-quality reads of the anchor segment. Different criteria can be applied in extracting such raw target sequencing reads. For examples, raw target sequencing reads preferably include only reads having sequences that are 100% identical to the known, correct anchor segment sequence. Optionally, reads can be filtered to create a class of raw target sequencing reads having sequences that are at least 99%, 95%, 90%, 85%, 80%, 75%, or 70% identical to the known, correct anchor segment sequence. Filtering criteria are used for evaluating the accuracy of the sequencing, and can be adjusted based on various parameters, e.g., the number of subreads having high-quality reads of the anchor segment. Raw target sequencing reads that meet pre-determined criteria are accepted for base-polling (see step 2 of FIG. 1).

VII. Computer Implementation

The present methods can be computer-implemented, such that at least one or more (e.g., at least 2, 3, 4, 5, 6, 7, or 8), or all steps of the method are carried out by a computer program (except wet chemical steps). The present methods can be implemented in a computer program stored on computer-readable media, such as the hard drive of a standard computer. A computer program for analyzing a nucleic acid target can include one or more of the following codes: (a) code for receiving a population of raw target sequencing reads of a nucleic acid target comprising an anchor segment and an adjacent segment, (b) code for evaluating the accuracy of sequencing of the anchor segment in different raw target sequencing reads by comparing raw target sequencing reads of the anchor segment with the known sequence of the anchor segment, (c) code for assigning a subset of the raw target sequencing reads into an accepted class based on reaching at least a threshold level of accuracy of the sequencing of the anchor segment, (d) code for polling nucleobases at a position equidistant to the anchor segment sequence in raw target sequencing reads in the accepted class to determine a consensus nucleobase, which consensus nucleobase is assigned as the first nucleobase of a nascent sequence of the adjacent segment, (e) code for assigning raw target sequencing reads having the consensus nucleobase determined in the prior polling step to remain in an accepted class and assigning raw target sequencing reads lacking the consensus nucleobase determined in the prior polling step to the rejected class, (f) code for optionally reassigning a raw target sequencing read from the rejected class to the accepted class by scoring similarity of the raw target sequencing read to the nascent sequence and reintroducing the raw target sequencing read if the sequence similarity reaches at least a threshold level of similarity, and code for repeating steps coded in (d), (e) and optionally (f), except that a repetition polls a position adjacent the position poled in the previous polling step for raw target sequencing reads having the consensus nucleobase polled in the previous step or in the case of a raw target sequencing read reassigned from the rejected class to the accepted class and not polled in the previous polling step or if polled not having the consensus nucleobase in the previous polling step, the polling polls a position adjacent the position aligned with the last nucleobase of the nascent sequence to determine a consensus nucleobase, and the consensus nucleobases determined in successive repetitions are assigned as successive nucleobases in the nascent sequence of the adjacent segment. A computer program for analyzing a nucleic acid target can also include one or more of the following codes: code for receiving a population of raw target sequences of a nucleic acid target comprising an adapter segment and an adjacent segment, code for evaluating the accuracy of sequencing of the adapter segment in different raw target sequences by raw target sequencing reads of the anchor segment with the known correct sequence of the anchor segment, code for assigning a subset of the raw target sequences into an accepted class based on the accuracy of sequencing of the adapter segment in the raw target sequences, code for aligning at least some of the raw target sequences from the accepted class, code for determining a sequence of at least part of the adjacent segment from the aligned sequences, and a computer-readable storage medium comprising the codes.

The present methods can be implemented in a system (e.g., a data processing system) for analyzing a nucleic acid target. The system can also include a processor, a system bus, a memory coupled to the system bus, wherein the processor is coupled to the system bus for one or more of the following: (a) receiving a population of raw target sequencing reads of a nucleic acid target comprising an anchor segment and an adjacent segment, (b) evaluating the accuracy of sequencing of the anchor segment in different raw target sequencing reads by comparing raw target sequencing reads of the anchor segment with the known sequence of the anchor segment, (c) assigning a subset of the raw target sequencing reads into an accepted class based on reaching at least a threshold level of accuracy of the sequencing of the anchor segment, (d) polling nucleobases at a position equidistant to the anchor segment sequence in raw target sequencing reads in the accepted class to determine a consensus nucleobase, which consensus nucleobase is assigned as the first nucleobase of a nascent sequence of the adjacent segment, (e) assigning raw target sequencing reads having the consensus nucleobase determined in the prior polling step to remain in an accepted class and assigning raw target sequencing reads lacking the consensus nucleobase determined in the prior polling step to the rejected class, (f) optionally reassigning a raw target sequencing read from the rejected class to the accepted class by scoring similarity of the raw target sequencing read to the nascent sequence and reintroducing the raw target sequencing read if the sequence similarity reaches at least a threshold level of similarity, and repeating steps (d), (e) and optionally (f), except that a repetition polls a position adjacent the position poled in the previous polling step for raw target sequencing reads having the consensus nucleobase polled in the previous step or in the case of a raw target sequencing read reassigned from the rejected class to the accepted class and not polled in the previous polling step or if polled not having the consensus nucleobase in the previous polling step, the polling polls a position adjacent the position aligned with the last nucleobase of the nascent sequence to determine a consensus nucleobase, and the consensus nucleobases determined in successive repetitions are assigned as successive nucleobases in the nascent sequence of the adjacent segment. The system can also include a processor, a system bus, a memory coupled to the system bus, wherein the processor is coupled to the system bus for one or more of the following: receiving a population of raw target sequences of a nucleic acid target comprising an adapter segment and an adjacent segment, evaluating the accuracy of sequencing of the adapter segment in different raw target sequences by comparing raw target sequencing reads of the anchor segment with the known correct sequence for the anchor segment, assigning a subset of the raw target sequences into an accepted class based on the accuracy of sequencing of the adapter segment in the raw target sequences, aligning at least some of the raw target sequences from the accepted class, and determining a sequence of at least part of the adjacent segment from the aligned sequences.

Various steps of the present methods can utilize information and/or programs and generate results that are stored on computer-readable media (e.g., hard drive, auxiliary memory, external memory, server; database, portable memory device (e.g., CD-R, DVD, ZIP disk, flash memory cards), and the like. For example, information used for and results generated by the methods that can be stored on computer-readable media include raw target sequencing reads of a nucleic acid target, the sequence of an anchor segment, the accepted class, the rejected class, the nascent sequence of the adjacent segment, the threshold level of similarity, the threshold level of accuracy of the sequencing the anchor segment, and one or more consensus nucleobase(s). Information used for and results generated by the methods that can be stored on computer-readable media also include raw target sequences of a nucleic acid target, the adapter segments, the accepted class, the partially or fully determined sequences of the unknown segments (i.e., the nucleobases in the adjacent segment adjacent the adapter segment), the discarded raw target sequences, the discarded raw target sequences reassigned to the accepted class, the sequence variations at each position.

The present invention also includes an article of manufacture for analyzing a nucleic acid target that includes a machine-readable medium containing one or more programs which when executed implement the steps of the present methods.

Figure 2:
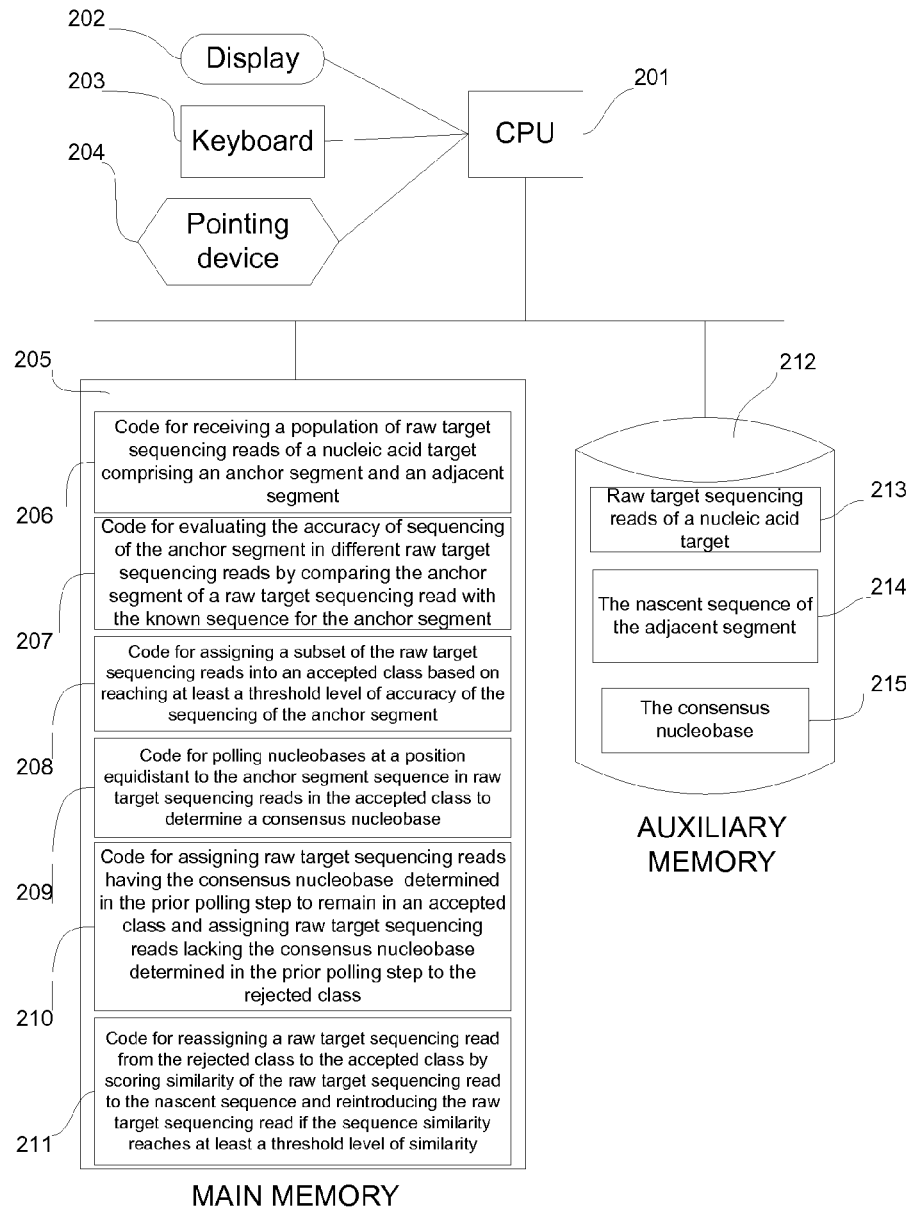
FIG. 2 shows a configuration of a device for analyzing a nucleic acid target.
Figure 4A:
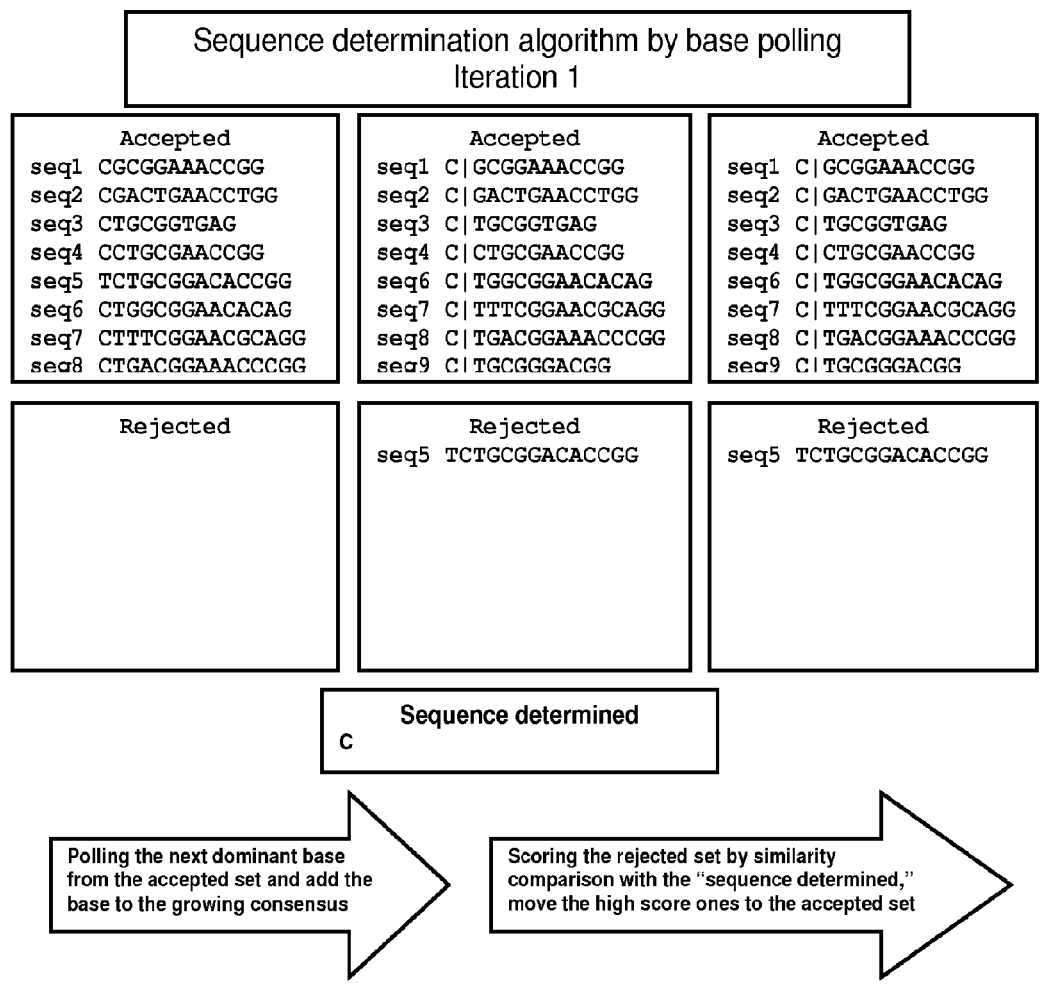
FIGS. 4A-D show determining a consensus sequence by nucleobase polling.
Figure 4B:
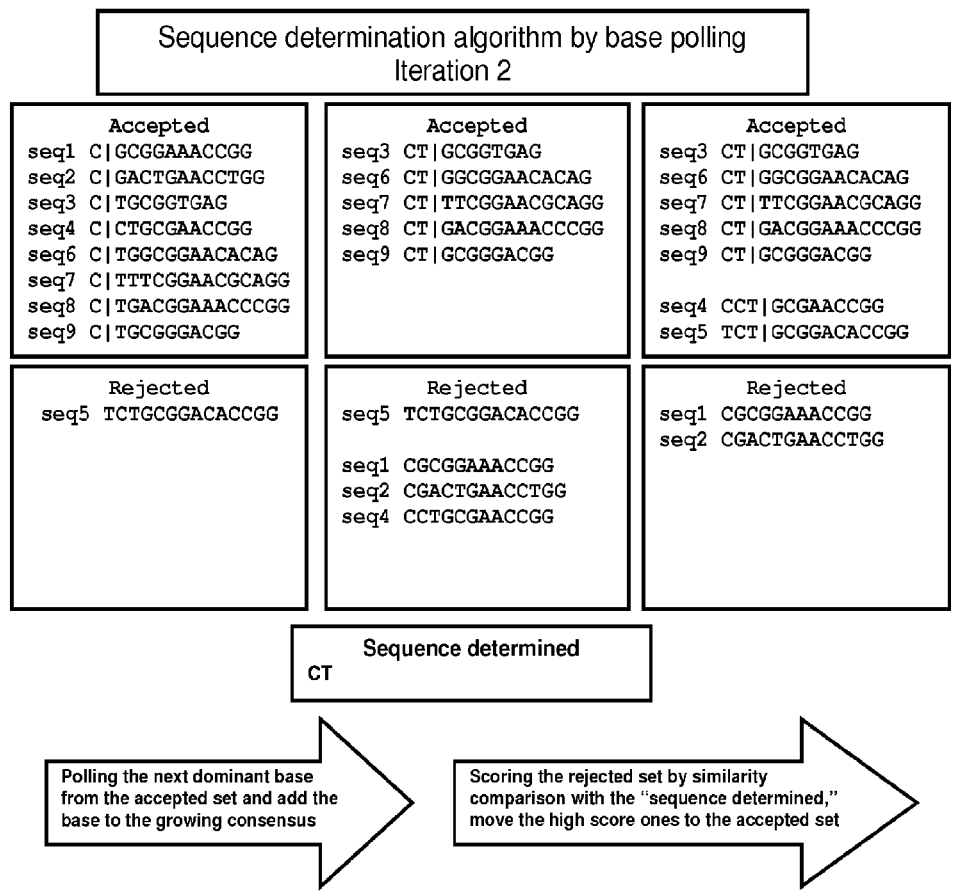
Figure 4C:
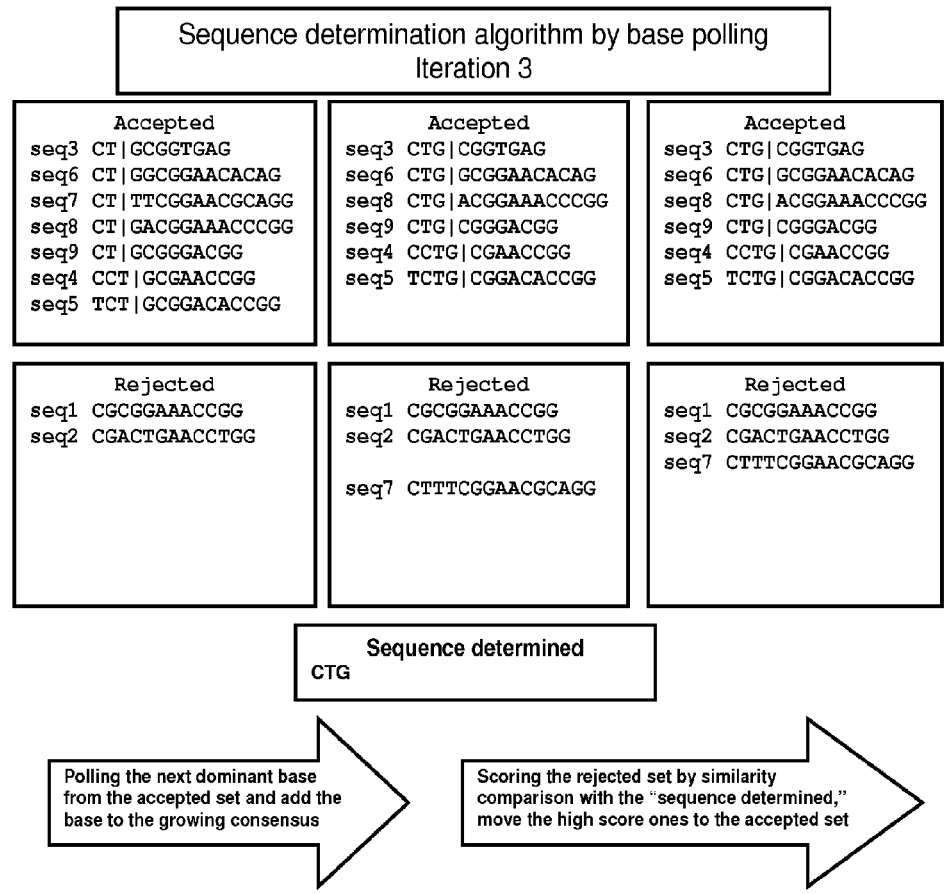
Figure 4D:
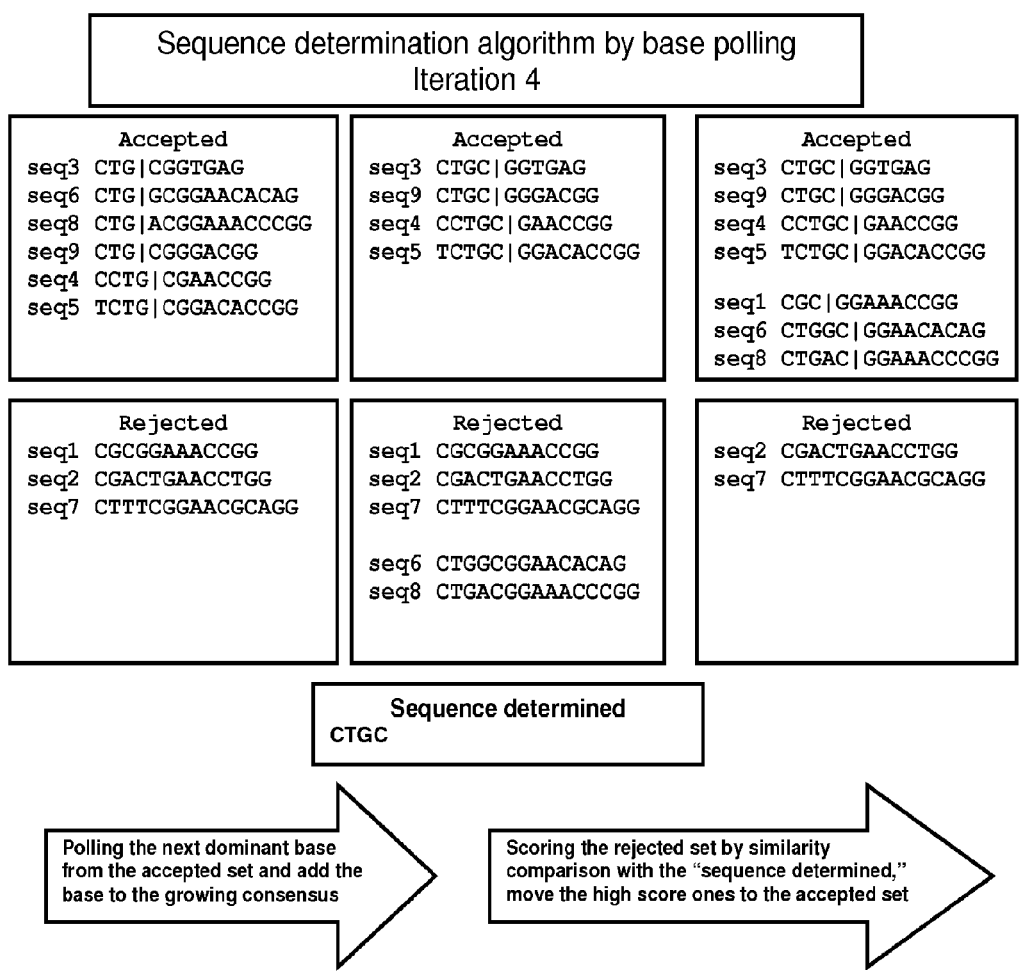

FIG. 2 is a block diagram showing a representative example of a configuration of a device for analyzing a nucleic acid target in which various aspects of the invention may be embodied. The invention can be implemented in hardware and/or software. For example, different aspects of the invention can be implemented in either client-side logic or server-side logic. The invention or components thereof can be embodied in a fixed media program component containing logic instructions and/or data that when loaded into an appropriately configured computing device cause that device to perform according to the invention. A fixed media containing logic instructions can be delivered to a viewer on a fixed media for physically loading into a viewer's computer or a fixed media containing logic instructions may reside on a remote server that a viewer accesses through a communication medium in order to download a program component.

FIG. 2 shows an information appliance (or digital device) that may be understood as a logical apparatus that can read information (e.g., instructions and/or data) from auxiliary memory 212, which may reside within the device or may be connected to the device via, e.g., a network port or external drive. Auxiliary memory 212 can reside on any type of memory storage device (e.g., a server or media such as a CD or floppy drive), and can optionally comprise multiple auxiliary memory devices, e.g., for separate storage of raw target sequences, determined sequences of the segments adjacent the adapter sequence, sequence variations information, and/or other information. The device can thereafter use that information to direct server or client logic to embody aspects of the invention.

One exemplary type of logical apparatus is a computer system as illustrated in FIG. 2, containing a CPU 201 for performing calculations, a display 202 for displaying an interface, a keyboard 203, and a pointing device 204, and further comprises a main memory 205 storing various programs and a storage device 212 that can store the raw target sequencing reads of a nucleic acid target 213 and the nascent sequence of the adjacent segment 214 and the consensus nucleobase 215. The device is not limited to a personal computer, but can be any information appliance for interacting with a remote data application, and can include such devices as, for example, a digitally enabled television, cell phone, or personal digital assistant. Information residing in the main memory 205 and the auxiliary memory 212 can be used to program such a system and can represent a disk-type optical or magnetic media, magnetic tape, solid state dynamic or static memory, or the like. For example, the invention may be embodied in whole or in part as software recorded on this fixed media. The various programs stored on the main memory can include a program to receive a population of raw target sequences of a nucleic acid target, a program 206 to receive a population of raw target sequencing reads of a nucleic acid target comprising an anchor segment and an adjacent segment, a program 207 to evaluate the accuracy of sequencing of the anchor segment in different raw target sequencing reads by comparing the anchor segment of a raw target sequencing read with the known sequence for the anchor segment, a program 208 to assign a subset of the raw target sequencing reads into an accepted class based on reaching at least a threshold level of accuracy of the sequencing of the anchor segment, a program 209 to poll nucleobases at a position equidistant to the anchor segment sequence in raw target sequencing reads in the accepted class to determine a consensus nucleobase, a program 210 to assign raw target sequencing reads having the consensus nucleobase determined in the prior polling step to remain in an accepted class and assigning raw target sequencing reads lacking the consensus nucleobase determined in the prior polling step to the rejected class, and a program 211 to reassign a raw target sequencing read from the rejected class to the accepted class by scoring similarity of the raw target sequencing read to the nascent sequence and reintroducing the raw target sequencing read if the sequence similarity reaches at least a threshold level of similarity. The lines connecting CPU 201, main memory 205, and auxiliary memory 212 can be any type of communication connection.

Raw target sequences and parameters required for the present methods can be specified by the display 202 (also referred to as a "screen"), the keyboard 203, and the pointing device 204. The CPU 201 can then execute a program stored in the main memory 205 and the sequence of a segment adjacent the adapter sequence including sequence variations, if present, can be determined by the present methods. The raw target sequencing reads of a nucleic acid target 213 can be read from the storage device 212. The output result of the nascent sequence of the adjacent segment 214 and the consensus nucleobase 215 can be stored into the storage devices 212. The progress of this processing can be displayed on the display 202. After completing this processing, the result of the processing can be also displayed on the display 202, saved to an additional storage device (e.g., ZIP disk, CD-R, DVD, floppy disk, flash memory card), or displayed and/or saved in hard copy (e.g., on paper). The result of the processing can be stored or displayed in whole or in part, as determined by the user.

VIII. Applications

The nucleic acid target or adjacent segment thereof can be derived from any of a number of sources, for example, viruses, prokaryotes, or eukaryotes (e.g., plants, fungi, and animals). These sources can include biological samples including patient and environmental samples (agricultural, water, soil), research samples, and industrial samples. A biological sample is a composition or mixture in which a nucleic acid molecule of interest may be present, including plant or animal materials, waste materials, materials for forensic analysis, environmental samples, and the like. A biological sample includes any tissue, cell, or extract derived from a living or dead organism which may contain a target nucleic acid, e.g., peripheral blood, bone marrow, plasma, serum, biopsy tissue including lymph nodes, respiratory tissue or exudates, gastrointestinal tissue, urine, feces, semen, or other body fluids. Samples of particular interest are patient tissue samples (including body fluids) from a human or an animal having or suspected of having a disease or condition, particularly infection by a virus. The nucleic acid target of interest in a patient sample can be from a pathogenic microorganism, such as a virus, bacteria or fungus, or can be endogenous to a patient, or both types of target can be of interest. Other samples of interest include industrial samples, such as for water testing, food testing, contamination control, and the like. Sample components may include nucleic acids to be sequenced and other nucleic acids, and other materials such as salts, acids, bases, detergents, proteins, carbohydrates, lipids and other organic or inorganic materials.

Nucleic acid targets or adjacent segments thereof can be isolated from samples using any of a variety of conventional procedures, for example target capture using a target-capture oligomer and a solid support (e.g., U.S. Pat. No. 6,110,678, EP 1778867, WO 2008/016988 & WO 2009/140374), the Applied Biosystems ABI Prism™ 6100 Nucleic Acid Prep-Station, and the ABI Prism™ 6700 Automated Nucleic Acid Workstation, Boom et al., U.S. Pat. No. 5,234,809, or mirVana RNA isolation kit (Ambion). Nucleic acids can be cut or sheared prior to analysis, including the use of such procedures as mechanical force, sonication, restriction endonuclease cleavage, or other conventional methods to produce nucleic acid targets or adjacent segments from which nucleic acid targets can be formed.

The nucleic acid target or adjacent segment thereof can be DNA (genomic or cDNA), RNA (e.g., viral RNA, micro RNA, mRNA, cRNA, rRNA, hnRNA, transfer RNA, siRNA), and can comprise nucleic acid analogs or other nucleic acid mimics subjectable to sequence determination. The nucleic acid target or adjacent segment thereof can also be fragmented genomic DNA (gDNA), micro RNAs (miR-NAs) or other short RNAs, or a short target nucleic acid is a short DNA molecule derived from a degraded source, such as can be found in for example forensics samples (see for example Butler, 2001, Forensic DNA Typing: Biology and Technology Behind STR Markers). The target can be methylated, non-methylated, or both. The target can be bisulfite-treated and have non-methylated cytosines converted to uracil.

A target nucleic acid can be synthetic or naturally occurring. Reference to a nucleic acid target can mean the nucleic acid target itself or s surrogates thereof, for example amplification products.

The present methods can be used in various applications, for example, de novo sequencing, DNA fingerprinting, polymorphism identification (e.g., SNPs) or other nucleic acid analysis. One application is determining the sequences of a heterogeneous population of variant nucleic acid molecules such as variant nucleic acid molecules of a same virus (e.g., HIV or HCV). Some examples of viruses that can be detected include HIV, hepatitis (A, B, or C), herpes virus (e.g., VZV, HSV-1, HAV-6, HSV-II, CMV, and Epstein Barr virus), adenovirus, XMRV, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, MLV-related Virus, papillomavirus, molluscum virus, poliovirus, rabies virus, JC virus and arboviral encephalitis virus.

Analysis of viral nucleic acids is particularly useful for analyzing drug resistance and the emergence of drug resistant viral strains presenting as minor variants in a virus population. Viruses mutate rapidly so that a patient is often infected with a heterogeneous population of viral nucleic acids, which changes over time. Some of the mutations differentiating species of the heterogeneous population may be associated with resistance to a drug that the patient has been treated with or may be treated with in the future. Deconvolution of the population to detect individual variants allows detection of drug resistant mutations and their change over time, thus allowing treatment regimes to be customized to take into account the drug resistance of strains infecting a particular patient. Because drug-resistant or other mutations may present as only a small proportion of viral nucleic acid molecules, sequencing of a large number of molecules in the viral nucleic population may be required to provide a high likelihood of identifying all drug resistant mutations or at least all, whose representation as a percentage of the total viral nucleic acid population exceeds a threshold.

The present methods can also be used for detecting SNP and somatic mutations. For example, the methods can be used to detect and characterize rare variants and identify unknown causative mutations in human diseases. The improved detection of rare sequence variants by the methods of the invention can also be applied to the discovery of novel somatic mutations, e.g., in cancers. Comprehensive genomic analysis of a variety of cancers can be performed, including acute myeloid leukemia, lung cancer, and melanoma. The present methods can be used to detect expression products of specific alleles, haplotype analysis and phasing of multiple SNPs within chromosomes, and copy number variation of DNA segments.

Human nucleic acids are useful for diagnosing diseases or susceptibility towards disease (e.g., cancer gene fusions, BRACA-1 or BRAC-2, p53, CFTR, cytochromes P450), for genotyping (e.g., forensic identification, paternity testing, heterozygous carrier of a gene that acts when homozygous, HLA typing), determining drug efficacy on an individual (e.g., companion diagnostics) and other uses. Sequence variations information obtained from the present methods can be used to treat the subjects differentially. For example, samples from members of the patient population can be sequenced. The sequencing can provide information about a pathogenic microorganism infecting a patient (for example, type of organism and/or drug resistance). The sequencing can alternatively or additionally provide information about a patient gene associated with genetic disease, susceptibility or response to infection or response to treatment. Different members of the patient population can receive different treatment regimes (including no treatment) depending on the determined sequence for the sample from each member.

The present methods can also be used for epigenetics studies. For example, the methods can be used for detecting DNA methylation, such as aberrant methylation associate with various diseases such as cancers. The methods can also be used to select patients for demethylation therapies and to monitor the therapeutic response to demethylation agents.

The present methods can also be used for RNA analysis. Analysis of rRNA is particularly useful for detecting and/or typing pathogenic bacteria. Examples of such bacteria include chlamydia, rickettsial bacteria, mycobacteria, staphylococci, treptocci, pneumonococci, meningococci and conococci, klebsiella, proteus, serratia, pseudomonas, legionella, diphtheria, salmonella, bacilli, cholera, tetanus, botulism, anthrax, plague, leptospirosis, Lymes disease bacteria, streptococci, or neisseria. Ribosomal RNAs in these various organisms typically have conserved sequences and variant sequences that are unique to one or a few different organisms. A conserved sequence can be used to identify an rRNA and a variant sequence to identity an organism of which the variant sequence is characteristic. For example, U.S. Pat. Nos. 7,226,739 and 5,541,308 disclose conserved and variable rRNA sequences in a plurality of bacteria. Similarly, many diseases are associated with aberrant mRNA expression. The present methods can be used for transcriptome analysis (RNA-seq) such as small RNA mapping and transcriptome mapping.

Nucleic acids having sequences determined by present methods can be synthesized by conventional methods, including solid state synthesis and primer extension.

EXAMPLES

Example 1

Sequence Determination by Base-polling

FIGS. 4A-D provides an illustrative example of sequence determination using the base-polling methods as described in the present invention. The example illustrates the sequence determination algorithm using an initial set of 9 raw target sequences (SEQ ID NOs:1-9). Raw target sequences that meet certain criteria (e.g., sequences being polled or reassigned) were placed into an "Accepted" class, and those that fail the same criteria were placed into a "Rejected" class. For illustration purposes, a total of four iterations of base-polling are provided for determining a sequence of four nucleotides.

Iteration 1

Raw target sequences 1-9 were chosen based on the quality of an adapter sequence (not shown), and aligned over the region of the adapter sequence. These sequences were placed into the accepted class and were used as the initial population of raw target sequences for base-polling. As illustrated in Iteration 1, the dominant nucleobase at the first nucleobase position is nucleotide C. The raw target sequences were accordingly polled and the first nucleobase of the sequence determined is C. Sequences 1-4, and 6-9, having C as the first base, remain in the accepted class. Sequence 5, having a T at the first base, were placed in the rejected class. The vertical bar in the accepted set indicates that the sequence segment before the bar is the sequence determined so far. The nucleobase after the vertical bar would be the next nucleobase for polling.

The sequences in the rejected class (e.g., sequence 5) were then compared with the determined sequence (e.g., a sequence comprising the first nucleobase C). In Iteration 1, sequence 5 was not reassigned into the accepted class because the first nucleobase of in sequence 5 is not the first nucleobase determined in the polling step, and there is not enough sequence similarity between the first nucleobase determined in the polling step and the first nucleobase of in sequence 5.

Iteration 2

The polling action at the second nucleobase generated the second polled base, T. Sequences 1, 2, and 4 were placed into the rejected class because the second nucleobase in these sequences is not T. Sequence 5 in the rejected class is carried over from the last iteration.

The sequences in the rejected class were then compared with the determined sequence CT. Both the first (C) and the second nucleobase (T) were found in sequences 4 and 5, even though they appear at the second and third positions by sequential numbering due to a single-base insertion. Therefore, sequence comparison found sequences 4 and 5 as good matches with the determined sequence CT. These two sequences were reassigned to the accepted set, leaving only sequences 1 and 2 in the rejected set.

Iteration 3

The polling action at the third nucleobase generated the third polled base, G. Sequence 7 was placed into the rejected class because the third nucleobase in sequence 7 is not G. All three sequences (1, 2, and 7) were not found to be similar to the determined sequence CTG. Sequences 1, 2, and 7 were not reassigned into the accepted class because there is not enough sequence similarity between the determined sequence CTG and these sequences.

Iteration 4

The polling action generated the fourth polled base, C. Sequences 6 and 8 were placed into the rejected class because the fourth nucleobase in these sequences is not C.

The sequences in the rejected class were then compared with the determined sequence CTGC. The fourth nucleobase C was found in these sequences, even though it appears at the third position of sequence 1 by sequential numbering due to a single-base deletion, and at the fifth positions of sequences 6 and 8 by sequential numbering due to a single-base insertion. These three sequences were reassigned to the accepted set because their overall sequences were highly similar to the consensus sequence.

Example 2

The Sample Sequence, Sequencing and the Primary Analysis Data

The sample sequenced was a region in the HCV 5' UTR of 164 base pair long that is listed below:

(SEQ ID NO: 10)
CTGCGGAACCGGTGAGTACACCGGAATTGCCAGGACGACCGGGTCCTTTC

GTGGATAAACCCGCTCAATGCCTGGAGATTTGGGCGTGCCCCCGCAAGAC

TGCTAGCCGAGTAGTGTTGGGTCGCGAAAGGCCTTGTGGTACTGCCTGAT

AGGGTGCTTGCGAG

The PacBio's standard sample preparation and SMRT-™Bell preparation methods were used.

The sequencing was carried out on a PacBio RS sequencer using the following protocols.

TABLE 1

Protocols used in sequencing and primary analyses

| Protocol | RS_CircCons_HCv1a3bUTR.1 |
|---|---|
| Collection protocol | Standard Seq 2-Set v1 |
| Primary protocol | BasecallerV1 |

There are two videos of 45 minutes long. Data from the two videos are combined for the subsequent analyses.

TABLE 2

Per video sequencing statistics

|  | Video 1 | Video 2 |
|---|---|---|
| Reads of productivity = 0 | 2031 (2.7%) | 5033 (6.7%) |
| Reads of productivity = 1 | 44625 (59.38%) | 44098 (58.69%) |
| Reads of productivity >1 | 28497 (37.92%) | 26008 (34.61%) |
| Mean Quality Score (productivity = 1) | 0.79 | 0.8 |
| Mean Read Length (productivity = 1) | 1398.67 | 1569.75 |
| Pass Filter | 59.73% | 58.85% |
| Active ZMWs | 97.30% | 93.30% |
| IPD | 0.22 | 0.26 |
| Poly. Speed | 2.21 | 2.05 |

TABLE 3

The combined sequencing statistics are listed below.

| Total Bases | 391035620 |
|---|---|
| Total Reads | 150292 |
| Total Reads of productivity = 0 | 7064 |
| Total Reads of productivity = 1 | 88723 |
| Total Reads of productivity >1 | 54505 |
| Total Active ZMWs | 143228 |
| Mean Quality Score (productivity = 1) | 0.79 |
| Mean Read Length (productivity = 1) | 1483.7 |

From the large number of files generated in PacBio's primary analysis, we only used the raw FastA file for all the ZMWs as our input.

On the PacBio platform, the sequenced molecule is in a SMRT™Bell format with a double stranded insert and a hairpin adapter at each ends. That produces a read of alternating forwarding and reversed strand of the insert interspersed with the adapter sequence.

The adapter sequence is (SEQ ID NO: 11)
ATCTCTCTCAACAACAACAACGGAGGAGGAGGAAAAGAGAGAGAT

Example 3

The Workflow of the Polling Algorithm (1) Subread Extraction:
(a) Identify the adapter sequences and generate the subreads from each read.
(b) This process also offers some local sequencing quality information that can be used to further filter out low quality regions. That includes the spatial quality (the particular ZMW) and the temporal quality (the adjacent bases have a higher probability to be more similar than distant ones).
(c) Filter the subread set using certain criteria.

(2) Run Polling Algorithm:
(a) Assign all subreads with good adapter quality and sufficient length to the initial accepted set.
(b) A single base polling step: (i) Poll the most dominant base from the next base (the base immediately after the consensus matched segment of the subread in the accepted set, and initially it is the first base of the subread) of all the subreads in the accepted set. (ii) Assign the dominant base to be the next base in the growing consensus; (iii) Move the subreads with different bases to the rejected set (the newly rejected); (iv) Use the Overlap Matching pairwise-alignment algorithm that does not penalize overhanging ends to score the subreads in the rejected set with the consensus sequence. (v) Return the good matches to the accepted set (the returned).
(c) Repeat step b until a stop condition is met. The stop condition can be a pre-defined consensus length, the minimum size of the accepted set at that step, or a significant increase of the terminated subread at that step.

(3) After finishing one consensus, step 2 can be repeated with all the subreads in the rejected set. Iterate through to generate more consensuses until there is not enough subreads left.

Example 4

The Identification of the Adapters, Generation of Subreads and Quality Scores

From the primary data, the FastA files, all the adapter sequences in the raw sequence from each ZMW were identified using the algorithm described herein. We used the Overlap Matching alignment to align adapter sequence with the raw read. A score was computed from the alignment as $$\text{Score} = \frac{\text{Sum of mismatches and indels}}{\text{The length of the matched portion of the adapter sequence}}$$

The score served as the quality score of the adapter. The alignment generated two unmatched fragments, occasionally one fragment from the read. The process was repeated recursively over the newly generated fragment until no more adapter matches could be found for the cutoff value 0.2 per base. In other words, for an alignment with a full-length adapter of 45 bases, the maximum allowed differences, mismatches and indels, was nine. The lower bound for the length of the matched portion of the adapter sequence was also set to be 24. Furthermore, the acceptable subreads were limited to the length between 60%-140% of the length of the amplicon that was 98-230, and there must be at least three subreads in a read.

124343 (83%) raw reads were removed due to short inserts (possibly adapter dimers) and poor quality adapters from further analyses. In the remaining 24836 reads, 179001 subreads were generated according to the adapter locations.

The matched sequences are normally not perfectly matched to the adapter sequence. For example, there can be some long regions without a good match indicating the quality was too poor for the adapter to be matched. Below is an example of removed low quality raw read. Notice the short length and long stretches like "AAAAAAAAAAAAAAAA (SEQ ID NO:12)".

>m110510_124258_sherri_c100084032555500001215005706031134_s1_p0/54
(SEQ ID NO: 13)
TGCAGCAGGGCGGCTGCTGAGAGTGATGGTCGCGACACTTGACTCGCAGGGTGACAAGAAAG

CGCCTCTCCCCCATTGCCTCTTGTAAAATCCACGAGAACAAGACCGCCATCCGACCCAAACA

AAAACGACACTCAAAAAACAGCCACCAAAAAAACAAGCACAGAAGCAACCAAAAGAAACCAC

CAACCACACCCAGGAAAAAAAAAACAAAAAAAAACAAAAAAAAACAAAAAAAAAACCACAC

CCACACATCATCTACAAACAACAAAAAAGACCGAAAAAAAAAAAAGATCGGACCCACCACCA

ATAACCTATACAACCACTTAAGAACGCGCAGCCACCCCCATCCACGAACAAAAAACACAACA

GCCAAAGAACACCAAAAAAAAAAACAAAAAAAAAAAAAAAAAAAAAAAAAAAAAAAAA

TGGACGTGCTTGCCGAATGCGCGGTGGCGCTT

Five sequences with the matched portion to the adapter sequence indicated in lower case are listed below. The sequence names are their ZMW IDs. The matched sequences (lower case) are normally not perfectly matched to the adapter sequence. In addition, there are some long regions without a good match indicating the quality was too poor for the adapter to be matched. For example, in the first sequence (ZMW ID 7), the first two segments (spilt by the adapters) are quite long comparing to later ones. In this sequence, the subread should be about 164 base pair long.

>ZMW ID 7
(SEQ ID NO: 14)
GGCCGCTCTGTCCAGCGATTCGCCGTGTTACCGTAATCGCTCAAGGCAGCCCTCA

CGCTTCAGCGCGGTGTCTGTAGGATAGATCTTTCCGAGCGACAGAGTGGACGGC

CCTCGAAGAGGACTGGCCCGGCCTCGAGCCTGAGATCTGCGTTAATGGCTCCCG

ATAGAGTCCGTCGGCTAGTGGTTGGAGCTCTCGCGCGCTCCTAATAACTCGCTGC

GCTTCCTCGCAGCAGCAATCTACGCGTCCACTCTTCAGCTCAGACTAACAACCTC

GCGAAGACGGAAGGAGAAGAGGCAGTATAGGGATGAGGTCATCGCGAAGGCCG

CATCTATGCGCGAGGAAACCGGTGAGTAACACCGCGGGTGCATCCGTGTATTGT

ATAGATCTCTGTGCCGAGCACCACAACAACGGAAGGGTCGCCGTTACGGGAAAA

GCAGAAACGAGAACTCGGATAAACCTTTATCTTGGCTCATTCGCACGGCTCTCGG

GACCTGCCTCTCGAGATAGAGGAATATGCGGTAGACGCGCTCGCGAAAGGACCT

CAGCGGCATTCTTTTCTTACACATACAGCTCTTTTTATTCTGCGCCACGCCGACAG

GTCTCCCCCAGATCCCTTCTTCAACCTAACCAGAGCTACAAGCTCTTGGCGGGGA

AGGCGGCGGCGACGCGCATCTGTAGATACGCGGCGGCGGTGTATAGTTCTCCGA

CGCGGTACGCGGTCACTCCTGGCATGCTCGCAAGGGTGTAACTTAGATAGCTCC

GGGTTTCCCCCGACTTCCCCAGGCCTGGCAGTAGGAGTAGGCGTCCTTTGCGTTA

GATTCTTCGTTTCTGCCTACAAACAAACCACAAACACGCCAGATCGAGGAATGT

GAGGAACCACGAGCCGCAAGAACTCCATCCGCACGCGCCTACACCCGAGTACTA

TTTGGTTCGGGGCGTGGGTGACCCATTCCACCGGCCTGTGATCGACAGGACCCCT

ATAGGCATCTATACTCTCGGAGCCTGGATATCGTACGGTGGCTTTGGCGGGGGTC

GGACCGGCATATATCTCTCCATGCGTCATCTTAGAGCACAGGCAGTATTTCGGTA

CACAGAAAAAGGACGAGACAGGACGAGTCGTCCTGTGCAATTCTGGCTCGTAGC

TCACACCGGTCAGTCCGCAGACTGCTCTCTCAACCAAACACGAGACGCAGGTAG

GTTATGGCCAAAAGGAAGACCGAGGATTTCAAACTCTCTGGCCGGAACCGCGTG

GGACAGTTCACCTTTCGGCGCACGCCAATCTGGCAGTGCTATTGTCGCAGGCGCC

CGGGGTTCATCTAAACGGATCGCTCGATATCTTAAATCCTCGCGCTACAATGCCT

TCCGGTGGAATGTAACTTCACCGTCCTTCTGGGGCCAGATAGCCCCTCACCGCCA

```
AGAACCAACCAACGAGGGAGGAGAAAGAACTGGACATTTACCCAGACCGTGTG

GATGTGCATCCGCGACCGGCTTAGATGGTCCTCAAGGCTGAGCCTGGATTCCTGT

GTCGGTGCTTAATCGCGCCGCTCACATTCCTTCTCGATATCTGGAGACAACAGGA

CGGAGGTAGGAGGGAAAAGAGCGAGGGAAGGTCCCTCGCCAAGCACCCTATCA

GGCAGTACCACAGGCCTTTCGCGACCCAACACTACTTCGGGCAAGACTTCTAAC

GCAGTACCTTGAGTGACGGGGCACGGTCCAAATCTCCCAGGCATTGAGCGGGT

ATCCACGAAAAAGGACCCGGTCGTCCTGGCAATTTCCGGTGTCTCACCGGTTCCG

CAGAatcttctctcaaacaacaacaacggaggaggaggaaatcggcaggagaAGACGTGCGTGTTTACACG

GGTGTGTATTACACACCGGAATTGCCAGGACGGACCCTGGTCCTTGTCGGTGAGT

GAATACCTTTCGGCGTCTACACACTCGTCACTCGAGCGAGAATCTAAACTAGGC

AGAGGAAAGCGTAAGGAAGAGCTCTCCAAAAGCACCTTCCTGCACTCCGCAACG

AACGTGCTCGCTTGTTGTCGCAGCTCCTGGGAACCACTCGCCGAAGGCCTTCGGT

GGGTACTCTCTTAGGTCAGGTGTGTCGCGGTTGGGAGGATCCCCTCTCAAACATC

CACATTTGAGGCGTTTTTTAATTCACGGAAAAGGACCCGTCGGTTCCACCCAAA

TTCCGGGTGTACTCACCGGTCCCCAGATTCTTCTATTCAACAAAAAACGAGAGGA

ACCAACGGAGGAGGAGGAAAAGAGAGAAGATCTCGCAAGCACCCTAATCAGAG

CAAGGGATACGGCGAGGAACCTACTTGGCCTTTCCGCGGCCGAACCCGTGGAGT

TAACCCGAATTCAACACCTAGGACCTGGCGGCTAAGCAGTCTTGCGGGGCGCAT

CGCCAGATACTACCACGCGCCTTGCAACGGTTCTCACGAAGGAGGACCCGGTCG

GTCCTGGGCAATTCCGGTCGTACTCACGCCGAGTGCACGCGATACTCAATGCCGT

CAACGCAACAAGCAGAACGGAGGCCAGGGACCGCCGTTTTGAGTTAGATGAGA

CGAGGAATCTGCGGACCGGTGAGTACACCGCATAATTCGTGGGCCATGGATCGA

CACGCTCAAGGCAAGCATCTGATTCGTGGAATGGATAAAAAGAAAACCTTCTTC

CGCAACGCTCAACTGCCTGGCAGATTTGGCTGACGTTCAGGCCCCCAGCTCGCAC

AGACACTGCCTTTTCGCGACGCGTACGTCTACCGAGTAGTCGTTGCGAGGCGTTC

TTGGTCGGCCGAAGGCCCCAAACTCCAGGGTTGCTCGGTTGGAAGCCTGTTTTAT

CCACCGAAGGAACCGCCGTCGGTCCTGCATGCTCCGTGATAGGCTCACGCGCTTT

CCTCGGGCATGTATGGATCTTTCTCCATACACAAAGCAACAAGCGGAGAGGCAG

GGAAAGAGAGAGCTAATCCCCGCAAGCACACCGCTATGCGGCAGTTGACGCAA

GAACAGAGAGACAGCGGGCCTTCTCGCTTGGACGCCAATTCACACTCAGCCTCG

GCTAGCAAGTCTTGCGGGGCACGCCACCATCTCAGGTGCTTGCATTTGAGCGGTC

TGATTCCCACTGTATAGCGACCCGCGCTCGTCCTGGGCAATTCCGTGTACCCCAC

CGGTTCCGCAGatctctctcaaccaacaacaaacggaggaggcaggggaaaagagagagagatGCTGAGGCGGA

AGCCGGTGAGTAGGCCACCGGAATTGCCAGGACGACGCCGGTCCTTTCGTGGAT

AAAACCCGCTCAATGCCTGAAGTTCTGGGCGTGCCCGCAAGACTGCTAGCCGAG

TTAGTGTTGTGGTCGCGAAATGGGAGGCCTGTGGTACTCGGCCTGATAGGGTGCT

TGCGAGatctctctcaacaaacaacaacggaggagaggaggaaagagacggcaggatCCGCAAGCACCCCCTA

CTCAGGCCAGGTACGCACAAGGCGCTGTTCGCCGAACGCCCCACACCTACTCCG

GCTAGCAGTCTTGGCGGGGGGCAGCGCCCAAATCTCCAGGCATTGAGCGGGTTT

AATGCCACGAAAGGACCGCCGGTCGTCCTGGCAATTCCGCGTGTACTCAGCCGG

TTTCGCAGatctctcatcaacaacaagcaacgcgaggaggaggaaaaggagatgatCTGCGGACGCGTGAAG
```

-continued

```
TACACCGGAATTGCCAGGACGACCGGTCCTTCCTCGTGGATAAACGCCCGGCTTC

CAAATGCGCTGGCCAGATTTGGCGGCGATGGCCCGCAAGACTGCTAGCCGAGTT

AGTGTTGGGTCGCGAAGGCCTTGTGGTACTAGCCGTGAGTAGGGTGCTTGCCGA

GatctctctcccaaacaaccaacaacggaggaggaggaaaaagagagagatCCTCGGCAAGCACGCCTTATG

CAGGCCAGTACCACGAAGGCCTTCGCGACGGCGGCAACAACTACTCGGCTACAA

AGACTCTTGGGCGGGGGGGCACGGCCAAATCTCCAGGCATTGAGCGGGTTTATC

CAACGAAAGGACGCGCGGTCGTCCTGGGCAATTCCGGTGTAGCTCACGGTTTCC

GCCAGAatctgctctcaacaagcaacacggaggagggaggaaaagggggggaAAGAGAGATCTGCGGAA

CCGGTGAGTACAGCCGGAATTGCCAGGACGCAACCGGGGGTCCTTTCGTGGATA

AACCCGTCAATGCCTGGAAGAATTTGGGGGCGTGCCCCCGCAAGACTCGCTAGG

CCGAGTAGCTGTTGGGCTGCGGGCGAAAGGCCTTGTGGTATCTCGCCTGATAGG

CGTCGCCTTGGCGAGatctctgctcagcccaacagacagacggaggcagagaggaaaagagagagaATCCCT

TCGCAAGCACGCCTATCAGGCCAGTACCACAAAGGCCTTTCGCGAGCGCGTCAA

CACTAGCCTCGCTAAGCAGTCTTGGCGGGGGGCAGCCAAATCTCGCAGGCATGA

GGCGGGTTTATCCACGAAAGGACCCGGTCGTCGCTGAGCAATTCCGGGTTAGCT

CACCGGTTCCGCAGATCTCTCTCAACAACAACAAGCCACCAAACGGAGGAGGAG

GAAAGAGAGAGATCTGGCGGAACGCGTGAGTACCG

>ZMW ID 8                                                (SEQ ID NO: 15)
GGTGGAGTACAAGCCACGGAATTGGCCACCGGGACGACGCACGCAGCACGACC

CGGGTCCATTTCGTGGAATAACCCGCTCATGCCTGGAGATTTGGGCGTGCCCCCC

ACCCCGCAAGACTGCTGCCGAGTAGTGTTGGTCGCCGAAAGCGCCTTGTGGCTA

AGCCTGCCGCCCTGATCAAGCACGGGTGCTTGCGAGATTCCTCTCACAACAACA

CCACGGATGAGGAGGCCAAAAGAGCAGAACTCTCGCCAGCACCCTACTTCAAGG

CAGTACCACCAAGGCCTTCCGCGACAGCCCGCAACACCTACTCCGGCCTAGCCA

GTCTTGAAGCGGGCGGGCAAGGCGCCCAACGATCCTCCAGGGCATTGGCCGGGT

TTTATCCCACGAAAGGACTCCGGCGTGCCTGGCCCATTCCGTTGTACTCCACGCG

GCTTCCGCAGCTCCTCTCCTCCAAACAACCAACCAAAAACGAAGAGGAAGGAGG

CAAAAGAGAGAGATCATGCGGAACCAAGGTGAGTACAAACCAGAGAATATAAC

ACAAGGACAGAACCAAAAAGAAGAGAACCCATTCATAATCGATGATAACACA

AACCGCTCCACAGACATATAAAGAAGAACGCACGAACACGCGGCGCGTCGCCA

AACGCCAAGATAGCGAGTAAGCCAATAGATAAGAGAGCAAAACAAAGTCAGAC

AGAGAAGACCATAATAGAGATAACAAAAAAAAAAAAAAAAAACATAAAAGCT

GATAAGAGAAAAAAAAGATGCTACAGAGAAAATATCATCTCCATCACACAACAC

AACACAGAGAGGAAGGAAAGGAAAAGAAGAAGAGAAGATACATGCAGCACAC

TAAATCAAGAGAAAAAAACCAAAAAAAAGACAAGATAACAAAAAAAAAAAAA

AAAAAATACACACAAAAACACCAAACACACAACAAACACACACCAAACAAC

ACACAAACAAAAAAACAAACAAAAACACCAAAAAAAAAGAAAAAAAAAAAAA

ACAAAAAAACAAGACACAAACAAACAACAAAAAACCAAAACAAAAAAACAAA

AAAAAACAAAGGCCTTTCGCCAAAAGAACCACAACAACTACAAAACAGACTAG

AACAGATACCATATAAGCGGAGGAGCAAAAGCACAAATACAAAAAATACCAGG
```

```
CATATTGAAAGACAAAGGCGATAATAATAAACCACGAAAGGACCGGTCGTAAA

ACCTGGCAATTTCCGGCGTGTACTCACCGTTCCGCAGatctctcctcacccaacacaaccggacgg caggaggcaaaagagagagaGATCTGCGGAACCGCGCGTACACCGGAATTGCCAGCCGGA

CGACCGGCGTCCTTTTCGTGGACTACACCCAGCTCAATCCGCCTCTGGAGATTTG

GGCGTGCCCCCCGCCAAGGCCGGACGGACCACTGCTAGCCGAGTCAGTGTGATG

GGGCGCCTCTGGCCCTCCGGCCCTTTGGCGGGGCGGGTTTGCCTTCCGACCGTGG

ACGGGTCGCCGAAAGGCCGCCGTGTGCTCGGTCACTCCGCCGCCTGAAATAGGC

GCTGGGCTTGGGGAGATCTTCTCCTCAACGCGTCCGTCTGGCAATTCGGGTGGGC

GCCCCGGGAGCGGGAGTGACGCGCAGGAAAGAGAGAGCGCTCTGCATGCCGCC

CCTATTCCCCAGGCGAGGGCGCGACAGAGAAGGGCCGCTGTGTTCTGCTGCGGC

CACGAGCATACTGCGGCCTATGTAGTCGTGGCGGGGCGCCCAGATCTCCCAGGC

ATTGAGCGGGTTATCCACGAAGCTTATCTCCCGTCGTGGCCTTGGCCAACGCCCT

TCCGGTGTACTCATCTGGGTGACGGCGATCTCGCGCCACGCCATTATAAGAGCG

GCAGGAGGGAGACGCGCCGAGAGCATGCTGCTGGAACCGCTGAGCGCGTTAAC

AGCCGGAGTTTTCTGTGCCTAGGACGGGCTGTCGAGACCGTGGTCCTTTGTCGTC

GCTACATACCCGCTCAATGCCTTCGGAGATTGGTGGGCGTCTGCCGGCCCGCGA

AGGCACGGGCCTCTCCGGAGGTAAGCCGCTGTGGTGGGATTCGCGAAAGGGCCT

TGTGGTACTGGCCTGATAGCGCGTTTCCGCGCTTGCGCGAGCGATCTCGTCTGCG

AACATAACCAAAACGGGGAGGCGGCGGCGGAACAGAGAGAGCAGAGTCCTGCG

CGCCCCCCTCTCACCCGGTCGCGGCGCGGCGATCGATGCACCACAGGCGCCGCT

TTCGCGGCCCAACATCTCACTACTGCGCGCTAGCGCTCTGTGCGGCGGCTATACT

GTCCAAGATGCGTCCTACCGGGCAGGCCGCCGCCCGGCACCAGTCGCAGCATCC

TGGAGCCCGCGGGTTTCAGTCCACGGCAGCAGGTGGACGCCCCCGGGCTCGTGG

CCCTCGCGACTCTCCGGGTACGCACCCGGTTCCGGCAGGATCCCTCCATCAGCGC

GGGCCGGGCGCCGGCCACAACAGACGGGGCCGCGGCAGGAAGGGCCGGGACCC

AAGAAGAGAGAGATCTGCGGAACCGGTGAGTACACGGAATTGCCAGGACGACC

GGGTCCTTCGTGGATAAACGCTCGCTTCAATGCCTGGAGATTTTGGGCGTGCCCC

GAACTGCTAGCCGAGTAGTGTTGGGCTCGCGAAGCCCTTGTGGGTACTCCGCCTG

ATAGGCGTGCCTTGCGAGatctctctcaacaacaagcaagcggaggaaggagggaaaagaaaggagatCGCT

CCGGCAAGGCACCCTAATCAGGCAGTACCACGAGAGGGCCTTTCGCGACCAAGC

ACTACTCGCGCTAGCAGTCTTTGCGGGGGCACGCCAAATCCTCCGAGAGGCATC

TGAGGGCGGGTTTATTCCAACGAAAGGACCCGGTCGTCGCCTGGCAATTCCCCG

GTGTAGATCACGCGTTTCGCGGGCAGAATtctctctcacaacgacagcaacggagagagcaaaagaaga gagatCGTGGCGGAACCGGTGAGTACACCCGGAATTGGCAGGAACGACCGGTCCTT

TCGTGGATAAACCCCGTCCAATGCCGTCGGAGAATTTGGGCGTGCCCGCAAGAC

TGCTTAGGCCGAGTAGTGTTGGTCGCCGAAAGGCCTTGTTTGTGACTCGCCTGAT

AGGGTGCTTGCGGGAtgctctctccaaacaaggcacacggaggagggaggcaaaagagagagatCTTCGCA

AGCCCGAGCCTATCAAGTGGCGCAGTACCCAACAAGGCTTCGGCGAGCCCACCA

ACACTACTCGGGCTAGGCAGTCCTTGCGGGGCACGCCCAAATCCGGCAGCATTG

AGGCGGGTTTTTTTCTTTTTTAAAATCCAGGGTGCGGCTAAAGGACCCGGTCGTC

CTGGCAATCCGTGTGTACCTCCCGGTCCGCAGatctgctccaaacagacaacaacgggaggcagagg
```

-continued aaaagagagagatCTGCGGAACGTCGTGTGAGTACGAACCGGAATTGCGCAGGACGAC

CTGGTCCCTTCTTCGTGGATAGAACCCGCCTCAATGCACTGGAGATTTGGGGCGT

GGCCCGCCGCAAAGACTCCGGCTTAGCCGAGTAGATGGTTGGGTCGCGGATGCG

CGAAAGGCCTTGTGGTACCTCGCGTTTTTTTTTTATTTGTTCTTCCAA

>ZMW ID 19 (SEQ ID NO: 16)
CTTGTTGGGTCGCGCAACAGTGGGCCTGTGGTAACTGAGTTTTGTTCAGGCCTGC

ATAGGTTGTGCTGCGAGTCTCTCTCGTGAAGCAGAGACAGACGGGAGGCGGAGG

AAAAGAGACGCCGGATATGATCCGAAGTTGTTATCTGCAGCACCTATCGGCAGT

ACCACAGTGCCTTTCGCGACCCATAGCACTACTCGGCTAGCCAGTTCTGCGGGGG

CACGCCAAATCTCAGGCATTGAGCGGGTTATCCACGAAGACGGAACCCGGCGTC

TGGCAATCGGTGCTACTCCGGTTCGCAGCATCTTCTCACACAAACAACGGGGGA

GACAGGAAAGAGAGAAAGATCAATGCGAACCGGTGAGTCACACCAGGATTCGC

CAGGCGTACCGGGTCCCTTTCGTGGATAAACCCAGCTCAATGCCTGGAGATTTTG

GCGTGCCACCGCCAGACCTGCTCAGCCGAGTATGTTGGGTCGGAAAGGCCATTG

TGGTACTAGCCTGATAGGGGTGCTGTGCGAGATCTCTCTTCAACACACAACGCAG

CGAGAACGGTTAAGGTAAACGGAGAGTTCTCGGAAGCACCCTATCGGGGCAAG

TCCACAGGAGGCCCTTTTCGCGACCCCATGACACTACTCGGGGGGTCTTCGCAG

TCTTAGCCGGGGGCCGCCCAAATCTCTCAGGCATTTGGGCGGGTTTTTTTATCC

ACGAATGACCTGGCGGGCGGTCGTCTGGCAATGTCGGTGGTACTACACCGTTTCT

CGCAGAGtctctctccaacatccacacaagcggaggaggaggaaaagagaagagatCTGGCGGAGCCCGGTG

GTACTCGGAATTGCCAGGACGACCGGGGTCTTTCGTGATAAACCGCTCAATGCCT

GGAAATTTGGGCGTGCCCCCGCAAGACTGCTAGCCGAGTAGTGTTGGCGGTCGC

GAATGGCTTGTGTACTGGCCTGAATAGGGTTGCTTGCGGACGatcttcgtctcgaaacaacaa caaacggaggagggagggaaaagagagagatCGTCGCAGCACCCTATCAGCCGCAGCTACCACA

AGCCTTTCGCGACGGGCAACGACTACTTTGCGGGGAGCAGTCGTTGCGGGCCAC

GCCAATCTCGCCCAGGCATATTCGAGGCGGGTTTTATCCCGCGGAGGGAGCCCG

GTCGGTCTGGCAATTCGGTGTACTCGCACGGTTTCGCAGATCTCCTTCTCAAGCA

ACAGGGGGGGGGAACAGAGGGGAGGGAGGCAGGACCAAGAGGAGGATGAT

CCTGCGGAAACCGGTGAGTACAGCCGGGACATTGCCCAGGACGACCGCGCAGCC

GGCCGCACCGCCCCCCGGTGCGGTCCTTCTCGTGGCCGCAGACGCCCCGCCCAC

CGGCGCCCGTCAGTCCGCCCGTGCCGGAGAAGTATTGGGATGGGCGTGCCGCCC

GCAAGACGTGCTCACGCCGAAGTAGTTGTGTTGGTGGCGCTGGAGGGTACTTGT

CGGCGAAAGGCGCTTTCGGGTAGCTGCCTGATAGGCCGTGCTTGGAGatctcctctcaac aacaacaacggaggccacggaggcaaagagagctagatGCTCGCAGCGACTATCCCGGCGCAAGGGC

CTCATGTATGGAGCCGAACACTCAGCTCGGGCCGCTAAGGCGGCTCTGGCGGGG

CCGACGCCTCGCGCGCGCTCGAGGCTCGGGTTTATCCGCACCGACGGTACGCCG

GTCGTCCTGGCATCGGTGTCACCTCACCGTTCCGCAGATCTCTCGCTGCCGACCA

AGCAAGCCAACCGGGGAGGCCGGGGAAAAGATGATCGAGATCGTGCGGACGCC

TGGTGACGTACACCGGATTGCCAGGGACTACGACCTCCCTTTCCCGGGCTCCTCT

TCGTGGTATCAAGACCAGCAACGAAACCAGAGCGCTCACATGGCCTGGACGGGT

-continued

```
TTGCGCGTGTCCGGCAAGACTGCTAGGCGCGAGATAGGTGTTGGGCGTGCGCGA

AGGAAACCTTAGTGGTACTAAGAAGCCTGATAGGGCGTGCCTTAGCGAGATCTC

TCGTGCACAGAGATTTTACTTCGCCCACCACAAACAACCGGAAGAAGGACGGCC

AACAGAGACGAGATCCTCTCGCAAGCACCCCTATCAGGCAGTATAGCGCACAAG

GCCTTTCGCGACCCAGCACTACTCGGGTCGCTCGGCAGAGTCTTTGGGCGCGCC

AAATGTGCCAGGCATTGGACGGCGTTATCCCCGAAAGGGACACCACGGTCGTCC

TGCAGAAGCGTGCCGGTGTCACTGCACCGGTTCCGCGCAGTCTCtcttcgctcaacaagcag acaacggaagcggaggaaaagagagtagatCTGGCACCGGGTGAGTACTACGCAATTTTGCGCCA

GGCAGCACGGGTCCCTTCGTGGATAGAACCCGGCTCATGCCTGGGACTTTGGGC

GTCGGCCCCGCAAGACTGCTAGGCCCGAGTAGTGTTGGGTCGCGAAAATGGCC

TTGTGGTACTACTCGCCTTAGGAGTACGCTTGTGAGATCTtctctcgcaacaaaccacgacgga ggcgggaggaaaagagagagagaATCGGTCGCAAAGCCCCACTACATCAGGCAGTACCCTACA

AGGGCCTTTCGCGACTCCAACACTACTTCGGCTCTACGTCAGTCTTGCGCGGGGG

CAGGGCCGAATCTCAAGACATTGACGCGGGGTTTCTCCACGGAGGACGAGATCC

GTTCCTTGTGCAATTCCGTGTACTACAGCCGGTTTCGCAGATCCTCTCCCAACAA

GCAACGCGAGGCGGCAACGGAACATGAGAGAGATCTGGCACCGTGAGTGTACG

CACGGAATTGCAGGCACGACGGGTCTTTCGTGGATAGTCAACCCGCTATTGCTGG

AGATTTGTGCGTTGCACCCAGCAATGACTGCTAGCGGCCGACGTACGACGGGGT

TAGGAAAAAGGGGTCGCGAAGGCCTTTGTGGTAACTACCGGCTGATAGGCGTGC

TTGGCGAGATCCTGCTCTCCTCTCGCACTAACAACAGCGGGGAGGCCTGGAAGA

GGAGAATTCTTCGCCAGCCGCCCGATCCAGACAGCATAGTACTACACCCGGTGG

CTTCTTCGCGCCCACACTACTCGGCTCGACGATCTTGCGGGCACGCCCAAAATC

GTCCGCAGGGCCTTGAGGCGGGTTATCCACGTAAAGGCCACGACCGGTCGTCCT

GGCGACATATCTCGGTGTACTCCGCGAGTTCCGCTCGATCTCTTCTCGATATCAC

CAACGTGAGGCCAGGCGGCAAAAAGAGAGAGTCTGCGAACGCGGCTGACGATA

CACCGGATTGCAGGACGACCGGGTCTTTATCCGTGGATAGACACCCGCCATGCC

TGGAGATTTGGCGCGTTGCCCGCAAGACTGCTAGCGAGTAGCTCGTTGGGCGTC

GGCCGAACGGCCTTGTGGTACTGGCTGATAAGGGGTGCTTGCGACGatctcttccttcaca acaacaaccggaggaggaggaaaagagaggaAGGATCTCGCAGCACCCCTACCTCAGGCAAGTA

CCACAAGGCTTTCGGACCCAACCTACCTCGCTAGCAGGTCTTGCGGGGGCCACG

CCAAATCTCCCCAGGCATTGAGCAGGCGTTTATCCAACCGACAAGCCTCGCCCG

GGCGGCGCCCGCCCGCCCAGCCTGTCTCCTCTTCTCTTTCTCTTTCTTCTGGCGCT

CGCCTCCTCGTCGGTCCCCGGCGTTCCGGCCCGGCGTCCCCTCATGTCTCGCCGC

GCGCCCCCTCCTCCTTTGCCTGCCCGCTCTCGCCCCCTGTTTCCTTCCACGCTGG

CTCGCGCGTGCGCTGTCACTCCCGCCCTCCCGGTCCGCAGA
```

>ZMW ID 21

(SEQ ID NO: 17)

```
CCCGCAGACTGCTAGCCGAGTAGTGTTGGGTCGCGAAGGGCCTTGTGGTACTCTC

CGCCTGATGGGGTGGCTTGCGAGAACGCCCCCGCGCCAAAAAAACATGCTCTCC

TCCACAACAACAACGGAGGAGGGTGCTGCTTTAGGAAAAGAGAGAGATTCGCA

GCCCCACGCAGCCCTAGTCCCGCAGCAGCGTACCCACCCACCCCAGCGCCTGTTC

GCCGACCGCCACACTACCGGCTTAGCAAGTCTTGCGGGGCACGCCCAAATCTCC
```

```
CGGGCATTGAGCGCGTTTTACTCCACCGGAAAGACCAGACCTCGGGCGTCTGGG

CATTCGGTTGCTAACTGCACCGGTTTTCCCCGCAGatcttttctcacacaaccacggggcggaggaa aagagagagatCTGGCGGTGAACCGGCTTGGTACACCCGGAATTGGCCCAGGGACGAC

CCCGGGTCCCTTTCTCGTGGATAGAACCCGCCTCCATGCCTGGAGATTTGGGCGT

CCCCCCGCCAGACTGCTAGCCGAGGTAGCTGTTTGGGCTCCGCGAAGGGCTTTGT

GGTACTGCTGAATAGGGTGCTTGCGAGATCTCCGtctccaacaacaacaacaacggaggaggagga aacatgaagagagatCCTTCGCAAGCACCCCTAGTCCAGCGGCAGTACCAACAAGGCCTT

TCGGCGACCCAACACGTTACTCGGCTAGCAGTCCTTGCGGGGGCACGCCCAAAT

CTCCCAGGCATTTGAGCCGACGCGCGTTTTTTTTATGCCCACCGAAAGGGGACCC

GGCCGTCCTGTGCCAAATTCCCGGTGTACTGCCACCCGGTTCCGCAGATtcgtctctcca acaacaacaacggaggaggaagggaaaagagagagatCTGCGGACCCGGTGAAGCTCACCGGAAAT

TGCCAAAAGGAGACCCGGGTCCTTTTTTCGTTTGGATAAACTCCGCTCATGCCTG

GAGATTTGGGCGCGTGCCCGCCCCGCAAGACTGCTTAACTAGCCGAGTAGTGTT

GGGTCGGCGAAAGGCCTTGGTGGTAACTGCCTGATAGGGTGGGCGTTGGCGAGat ctcctttcaacaacaacaacgggagggaggaggaaaagagagagatCTCGCAAGCAAGCCCTATCAGGCGT

ACCACACGGCCTTTTCGCGGAACCAAACACCTACTCCGGCTAGCAAGCTTCCTGC

GGGGGGCCACGGCCAATCTCCAGCCATTTGAGCGGGTTTTTATCACACGAAGAC

CCGGCCGGTCTGGCAATCTCCGGTGTAGCTGCAACGCGGTTCCGCAGatctcttgctcaac aacaacaacggaggaggcaaaggaaacagagagagatCTGCGGAACCGGTGAGTCACCGGAAATTT

GCCCAGGACGACACGGGTCCTTTCGTGGATAACACCGCCAATGCCGTGGGAGAT

TTGGGCGTGCCCCGCAAGAAACTCTGCCTAGCCGAGTACGTGTTTGGGTCCGGC

GAAAGGGCCTTGTGGTAATTCGCCTGATAGGGTGCTTGGCGGAGCatctctctcaacaacg gaaaaacggaggaggagggaaagagaggagatCCTCGCAAAGCACCCTATCAGGCAGTGACAAC

AAGGCCTTTCGCGACCTAACACTACTTCGGCGTTAGCATCTTTGCCGGGGCAGG

CCCAAATCTCATACAGGCATTGGAGGCGCGGGTTTTATCCACCCGAAAAGACCC

GCCGGTCTGGCGGGGCAATTCCGGTGGTACTTCAACGGTTTCCCGCCAAGAatttctc ctcaaacaacaacaacggggaggaggaaaagagagagatCC
>ZMW ID 25
                                                              (SEQ ID NO: 18)
CCCGTCTGAGCCCGGCGTTCCTATCCACGACCCCGGACCCCCGCGCCTCGTCCCC TGCGCCGCAACTGTCCGGCCCTGCTCAACCCTCCGGTTCCGGCCAGatctcctctaacaac accaacggaaggaggaggaaaagagatgacgatCTGCGGAACCGGTTGAGTACACCGGAATTGCC

AGGACGACCGGGTCCTTTCGTGGATAAACCCGCTCATGCCCGGAGAATTTGGGC

GGTGCCCACGCAAGACCTCGCTCCGATTCAGCGATAGTCGTTGGGTCGCGAAAG

GCCTTTGTGGTACTGCCTGATAAGGGTGCCTGCGAGATCTTCTCAACCAGCACAA

GCGGCAGGGAGGCGAGGAAAAGAGAGAAGATCTCGCACGCACCCCCGCCTATC

AGCGCAGTACCACAAGGCCTTTCGCGACCAACAACCTACTCGGCCCGCCTAGCA

GTCTTGCCGGGGCACGCAAATCTCCAGGCATGAGCGGGTTATCCACCGACAGG

ACCGTCGCGTCGTCCTGGCAATTCCGGTGTACTGCACAAGGCTTCCGCAGGCATC

TCTCTCAACCCACACCGCAACGAGGAGGAGGAAATACAGAGAGAGATCTGCGG

AACCGGTGAGTACACCCGGATTGCAGGACACCGGGTCCTTTCCGTGGATAACCC
```

```
GTCGAATGCCCCGGAGACTTTGGGCGTGCCACGCAAGATGCTCAGCCCGAGTAG

TGTCTGGGTCGCGAAAGGCCTTGTGTACTGCTGATAGGGTGCTTGCGAAGatctctctc aacaacaacaacggggaggaggaaagagatgagatCTCGCAAGCAACCCCTATCAGGGCAGGTCAC

CACAAGGGCCTCGTATCGCGACCCACACTACTCGGCCTAGCAGTCTTGCGGGGG

GGCACGCCGAAATCTCCAGGCATGTGAGCGGGTTTATCCCGCGAAAGGGCCACG

CGGCTCGTGCTGGCCGAATTCCGGTGTACACTCACCGGTTCCGCAGATCTCTTCT

CCATCAGCACAACAACGAGGAGGAGGAAAAGAGCAGGAAGATCTGCGGAACCG

GTGACCGTACACCGGATTGCCAGGACGACCAGGGTCCTTCTCGTGGATATACCC

GCTCAATGCCCTCGGAGATTTTTGGCCGTGCCCACGCAAGAATGCTAGCCGAGT

ATTGTTTGGGTTCGCGAAAGGCCTTGTGGTCTGCGCCTGATAGGGTGCTTGCGAG tctctctcaacaacaacaccggagggaggacaagagagagatCTCGCAAGCACCCTATGCCAGGGCCGT

ACCCCCACGGGGCGGGGCCTGGTTCGCGAGCCCAAACACCTACTCGGCTAGGCA

GGTCTTGCGGGGCACGCCCAAATCTCCAGGCATTGAGCGGGTTTATCACGACAG

GACCCGCGTCGTCCTGGCATTCCGTGTGTACTCCAACCGGTTTCCCGCAGatctatctca acaacacaacggaggaaggtaaggaacagaggagagatCTGAGGAGAAACGCCGCGTGGAGTACACG

GATTGCCAGGACGGACCGGGTCCTTTCGTGGATAAACCCGCTCAAATCCGGAGA

TTTGGGGCGTCGGCCCACCGCAGACTGCTAGCCGAGTACTGTTGGGTCGCGAAA

GGCCTTGTGGGTACTGCCTATAGGGTGGCTGCCGAGatcttctctcaacacacacggagggcagcg aggaaaagagagaCAGCTCTCGGAACGCCCCTATTCAGGGGCCAAGGCCTTCCCGCTCG

GCGACCCCACACTACTCGGATAGCCAGTCTTGCGGGGCCACGCCCAAAATCTCC

AGCCATTCGGAGCGGGTTTAATCCACGAAAGGACCCCGGTCGTCCTGCAATTCC

GGTGTACTCACCGGTTCCGCAGATtctctctcaacaacaacaaccgagaggagggacggaaaagagagacg atCTGCGGAACCGGTGAGGCTACAGCCCGGAATTGCCAGGACGACCGGTCCTTCT

CGTGATACAACCCGCCTCAATGCCGAAGAATTTGGGCGTTGCCCACGCAACGAC

TCGCTAGCCCGACGTAGTGTTGGGTCCGACGAAAGGCTTGTTTGCGTACTGCTGT

AGGGTGCTTTGCGAGATCTtcgctctcacaacaacaacggaggcaggaagggaaaagagagagTCCTCGC

AAGCACCGCCTAGTCAGGCAGTACCACAAGGCCTTTCCGCGACCGCAACAACTA

TCGGGCCGCTAGCAGTCTTGCGGGGCACGCCCAATTCTCCAGGCTTGAGCGGGTT

TTATCACCGAAGGACCCGGTCGTCCTGGCAATTCCGGTTGTACGCTCACCGGTCC

GCAGatctcctctcacacacacaacggaggaggaggaaagacgagagatCTGCGGAACCGGGGTGAGTAC

ACGGACATTGCCAGGACGCCGGGTTCTTTCGTGGATAAACCGCTCAATGCCCGG

AGATTTGGGCGTGCCCCACGCAATGACTGCTAGCCAGTAGTGTTGGGCTCGCGA

AAGGCCCTTGTGGGTACTGCGCCTGATAAGGGTGCTTGCGAGatcttctcaacaacacaacga gaggagggaaaagagagagatCTCGCAAGCACCTATCAGGCGTACACAACGGCCTTCAATC

AGAAAAAAGACCCAGACACTACTCGGCTAGACAGTCTTGCGGGGCACGCCCCA

AATCTCAGGCATTGAACGGGTTTATCCACGAAAGGACCGCGGTCGTCCCCTGGC

AATCTCGGTGTACTCCAGCGGTTTCCGCACAGATCCTCTCCTCCCACACGCCaaca acaacaacgcgaggaggaggcgaaaagacgagagatTCTGCGAACCGGTGAGTACACCGGAATTGC

CAGGCCGGACCGGGTCCTTTCGTGGCTAAACCCCGCTCAATGCCGCGGAGATTT

GGGGCGTTCGCCACGCACGACTCGCTAGCCGAGTAGTGTTGGGCTCCGCCCCGG

AAAGGCCTTGGTGGCTACTGCCTGATAGGGTGCTGCGAGatctctctcaagcaacaacaacgga
```

-continued

```
ggacgggaggaaaagacgacgacgcatCTCGCCACGCAGCCCTAATCAGGGGGCAGTCACCGG

GCACAAGGCGCTTTCGCGCACCCCATCACACTCAATGCGCGCCTGGAGCAGTCC

ACCCGCTTGCCGGGAGGCCTCGGCACGGCCAAACGCGCCAGATCTCGCACGGCA

TCCGTGGAGCCGCGGTTTACTCCCACGAAGAGGATCCCCGGTCGTGCGCTGGGC

AATTCCGGTGTACCTCGCTTGCAGCCCGGCTTCCGCATGATCTCCTCTCCAATCA

ACAACAACGGAGGAGGGAGGAAAAAACGAGGAGCAGATCCGTGGCGGACAAC

GCCGGTGAGGTACAACCCGGGAAATTCCGCCGAAGCAAACGGCGACCGGTCTCT

TCCCCACGCAACACCACGCGATCAATCCAAACAAAAAAAAAAAAAAAAAAAAA

AAACGTGGAAACCAAGAGGAACACCACCCGCCCCCCGGGCACCC
```

Example 5

Run the Polling Algorithm to Generate One Consensus

From the initial 179001 sequences in the accepted set, the first poll produced the first base of the consensus that is C with about ⅔ of the bases (See Table 4). The distribution of the base were 114994, 26000, 19299, 18708 for C, A, G, T respectively. For the first two iterations, we skipped the scoring sequences from the rejected set simply because there is no chance for those sequences to be scored high and returned to the accepted set. The Overlap Matching alignment was used for the scoring starting at the third step. The cutoff was 0.25 per base. A sequence with a matching score less than the cutoff would be returned to the accepted set.

We started at the third step with 82079 in the accepted set and 96922 in the rejected set and the consensus sequence is CT. The polling found G is the next dominant base and rejected 44131 sequences. Then the Overlap Matching alignment of the 141035 sequences (96922 plus 44131) to the consensus sequence CTG and found 14915 sequences with good matches, and returned them to the accepted set. Therefore, at the end of the third step, we have consensus CTG, 52863 in the accepted set and 126138 in the rejected set. The data points mentioned in the paragraph are highlighted in Table 4.

To illustrate the process furthermore, nine subreads at step 5 are listed below. We started with the consensus CTGC. The next bases to be polled are lined up. It is obvious that G was the dominant base and should be incorporated in the consensus. Sequence 4 should be moved to the rejected set. Notice that sequences 3, 4, and 5 have an extra G at the fourth position (can be considered as an insertion there).

They must have been rejected initially in step 4 and then returned back into the accepted set because they had high enough matching score in the pairwise-alignment analysis.

| | | |
|---|---|---|
| 1 | CTGC G | (SEQ ID NO: 19) |
| 2 | CTGC G | (SEQ ID NO:19) |
| 3 | CTGGC G | (SEQ ID NO: 20) |
| 4 | CTGGC A | (SEQ ID NO: 21) |
| 5 | CTGGC G | (SEQ ID NO: 20) |
| 6 | CTGC G | (SEQ ID NO: 19) |
| 7 | CTGC G | (SEQ ID NO: 19) |
| 8 | CTGC G | (SEQ ID NO: 19) |
| 9 | CTGC G | (SEQ ID NO: 19) |

The consensus generation was set to be terminated if the number of early-terminated subreads more than doubled from one step to the next. This round of consensus generation stopped when the terminated subreads jumped from 2934 to 27713, a more than nine fold increase. The generated consensus sequence exactly matched the amplicon sequence, representing 44490 sequences.

TABLE 4

The statistics at each step of the polling process for the first consensus

| Step | SEQ ID NO: | Consensus generated (omitted after 30) | Accepted size | Rejected Size | Newly rejected | Newly returned |
|---|---|---|---|---|---|---|
| 1 | — | C | 179001 | 0 | 64007 | 0 |
| 2 | — | CT | 114994 | 64007 | 32915 | 0 |
| 3 | — | CTG | 82079 | 96922 | 44131 | 14915 |
| 4 | 22 | CTGC | 52863 | 126138 | 9965 | 12798 |
| 5 | 19 | CTGCG | 55696 | 123305 | 11862 | 53929 |

TABLE 4-continued

The statistics at each step of the polling process for the first consensus

| Step | SEQ ID NO: | Consensus generated (omitted after 30) | Accepted size | Rejected Size | Newly rejected | Newly returned |
|---|---|---|---|---|---|---|
| 6 | 23 | CTGCGG | 97763 | 81238 | 49577 | 17871 |
| 7 | 24 | CTGCGGA | 66057 | 112944 | 17367 | 10949 |
| 8 | 25 | CTGCGGAA | 59639 | 119362 | 11308 | 13704 |
| 9 | 26 | CTGCGGAAC | 62035 | 116966 | 21156 | 12550 |
| 10 | 27 | CTGCGGAACC | 53429 | 125572 | 11945 | 34538 |
| 11 | 28 | CTGCGGAACCG | 76022 | 102979 | 34638 | 23424 |
| 12 | 29 | CTGCGGAACCGG | 64808 | 114193 | 20730 | 13214 |
| 13 | 30 | CTGCGGAACCGGT | 57292 | 121709 | 14288 | 12986 |
| 14 | 31 | CTGCGGAACCGGTG | 55990 | 123011 | 9236 | 11890 |
| 15 | 32 | CTGCGGAACCGGTGA | 58644 | 120357 | 12587 | 14177 |
| 16 | 33 | CTGCGGAACCGGTGAG | 60234 | 118767 | 14136 | 15506 |
| 17 | 34 | CTGCGGAACCGGTGAGT | 61604 | 117397 | 17413 | 11500 |
| 18 | 35 | CTGCGGAACCGGTGAGTA | 55691 | 123310 | 10119 | 13459 |
| 19 | 36 | CTGCGGAACCGGTGAGTAC | 59031 | 119970 | 15801 | 16710 |
| 20 | 37 | CTGCGGAACCGGTGAGTACA | 59940 | 119061 | 16114 | 33422 |
| 21 | 38 | CTGCGGAACCGGTGAGTACAC | 77248 | 101753 | 34352 | 14127 |
| 22 | 39 | CTGCGGAACCGGTGAGTACACC | 57023 | 121978 | 15523 | 16687 |
| 23 | 40 | CTGCGGAACCGGTGAGTACACCG | 58187 | 120814 | 26073 | 16440 |
| 24 | 41 | CTGCGGAACCGGTGAGTACACCGG | 48554 | 130447 | 13237 | 13830 |
| 25 | 42 | CTGCGGAACCGGTGAGTACACCGGA | 49147 | 129854 | 11748 | 14166 |
| 26 | 43 | CTGCGGAACCGGTGAGTACACCGGAA | 51565 | 127436 | 8564 | 17263 |
| 27 | 44 | CTGCGGAACCGGTGAGTACACCGGAAT | 60264 | 118737 | 21062 | 10416 |
| 28 | 45 | CTGCGGAACCGGTGAGTACACCGGAATT | 49618 | 129383 | 8836 | 10108 |
| 29 | 46 | CTGCGGAACCGGTGAGTACACCGGAATTG | 50890 | 128111 | 11249 | 13467 |
| 30 | 47 | CTGCGGAACCGGTGAGTACACCGGAATTGC | 53108 | 125893 | 9505 | 21651 |
| 31 | | | 65254 | 113747 | 18871 | 20863 |
| 32 | | | 67246 | 111755 | 22646 | 19167 |
| 33 | | | 63767 | 115234 | 18193 | 15587 |
| 34 | | | 61161 | 117840 | 13398 | 17384 |

TABLE 4-continued

The statistics at each step of the polling process for the first consensus

| Step | SEQ ID NO: | Consensus generated (omitted after 30) | Accepted size | Rejected Size | Newly rejected | Newly returned |
|---|---|---|---|---|---|---|
| 35 | | | 65147 | 113854 | 20073 | 8978 |
| 36 | | | 54052 | 124949 | 11515 | 14100 |
| 37 | | | 56637 | 122364 | 17025 | 16122 |
| 38 | | | 55734 | 123267 | 16778 | 14578 |
| 39 | | | 53534 | 125467 | 13981 | 12212 |
| 40 | | | 51765 | 127236 | 11483 | 26561 |
| 41 | | | 66843 | 112158 | 35648 | 12012 |
| 42 | | | 43207 | 135794 | 6848 | 12433 |
| 43 | | | 48792 | 130209 | 12659 | 16392 |
| 44 | | | 52527 | 126474 | 15338 | 6996 |
| 45 | | | 44190 | 134811 | 8778 | 15930 |
| 46 | | | 51347 | 127654 | 12923 | 17754 |
| 47 | | | 56186 | 122815 | 14998 | 17921 |
| 48 | | | 59124 | 119877 | 16010 | 14241 |
| 49 | | | 57376 | 121625 | 10879 | 11652 |
| 50 | | | 58174 | 120827 | 13281 | 9551 |
| 51 | | | 54473 | 124528 | 14658 | 13924 |
| 52 | | | 53772 | 125229 | 14505 | 13995 |
| 53 | | | 53299 | 125702 | 9755 | 9569 |
| 54 | | | 53167 | 125834 | 8883 | 9895 |
| 55 | | | 54236 | 124765 | 12433 | 7752 |
| 56 | | | 49618 | 129383 | 9334 | 19022 |
| 57 | | | 59375 | 119626 | 15454 | 10353 |
| 58 | | | 54349 | 124652 | 9130 | 14081 |
| 59 | | | 59385 | 119616 | 14028 | 6916 |
| 60 | | | 52362 | 126639 | 13466 | 10914 |
| 61 | | | 49905 | 129096 | 7646 | 18302 |
| 62 | | | 60669 | 118332 | 18664 | 11928 |
| 63 | | | 54055 | 124946 | 20405 | 14373 |
| 64 | | | 48154 | 130847 | 12198 | 17810 |
| 65 | | | 53920 | 125081 | 18203 | 13074 |
| 66 | | | 48957 | 130044 | 8908 | 8615 |
| 67 | | | 48836 | 130165 | 8893 | 18242 |
| 68 | | | 58362 | 120639 | 16139 | 17273 |
| 69 | | | 59678 | 119323 | 24104 | 9033 |
| 70 | | | 44794 | 134207 | 7642 | 13128 |
| 71 | | | 50470 | 128531 | 9146 | 19209 |

TABLE 4-continued

The statistics at each step of the polling process for the first consensus

| Step | SEQ ID NO: | Consensus generated (omitted after 30) | Accepted size | Rejected Size | Newly rejected | Newly returned |
|---|---|---|---|---|---|---|
| 72 | | | 60729 | 118272 | 14745 | 13502 |
| 73 | | | 59694 | 119307 | 19389 | 13108 |
| 74 | | | 53637 | 125364 | 13656 | 9637 |
| 75 | | | 49854 | 129147 | 6114 | 16206 |
| 76 | | | 60196 | 118805 | 15221 | 9720 |
| 77 | | | 54953 | 124048 | 11659 | 15499 |
| 78 | | | 59056 | 119945 | 16262 | 9596 |
| 79 | | | 52660 | 126341 | 12704 | 10582 |
| 80 | | | 50813 | 128188 | 6209 | 13179 |
| 81 | | | 58065 | 120936 | 13201 | 10722 |
| 82 | | | 55882 | 123119 | 13667 | 4597 |
| 83 | | | 47116 | 131885 | 4400 | 10757 |
| 84 | | | 53786 | 125215 | 12359 | 10225 |
| 85 | | | 51981 | 127020 | 11935 | 7755 |
| 86 | | | 48141 | 130860 | 14030 | 20101 |
| 87 | | | 54561 | 124440 | 16701 | 12618 |
| 88 | | | 50845 | 128156 | 12717 | 9321 |
| 89 | | | 47830 | 131171 | 9451 | 11740 |
| 90 | | | 50505 | 128496 | 5981 | 19800 |
| 91 | | | 64728 | 114273 | 16319 | 12222 |
| 92 | | | 61067 | 117934 | 16241 | 6365 |
| 93 | | | 51659 | 127342 | 21032 | 5777 |
| 94 | | | 36893 | 142108 | 14631 | 9883 |
| 95 | | | 32651 | 146350 | 8044 | 23761 |
| 96 | | | 48925 | 130076 | 11346 | 15219 |
| 97 | | | 53376 | 125625 | 11708 | 22066 |
| 98 | | | 64327 | 114674 | 21640 | 12338 |
| 99 | | | 55638 | 123363 | 16424 | 10164 |
| 100 | | | 50030 | 128971 | 11730 | 13787 |
| 101 | | | 52759 | 126242 | 14268 | 7517 |
| 102 | | | 46720 | 132281 | 10893 | 11049 |
| 103 | | | 47602 | 131399 | 10905 | 16890 |
| 104 | | | 54333 | 124668 | 18417 | 10017 |
| 105 | | | 46699 | 132302 | 10524 | 13928 |
| 106 | | | 50890 | 128111 | 13712 | 12025 |
| 107 | | | 50000 | 129001 | 10652 | 10501 |
| 108 | | | 50659 | 128342 | 10203 | 15584 |

TABLE 4-continued

The statistics at each step of the polling process for the first consensus

| Step | SEQ ID NO: | Consensus generated (omitted after 30) | Accepted size | Rejected Size | Newly rejected | Newly returned |
|---|---|---|---|---|---|---|
| 109 | | | 56869 | 122132 | 17881 | 7781 |
| 110 | | | 47635 | 131366 | 8276 | 9503 |
| 111 | | | 49747 | 129254 | 11847 | 11253 |
| 112 | | | 50053 | 128948 | 9315 | 6967 |
| 113 | | | 48696 | 130305 | 9998 | 9995 |
| 114 | | | 49695 | 129306 | 11436 | 7769 |
| 115 | | | 47036 | 131965 | 9204 | 7643 |
| 116 | | | 46554 | 132447 | 9071 | 8961 |
| 117 | | | 47535 | 131466 | 9866 | 6916 |
| 118 | | | 45681 | 133320 | 6519 | 16195 |
| 119 | | | 56465 | 122536 | 19096 | 9784 |
| 120 | | | 48284 | 130717 | 5765 | 9224 |
| 121 | | | 52886 | 126115 | 11413 | 9706 |
| 122 | | | 52359 | 126642 | 19003 | 2723 |
| 123 | | | 37299 | 141702 | 6838 | 15797 |
| 124 | | | 47494 | 131507 | 13657 | 18342 |
| 125 | | | 53432 | 125569 | 11954 | 7878 |
| 126 | | | 50637 | 128364 | 11854 | 13634 |
| 127 | | | 53716 | 125285 | 11775 | 9234 |
| 128 | | | 52499 | 126502 | 11018 | 11459 |
| 129 | | | 54308 | 124693 | 15627 | 8478 |
| 130 | | | 48544 | 130457 | 15301 | 4729 |
| 131 | | | 39378 | 139623 | 7013 | 16293 |
| 132 | | | 50146 | 128855 | 12080 | 12755 |
| 133 | | | 52331 | 126670 | 11221 | 16356 |
| 134 | | | 58998 | 120003 | 22818 | 10540 |
| 135 | | | 48357 | 130644 | 7920 | 10434 |
| 136 | | | 52526 | 126475 | 15722 | 10780 |
| 137 | | | 49256 | 129745 | 9569 | 5523 |
| 138 | | | 46896 | 132105 | 6868 | 9054 |
| 139 | | | 50775 | 128226 | 8095 | 9594 |
| 140 | | | 53980 | 125021 | 13734 | 4968 |
| 141 | | | 46947 | 132054 | 8485 | 7744 |
| 142 | | | 47956 | 131045 | 13700 | 14683 |
| 143 | | | 50705 | 128296 | 15142 | 8835 |
| 144 | | | 46203 | 132798 | 16167 | 13688 |
| 145 | | | 45583 | 133418 | 11996 | 9840 |

TABLE 4-continued

The statistics at each step of the polling process for the first consensus

| Step | SEQ ID NO: | Consensus generated (omitted after 30) | Accepted size | Rejected Size | Newly rejected | Newly returned |
|---|---|---|---|---|---|---|
| 146 | | | 45346 | 133655 | 12349 | 16077 |
| 147 | | | 51023 | 127978 | 18671 | 10408 |
| 148 | | | 44751 | 134250 | 9391 | 8322 |
| 149 | | | 45692 | 133309 | 8604 | 12148 |
| 150 | | | 51259 | 127742 | 14748 | 6636 |
| 151 | | | 45187 | 133814 | 8758 | 5601 |
| 152 | | | 44099 | 134902 | 9162 | 12223 |
| 153 | | | 49242 | 129759 | 8446 | 9105 |
| 154 | | | 52073 | 126928 | 13358 | 7117 |
| 155 | | | 48035 | 130966 | 14938 | 3586 |
| 156 | | | 38904 | 140097 | 7751 | 9171 |
| 157 | | | 42595 | 136406 | 10721 | 11489 |
| 158 | | | 45649 | 133352 | 13279 | 7927 |
| 159 | | | 42607 | 136394 | 8931 | 10176 |
| 160 | | | 46189 | 132812 | 11630 | 7796 |
| 161 | | | 44705 | 134296 | 8667 | 7355 |
| 162 | | | 45762 | 133239 | 11408 | 12879 |
| 163 | | | 49629 | 129372 | 12977 | 9778 |
| 164 | | | 48918 | 130083 | 13895 | 9467 |

Example 6

Run the Polling Algorithm to Generate the Second Consensus

The remaining 131577 sequences in the rejected set from the last example were used as the input for the second consensus generation. The process stopped when terminated subreads increased from 2689 to 26488, almost ten times. This time the sequence generated matched perfectly to the reverse strand of the amplicon sequence, representing 41808 sequences.

TABLE 5

The statistics at each step of the polling process for the second consensus

| Step | SEQ ID NO:30 | Consensus (omitted after | Accepted size | Rejected size | Newly rejected | Newly returned |
|---|---|---|---|---|---|---|
| 1 | | — C | 131577 | 0 | 49289 | 0 |
| 2 | | — CT | 82288 | 49289 | 25463 | 0 |
| 3 | | — CTC | 56825 | 74752 | 21285 | 17963 |
| 4 | 48 | CTCG | 53503 | 78074 | 15524 | 9754 |
| 5 | 49 | CTCGC | 47733 | 83844 | 7484 | 28820 |
| 6 | 50 | CTCGCA | 69069 | 62508 | 28852 | 15530 |
| 7 | 51 | CTCGCAA | 55747 | 75830 | 14982 | 11761 |
| 8 | 52 | CTCGCAAG | 52526 | 79051 | 16118 | 10449 |

TABLE 5-continued

The statistics at each step of the polling process for the second consensus

| Step | SEQ ID NO: | Consensus (omitted after 30) | Accepted size | Rejected size | Newly rejected | Newly returned |
|---|---|---|---|---|---|---|
| 9 | 53 | CTCGCAAGC | 46857 | 84720 | 10305 | 14724 |
| 10 | 54 | CTCGCAAGCA | 51276 | 80301 | 13134 | 24531 |
| 11 | 55 | CTCGCAAGCAC | 62673 | 68904 | 20412 | 8228 |
| 12 | 56 | CTCGCAAGCACC | 50489 | 81088 | 7678 | 15564 |
| 13 | 57 | CTCGCAAGCACCC | 58375 | 73202 | 19113 | 8873 |
| 14 | 58 | CTCGCAAGCACCCT | 48135 | 83442 | 15343 | 7349 |
| 15 | 59 | CTCGCAAGCACCCTA | 40141 | 91436 | 7052 | 15067 |
| 16 | 60 | CTCGCAAGCACCCTAT | 48156 | 83421 | 12666 | 12094 |
| 17 | 61 | CTCGCAAGCACCCTATC | 47584 | 83993 | 6985 | 16338 |
| 18 | 62 | CTCGCAAGCACCCTATCA | 56937 | 74640 | 20854 | 12471 |
| 19 | 63 | CTCGCAAGCACCCTATCAG | 48554 | 83023 | 8442 | 8653 |
| 20 | 64 | CTCGCAAGCACCCTATCAGG | 48765 | 82812 | 10054 | 22863 |
| 21 | 65 | CTCGCAAGCACCCTATCAGGC | 61574 | 70003 | 24213 | 11845 |
| 22 | 66 | CTCGCAAGCACCCTATCAGGCA | 49206 | 82371 | 16506 | 10032 |
| 23 | 67 | CTCGCAAGCACCCTATCAGGCAG | 42732 | 88845 | 8480 | 17900 |
| 24 | 68 | CTCGCAAGCACCCTATCAGGCAGT | 52152 | 79425 | 14123 | 12569 |
| 25 | 69 | CTCGCAAGCACCCTATCAGGCAGTA | 50598 | 80979 | 10021 | 13367 |
| 26 | 70 | CTCGCAAGCACCCTATCAGGCAGTAC | 53944 | 77633 | 11707 | 12493 |
| 27 | 71 | CTCGCAAGCACCCTATCAGGCAGTACC | 54730 | 76847 | 13884 | 10290 |
| 28 | 72 | CTCGCAAGCACCCTATCAGGCAGTACCA | 51136 | 80441 | 19186 | 9156 |
| 29 | 73 | CTCGCAAGCACCCTATCAGGCAGTACCAC | 41106 | 90471 | 9797 | 14231 |
| 30 | 74 | CTCGCAAGCACCCTATCAGGCAGTACCACA | 45540 | 86037 | 13210 | 12774 |
| 31 | | | 45104 | 86473 | 10417 | 12477 |
| 32 | | | 47164 | 84413 | 13130 | 8108 |
| 33 | | | 42142 | 89435 | 6682 | 16091 |
| 34 | | | 51551 | 80026 | 13131 | 13281 |
| 35 | | | 51701 | 79876 | 11843 | 9937 |
| 36 | | | 49795 | 81782 | 14551 | 8109 |
| 37 | | | 43353 | 88224 | 4394 | 10992 |
| 38 | | | 49951 | 81626 | 9653 | 10094 |

TABLE 5-continued

The statistics at each step of the polling process for the second consensus

| Step | SEQ ID NO:30) Consensus (omitted after | Accepted size | Rejected size | Newly rejected | Newly returned |
|---|---|---|---|---|---|
| 39 | | 50392 | 81185 | 14081 | 5273 |
| 40 | | 41584 | 89993 | 9273 | 15104 |
| 41 | | 47416 | 84161 | 12735 | 15665 |
| 42 | | 50347 | 81230 | 13521 | 10807 |
| 43 | | 47634 | 83943 | 12232 | 14538 |
| 44 | | 49941 | 81636 | 14873 | 12238 |
| 45 | | 47310 | 84267 | 7422 | 11357 |
| 46 | | 51276 | 80301 | 17354 | 8468 |
| 47 | | 42498 | 89079 | 13542 | 5153 |
| 48 | | 34265 | 97312 | 7361 | 19444 |
| 49 | | 46508 | 85069 | 14340 | 13229 |
| 50 | | 45564 | 86013 | 10745 | 7477 |
| 51 | | 42476 | 89101 | 7418 | 9868 |
| 52 | | 45117 | 86460 | 10444 | 9509 |
| 53 | | 44377 | 87200 | 9559 | 8617 |
| 54 | | 43633 | 87944 | 10191 | 10655 |
| 55 | | 44300 | 87277 | 10099 | 7424 |
| 56 | | 41836 | 89741 | 8976 | 8308 |
| 57 | | 41393 | 90184 | 11097 | 12270 |
| 58 | | 42799 | 88778 | 7688 | 14412 |
| 59 | | 49762 | 81815 | 16040 | 12832 |
| 60 | | 46812 | 84765 | 14967 | 6667 |
| 61 | | 38784 | 92793 | 6814 | 9283 |
| 62 | | 41528 | 90049 | 8077 | 13523 |
| 63 | | 47257 | 84320 | 11887 | 9707 |
| 64 | | 45373 | 86204 | 11723 | 11109 |
| 65 | | 45063 | 86514 | 10714 | 10190 |
| 66 | | 44855 | 86722 | 10635 | 9505 |
| 67 | | 44055 | 87522 | 8962 | 10352 |
| 68 | | 45785 | 85792 | 13688 | 7877 |
| 69 | | 40316 | 91261 | 6442 | 7949 |
| 70 | | 42166 | 89411 | 10535 | 12419 |
| 71 | | 44398 | 87179 | 10874 | 8866 |
| 72 | | 42743 | 88834 | 9433 | 12484 |
| 73 | | 46154 | 85423 | 6677 | 12519 |
| 74 | | 52362 | 79215 | 7606 | 7689 |
| 75 | | 52827 | 78750 | 7146 | 4760 |

TABLE 5-continued

The statistics at each step of the polling process for the second consensus

| Step | SEQ ID NO: Consensus (omitted after 30) | Accepted size | Rejected size | Newly rejected | Newly returned |
|---|---|---|---|---|---|
| 76 | | 50834 | 80743 | 14193 | 4157 |
| 77 | | 41203 | 90374 | 14703 | 3249 |
| 78 | | 30162 | 10141 | 57814 | 16293 |
| 79 | | 39061 | 92516 | 11324 | 15240 |
| 80 | | 43407 | 88170 | 10665 | 11497 |
| 81 | | 44679 | 86898 | 10084 | 11059 |
| 82 | | 46106 | 85471 | 6102 | 11146 |
| 83 | | 51611 | 79966 | 16715 | 6762 |
| 84 | | 42156 | 89421 | 12065 | 4884 |
| 85 | | 35489 | 96088 | 3599 | 19131 |
| 86 | | 51543 | 80034 | 12761 | 8347 |
| 87 | | 47685 | 83892 | 14291 | 4150 |
| 88 | | 38142 | 93435 | 7005 | 13226 |
| 89 | | 44967 | 86610 | 10884 | 10223 |
| 90 | | 44925 | 86652 | 6721 | 6796 |
| 91 | | 45623 | 85954 | 8531 | 11722 |
| 92 | | 49445 | 82132 | 13937 | 8084 |
| 93 | | 44235 | 87342 | 7208 | 9343 |
| 94 | | 47028 | 84549 | 6892 | 16241 |
| 95 | | 57045 | 74532 | 17317 | 7852 |
| 96 | | 48255 | 83322 | 11872 | 6496 |
| 97 | | 43564 | 88013 | 8613 | 8032 |
| 98 | | 43684 | 87893 | 6371 | 10758 |
| 99 | | 48782 | 82795 | 9835 | 8802 |
| 100 | | 48467 | 83110 | 9759 | 8202 |
| 101 | | 47633 | 83944 | 10902 | 9744 |
| 102 | | 47210 | 84367 | 11835 | 9750 |
| 103 | | 45886 | 85691 | 13333 | 11132 |
| 104 | | 44464 | 87113 | 7044 | 11864 |
| 105 | | 50079 | 81498 | 12673 | 9357 |
| 106 | | 47575 | 84002 | 10538 | 4318 |
| 107 | | 42191 | 89386 | 5362 | 13386 |
| 108 | | 51066 | 80511 | 8821 | 8202 |
| 109 | | 51328 | 80249 | 19122 | 3497 |
| 110 | | 36671 | 94906 | 7904 | 7765 |
| 111 | | 37525 | 94052 | 7163 | 18501 |
| 112 | | 49865 | 81712 | 10754 | 11545 |

TABLE 5-continued

The statistics at each step of the polling process for the second consensus

| Step | SEQ ID Consensus (omitted after NO:30) | Accepted size | Rejected size | Newly rejected | Newly returned |
|---|---|---|---|---|---|
| 113 | | 51676 | 79901 | 16811 | 8088 |
| 114 | | 44000 | 87577 | 8733 | 8088 |
| 115 | | 44411 | 87166 | 11148 | 12028 |
| 116 | | 46356 | 85221 | 9680 | 8129 |
| 117 | | 45903 | 85674 | 5740 | 13360 |
| 118 | | 54632 | 76945 | 13222 | 5479 |
| 119 | | 48013 | 83564 | 13095 | 2910 |
| 120 | | 38962 | 92615 | 5280 | 14109 |
| 121 | | 48931 | 82646 | 11179 | 12921 |
| 122 | | 51822 | 79755 | 12920 | 6550 |
| 123 | | 46612 | 84965 | 8470 | 12408 |
| 124 | | 51737 | 79840 | 16021 | 8535 |
| 125 | | 45473 | 86104 | 16080 | 6694 |
| 126 | | 37326 | 94251 | 9148 | 13840 |
| 127 | | 43284 | 88293 | 12279 | 11998 |
| 128 | | 44288 | 87289 | 7481 | 9448 |
| 129 | | 47548 | 84029 | 16712 | 11273 |
| 130 | | 43420 | 88157 | 9401 | 8686 |
| 131 | | 44039 | 87538 | 10549 | 10398 |
| 132 | | 45252 | 86325 | 11681 | 7452 |
| 133 | | 42402 | 89175 | 13252 | 12448 |
| 134 | | 43004 | 88573 | 8978 | 9704 |
| 135 | | 45147 | 86430 | 7370 | 11084 |
| 136 | | 50302 | 81275 | 12861 | 5168 |
| 137 | | 44065 | 87512 | 7988 | 8605 |
| 138 | | 46150 | 85427 | 10181 | 10613 |
| 139 | | 48080 | 83497 | 12757 | 6971 |
| 140 | | 43804 | 87773 | 11373 | 11609 |
| 141 | | 45575 | 86002 | 11102 | 9298 |
| 142 | | 45321 | 86256 | 10997 | 9291 |
| 143 | | 45177 | 86400 | 11481 | 7816 |
| 144 | | 43090 | 88487 | 8871 | 9371 |
| 145 | | 45190 | 86387 | 9909 | 10369 |
| 146 | | 47274 | 84303 | 7169 | 8117 |
| 147 | | 49863 | 81714 | 11984 | 7030 |
| 148 | | 46559 | 85018 | 8863 | 5573 |
| 149 | | 44935 | 86642 | 11487 | 8142 |

TABLE 5-continued

The statistics at each step of the polling process for the second consensus

| Step | SEQ ID NO:30) Consensus (omitted after | Accepted size | Rejected size | Newly rejected | Newly returned |
|---|---|---|---|---|---|
| 150 | | 43294 | 88283 | 9948 | 7906 |
| 151 | | 42987 | 88590 | 10490 | 8716 |
| 152 | | 42979 | 88598 | 12730 | 7147 |
| 153 | | 39175 | 92402 | 8404 | 8161 |
| 154 | | 40737 | 90840 | 9084 | 12699 |
| 155 | | 46171 | 85406 | 12976 | 6695 |
| 156 | | 41755 | 89822 | 9695 | 10354 |
| 157 | | 44312 | 87265 | 11377 | 9028 |
| 158 | | 43893 | 87684 | 6598 | 8552 |
| 159 | | 47802 | 83775 | 15583 | 6781 |
| 160 | | 40975 | 90602 | 7927 | 6816 |
| 161 | | 41862 | 89715 | 13086 | 12534 |
| 162 | | 43342 | 88235 | 9618 | 6643 |
| 163 | | 42523 | 89054 | 11889 | 10580 |
| 164 | | 43452 | 88125 | 9853 | 8209 |

Example 7

Run the Polling Algorithm on the First 100 Reads from the Data Set

This example took only the first 100 reads with 762 subreads from the data set as the input. The process stopped when terminated subreads changed from 13 to 134. The consensus generated matched perfectly to the amplicon sequence and representing 199 sequences.

TABLE 6

The statistics at each step of the polling process for the first consensus from 100 reads

| Step | SEQ ID NO:30) Consensus (omitted after | Accepted size | Rejected size | Newly rejected | Newly returned |
|---|---|---|---|---|---|
| 1 | — C | 762 | 0 | 259 | 0 |
| 2 | — CT | 503 | 259 | 129 | 0 |
| 3 | — CTG | 374 | 388 | 180 | 59 |
| 4 | 22 CTGC | 253 | 509 | 62 | 47 |
| 5 | 19 CTGCG | 238 | 524 | 49 | 226 |
| 6 | 23 CTGCGG | 415 | 347 | 212 | 102 |
| 7 | 24 CTGCGGA | 305 | 457 | 78 | 40 |
| 8 | 25 CTGCGGAA | 267 | 495 | 48 | 57 |
| 9 | 26 CTGCGGAAC | 276 | 486 | 79 | 50 |
| 10 | 27 CTGCGGAACC | 247 | 515 | 58 | 127 |

TABLE 6-continued

The statistics at each step of the polling process for the first consensus from 100 reads

| Step | SEQ ID NO: | Consensus (omitted after 30) | Accepted size | Rejected size | Newly rejected | Newly returned |
|---|---|---|---|---|---|---|
| 11 | 28 | CTGCGGAACCG | 316 | 446 | 126 | 99 |
| 12 | 29 | CTGCGGAACCGG | 289 | 473 | 101 | 70 |
| 13 | 30 | CTGCGGAACCGGT | 258 | 504 | 75 | 55 |
| 14 | 31 | CTGCGGAACCGGTG | 238 | 524 | 41 | 62 |
| 15 | 32 | CTGCGGAACCGGTGA | 259 | 503 | 52 | 64 |
| 16 | 33 | CTGCGGAACCGGTGAG | 271 | 491 | 59 | 65 |
| 17 | 34 | CTGCGGAACCGGTGAGT | 277 | 485 | 76 | 52 |
| 18 | 35 | CTGCGGAACCGGTGAGTA | 253 | 509 | 48 | 52 |
| 19 | 36 | CTGCGGAACCGGTGAGTAC | 257 | 505 | 61 | 68 |
| 20 | 37 | CTGCGGAACCGGTGAGTACA | 264 | 498 | 65 | 136 |
| 21 | 38 | CTGCGGAACCGGTGAGTACAC | 335 | 427 | 146 | 50 |
| 22 | 39 | CTGCGGAACCGGTGAGTACACC | 239 | 523 | 71 | 72 |
| 23 | 40 | CTGCGGAACCGGTGAGTACACCG | 240 | 522 | 104 | 74 |
| 24 | 41 | CTGCGGAACCGGTGAGTACACCGG | 210 | 552 | 56 | 60 |
| 25 | 42 | CTGCGGAACCGGTGAGTACACCGGA | 214 | 548 | 49 | 62 |
| 26 | 43 | CTGCGGAACCGGTGAGTACACCGGAA | 227 | 535 | 29 | 79 |
| 27 | 44 | CTGCGGAACCGGTGAGTACACCGGAAT | 277 | 485 | 90 | 46 |
| 28 | 45 | CTGCGGAACCGGTGAGTACACCGGAATT | 233 | 529 | 34 | 39 |
| 29 | 46 | CTGCGGAACCGGTGAGTACACCGGAATTG | 238 | 524 | 55 | 48 |
| 30 | 47 | CTGCGGAACCGGTGAGTACACCGGAATTGC | 231 | 531 | 44 | 93 |
| 31 | | | 280 | 482 | 83 | 97 |
| 32 | | | 294 | 468 | 117 | 83 |
| 33 | | | 260 | 502 | 71 | 70 |
| 34 | | | 259 | 503 | 55 | 92 |
| 35 | | | 296 | 466 | 93 | 27 |
| 36 | | | 230 | 532 | 45 | 50 |
| 37 | | | 235 | 527 | 63 | 84 |
| 38 | | | 256 | 506 | 79 | 57 |
| 39 | | | 234 | 528 | 63 | 55 |

TABLE 6-continued

The statistics at each step of the polling process for the first consensus from 100 reads

| Step | SEQ ID NO Consensus (omitted after :30) | Accepted size | Rejected size | Newly rejected | Newly returned |
|---|---|---|---|---|---|
| 40 | | 226 | 536 | 57 | 111 |
| 41 | | 280 | 482 | 140 | 60 |
| 42 | | 200 | 562 | 29 | 62 |
| 43 | | 233 | 529 | 67 | 65 |
| 44 | | 231 | 531 | 69 | 27 |
| 45 | | 189 | 573 | 40 | 73 |
| 46 | | 222 | 540 | 70 | 77 |
| 47 | | 229 | 533 | 66 | 98 |
| 48 | | 261 | 501 | 69 | 72 |
| 49 | | 264 | 498 | 43 | 50 |
| 50 | | 271 | 491 | 62 | 26 |
| 51 | | 235 | 527 | 46 | 65 |
| 52 | | 254 | 508 | 70 | 62 |
| 53 | | 246 | 516 | 41 | 36 |
| 54 | | 242 | 520 | 38 | 45 |
| 55 | | 250 | 512 | 55 | 28 |
| 56 | | 224 | 538 | 41 | 101 |
| 57 | | 285 | 477 | 76 | 52 |
| 58 | | 262 | 500 | 57 | 55 |
| 59 | | 261 | 501 | 58 | 23 |
| 60 | | 227 | 535 | 49 | 53 |
| 61 | | 232 | 530 | 33 | 90 |
| 62 | | 290 | 472 | 98 | 44 |
| 63 | | 237 | 525 | 89 | 53 |
| 64 | | 202 | 560 | 54 | 98 |
| 65 | | 247 | 515 | 78 | 70 |
| 66 | | 240 | 522 | 46 | 39 |
| 67 | | 234 | 528 | 43 | 66 |
| 68 | | 258 | 504 | 85 | 72 |
| 69 | | 246 | 516 | 88 | 37 |
| 70 | | 196 | 566 | 27 | 67 |
| 71 | | 237 | 525 | 40 | 86 |
| 72 | | 284 | 478 | 76 | 64 |
| 73 | | 273 | 489 | 95 | 58 |
| 74 | | 237 | 525 | 58 | 47 |
| 75 | | 227 | 535 | 32 | 71 |

TABLE 6-continued

The statistics at each step of the polling process for the first consensus from 100 reads

| Step | SEQ ID NO:30) Consensus (omitted after | Accepted size | Rejected size | Newly rejected | Newly returned |
|---|---|---|---|---|---|
| 76 |  | 267 | 495 | 79 | 40 |
| 77 |  | 229 | 533 | 38 | 76 |
| 78 |  | 268 | 494 | 77 | 50 |
| 79 |  | 243 | 519 | 57 | 27 |
| 80 |  | 215 | 547 | 20 | 62 |
| 81 |  | 259 | 503 | 56 | 50 |
| 82 |  | 255 | 507 | 54 | 19 |
| 83 |  | 222 | 540 | 15 | 43 |
| 84 |  | 252 | 510 | 53 | 50 |
| 85 |  | 251 | 511 | 70 | 28 |
| 86 |  | 211 | 551 | 49 | 88 |
| 87 |  | 252 | 510 | 77 | 73 |
| 88 |  | 250 | 512 | 63 | 36 |
| 89 |  | 225 | 537 | 39 | 39 |
| 90 |  | 227 | 535 | 23 | 96 |
| 91 |  | 302 | 460 | 85 | 62 |
| 92 |  | 281 | 481 | 82 | 28 |
| 93 |  | 229 | 533 | 100 | 31 |
| 94 |  | 162 | 600 | 54 | 46 |
| 95 |  | 156 | 606 | 32 | 110 |
| 96 |  | 236 | 526 | 66 | 56 |
| 97 |  | 228 | 534 | 52 | 92 |
| 98 |  | 270 | 492 | 78 | 57 |
| 99 |  | 252 | 510 | 70 | 48 |
| 100 |  | 233 | 529 | 51 | 51 |
| 101 |  | 236 | 526 | 56 | 41 |
| 102 |  | 224 | 538 | 55 | 51 |
| 103 |  | 223 | 539 | 54 | 72 |
| 104 |  | 244 | 518 | 77 | 45 |
| 105 |  | 215 | 547 | 49 | 61 |
| 106 |  | 230 | 532 | 54 | 54 |
| 107 |  | 233 | 529 | 54 | 47 |
| 108 |  | 229 | 533 | 49 | 60 |
| 109 |  | 243 | 519 | 83 | 49 |
| 110 |  | 213 | 549 | 30 | 37 |
| 111 |  | 224 | 538 | 55 | 49 |
| 112 |  | 222 | 540 | 39 | 28 |

TABLE 6-continued

The statistics at each step of the polling process for the first consensus from 100 reads

| Step | SEQ ID NO: Consensus (omitted after 30) | Accepted size | Rejected size | Newly rejected | Newly returned |
|---|---|---|---|---|---|
| 113 | | 215 | 547 | 50 | 55 |
| 114 | | 224 | 538 | 43 | 38 |
| 115 | | 223 | 539 | 45 | 37 |
| 116 | | 219 | 543 | 40 | 33 |
| 117 | | 216 | 546 | 37 | 40 |
| 118 | | 224 | 538 | 36 | 80 |
| 119 | | 273 | 489 | 86 | 35 |
| 120 | | 227 | 535 | 23 | 38 |
| 121 | | 247 | 515 | 48 | 36 |
| 122 | | 240 | 522 | 91 | 9 |
| 123 | | 163 | 599 | 27 | 73 |
| 124 | | 214 | 548 | 53 | 90 |
| 125 | | 256 | 506 | 50 | 29 |
| 126 | | 240 | 522 | 43 | 53 |
| 127 | | 256 | 506 | 53 | 40 |
| 128 | | 249 | 513 | 58 | 45 |
| 129 | | 242 | 520 | 72 | 30 |
| 130 | | 206 | 556 | 62 | 17 |
| 131 | | 167 | 595 | 34 | 72 |
| 132 | | 211 | 551 | 49 | 64 |
| 133 | | 232 | 530 | 71 | 67 |
| 134 | | 234 | 528 | 86 | 37 |
| 135 | | 193 | 569 | 36 | 51 |
| 136 | | 216 | 546 | 49 | 54 |
| 137 | | 229 | 533 | 46 | 29 |
| 138 | | 220 | 542 | 32 | 29 |
| 139 | | 225 | 537 | 35 | 47 |
| 140 | | 246 | 516 | 65 | 23 |
| 141 | | 213 | 549 | 34 | 34 |
| 142 | | 222 | 540 | 72 | 54 |
| 143 | | 213 | 549 | 54 | 31 |
| 144 | | 199 | 563 | 62 | 53 |
| 145 | | 199 | 563 | 47 | 43 |
| 146 | | 204 | 558 | 57 | 74 |
| 147 | | 230 | 532 | 77 | 37 |
| 148 | | 199 | 563 | 31 | 34 |

TABLE 6-continued

The statistics at each step of the polling process for the first consensus from 100 reads

| Step | SEQ ID NO: Consensus (omitted after 30) | Accepted size | Rejected size | Newly rejected | Newly returned |
|---|---|---|---|---|---|
| 149 | | 211 | 551 | 36 | 60 |
| 150 | | 244 | 518 | 76 | 27 |
| 151 | | 204 | 558 | 42 | 26 |
| 152 | | 198 | 564 | 35 | 55 |
| 153 | | 228 | 534 | 30 | 43 |
| 154 | | 251 | 511 | 53 | 31 |
| 155 | | 239 | 523 | 71 | 18 |
| 156 | | 196 | 566 | 40 | 31 |
| 157 | | 197 | 565 | 48 | 52 |
| 158 | | 211 | 551 | 52 | 36 |
| 159 | | 205 | 557 | 41 | 54 |
| 160 | | 228 | 534 | 52 | 22 |
| 161 | | 208 | 554 | 43 | 32 |
| 162 | | 207 | 555 | 45 | 42 |
| 163 | | 214 | 548 | 46 | 49 |
| 164 | | 227 | 535 | 67 | 39 |

Example 8

Generating the Second Consensus from the First 100 Reads from the Data Set

This example started with 550 subreads left from example 6. The process stopped when terminated subreads changed from 9 to 102. The sequence generated matched perfectly to the reverse strand of the amplicon sequence, representing 174 sequences.

TABLE 7

The statistics at each step of the polling process for the second consensus from 100 reads

| Step | SEQ ID NO: Consensus (omitted after 30) | Accepted size | Rejected size | Newly rejected | Newly returned |
|---|---|---|---|---|---|
| 1 | — C | 550 | 0 | 203 | 0 |
| 2 | — CT | 347 | 203 | 99 | 0 |
| 3 | — CTC | 248 | 302 | 109 | 78 |
| 4 | 48 CTCG | 217 | 333 | 56 | 45 |
| 5 | 49 CTCGC | 206 | 344 | 36 | 132 |
| 6 | 50 CTCGCA | 302 | 248 | 124 | 43 |
| 7 | 51 CTCGCAA | 221 | 329 | 68 | 55 |
| 8 | 52 CTCGCAAG | 208 | 342 | 66 | 36 |
| 9 | 53 CTCGCAAGC | 178 | 372 | 36 | 66 |

TABLE 7-continued

The statistics at each step of the polling process for the second consensus from 100 reads

| Step | SEQ ID NO: | Consensus (omitted after 30) | Accepted size | Rejected size | Newly rejected | Newly returned |
|---|---|---|---|---|---|---|
| 10 | 54 | CTCGCAAGCA | 208 | 342 | 45 | 86 |
| 11 | 55 | CTCGCAAGCAC | 249 | 301 | 79 | 34 |
| 12 | 56 | CTCGCAAGCACC | 204 | 346 | 38 | 66 |
| 13 | 57 | CTCGCAAGCACCC | 232 | 318 | 81 | 42 |
| 14 | 58 | CTCGCAAGCACCCT | 193 | 357 | 57 | 36 |
| 15 | 59 | CTCGCAAGCACCCTA | 172 | 378 | 36 | 63 |
| 16 | 60 | CTCGCAAGCACCCTAT | 199 | 351 | 54 | 39 |
| 17 | 61 | CTCGCAAGCACCCTATC | 184 | 366 | 18 | 57 |
| 18 | 62 | CTCGCAAGCACCCTATCA | 223 | 327 | 76 | 60 |
| 19 | 63 | CTCGCAAGCACCCTATCAG | 207 | 343 | 30 | 32 |
| 20 | 64 | CTCGCAAGCACCCTATCAGG | 209 | 341 | 41 | 94 |
| 21 | 65 | CTCGCAAGCACCCTATCAGGC | 262 | 288 | 104 | 47 |
| 22 | 66 | CTCGCAAGCACCCTATCAGGCA | 205 | 345 | 73 | 35 |
| 23 | 67 | CTCGCAAGCACCCTATCAGGCAG | 167 | 383 | 31 | 60 |
| 24 | 68 | CTCGCAAGCACCCTATCAGGCAGT | 196 | 354 | 44 | 59 |
| 25 | 69 | CTCGCAAGCACCCTATCAGGCAGTA | 211 | 339 | 56 | 59 |
| 26 | 70 | CTCGCAAGCACCCTATCAGGCAGTAC | 214 | 336 | 44 | 50 |
| 27 | 71 | CTCGCAAGCACCCTATCAGGCAGTACC | 220 | 330 | 68 | 53 |
| 28 | 72 | CTCGCAAGCACCCTATCAGGCAGTACCA | 205 | 345 | 69 | 36 |
| 29 | 73 | CTCGCAAGCACCCTATCAGGCAGTACCAC | 172 | 378 | 48 | 65 |
| 30 | 74 | CTCGCAAGCACCCTATCAGGCAGTACCACA | 189 | 361 | 53 | 44 |
| 31 | | | 180 | 370 | 51 | 52 |
| 32 | | | 181 | 369 | 45 | 36 |
| 33 | | | 172 | 378 | 29 | 77 |
| 34 | | | 220 | 330 | 57 | 56 |
| 35 | | | 219 | 331 | 65 | 40 |
| 36 | | | 194 | 356 | 56 | 22 |
| 37 | | | 160 | 390 | 8 | 49 |
| 38 | | | 201 | 349 | 45 | 32 |

TABLE 7-continued

The statistics at each step of the polling process for the second consensus from 100 reads

| Step | SEQ ID Consensus (omitted after NO:30) | Accepted size | Rejected size | Newly rejected | Newly returned |
|---|---|---|---|---|---|
| 39 | | 188 | 362 | 51 | 21 |
| 40 | | 158 | 392 | 30 | 68 |
| 41 | | 196 | 354 | 51 | 66 |
| 42 | | 211 | 339 | 55 | 39 |
| 43 | | 195 | 355 | 45 | 64 |
| 44 | | 214 | 336 | 60 | 39 |
| 45 | | 193 | 357 | 36 | 36 |
| 46 | | 194 | 356 | 69 | 34 |
| 47 | | 161 | 389 | 50 | 23 |
| 48 | | 136 | 414 | 37 | 69 |
| 49 | | 170 | 380 | 55 | 53 |
| 50 | | 170 | 380 | 43 | 41 |
| 51 | | 170 | 380 | 37 | 37 |
| 52 | | 172 | 378 | 39 | 36 |
| 53 | | 171 | 379 | 39 | 36 |
| 54 | | 170 | 380 | 33 | 51 |
| 55 | | 190 | 360 | 43 | 29 |
| 56 | | 178 | 372 | 44 | 31 |
| 57 | | 167 | 383 | 40 | 42 |
| 58 | | 171 | 379 | 29 | 64 |
| 59 | | 208 | 342 | 69 | 57 |
| 60 | | 198 | 352 | 59 | 41 |
| 61 | | 182 | 368 | 34 | 32 |
| 62 | | 182 | 368 | 36 | 41 |
| 63 | | 189 | 361 | 54 | 40 |
| 64 | | 177 | 373 | 48 | 57 |
| 65 | | 188 | 362 | 52 | 50 |
| 66 | | 188 | 362 | 46 | 27 |
| 67 | | 171 | 379 | 36 | 43 |
| 68 | | 180 | 370 | 53 | 31 |
| 69 | | 160 | 390 | 28 | 30 |
| 70 | | 164 | 386 | 41 | 57 |
| 71 | | 182 | 368 | 55 | 37 |
| 72 | | 166 | 384 | 28 | 56 |
| 73 | | 196 | 354 | 34 | 65 |
| 74 | | 229 | 321 | 36 | 25 |

TABLE 7-continued

The statistics at each step of the polling process for the second consensus from 100 reads

| Step | SEQ ID NO: Consensus (omitted after 30) | Accepted size | Rejected size | Newly rejected | Newly returned |
|---|---|---|---|---|---|
| 75 | | 220 | 330 | 35 | 20 |
| 76 | | 207 | 343 | 53 | 18 |
| 77 | | 174 | 376 | 64 | 14 |
| 78 | | 126 | 424 | 32 | 56 |
| 79 | | 152 | 398 | 35 | 71 |
| 80 | | 190 | 360 | 41 | 41 |
| 81 | | 192 | 358 | 39 | 44 |
| 82 | | 199 | 351 | 25 | 42 |
| 83 | | 218 | 332 | 80 | 24 |
| 84 | | 164 | 386 | 33 | 20 |
| 85 | | 153 | 397 | 22 | 97 |
| 86 | | 230 | 320 | 70 | 20 |
| 87 | | 182 | 368 | 46 | 17 |
| 88 | | 155 | 395 | 22 | 63 |
| 89 | | 198 | 352 | 48 | 41 |
| 90 | | 193 | 357 | 31 | 35 |
| 91 | | 199 | 351 | 48 | 43 |
| 92 | | 196 | 354 | 54 | 20 |
| 93 | | 164 | 386 | 23 | 44 |
| 94 | | 187 | 363 | 39 | 65 |
| 95 | | 215 | 335 | 62 | 35 |
| 96 | | 190 | 360 | 45 | 29 |
| 97 | | 176 | 374 | 44 | 38 |
| 98 | | 172 | 378 | 27 | 40 |
| 99 | | 187 | 363 | 38 | 50 |
| 100 | | 201 | 349 | 37 | 38 |
| 101 | | 204 | 346 | 47 | 40 |
| 102 | | 199 | 351 | 52 | 46 |
| 103 | | 195 | 355 | 49 | 51 |
| 104 | | 199 | 351 | 35 | 51 |
| 105 | | 217 | 333 | 52 | 36 |
| 106 | | 203 | 347 | 45 | 16 |
| 107 | | 176 | 374 | 11 | 57 |
| 108 | | 224 | 326 | 40 | 30 |
| 109 | | 216 | 334 | 72 | 12 |
| 110 | | 159 | 391 | 33 | 34 |
| 111 | | 163 | 387 | 26 | 70 |

TABLE 7-continued

The statistics at each step of the polling process for the second consensus from 100 reads

| Step | SEQ ID NO: Consensus (omitted after 30) | Accepted size | Rejected size | Newly rejected | Newly returned |
|---|---|---|---|---|---|
| 112 | | 210 | 340 | 38 | 41 |
| 113 | | 216 | 334 | 55 | 36 |
| 114 | | 200 | 350 | 54 | 34 |
| 115 | | 183 | 367 | 40 | 45 |
| 116 | | 191 | 359 | 43 | 38 |
| 117 | | 189 | 361 | 26 | 47 |
| 118 | | 213 | 337 | 63 | 27 |
| 119 | | 180 | 370 | 45 | 13 |
| 120 | | 152 | 398 | 15 | 74 |
| 121 | | 215 | 335 | 49 | 43 |
| 122 | | 213 | 337 | 52 | 23 |
| 123 | | 188 | 362 | 32 | 50 |
| 124 | | 210 | 340 | 74 | 34 |
| 125 | | 174 | 376 | 56 | 32 |
| 126 | | 154 | 396 | 38 | 74 |
| 127 | | 194 | 356 | 53 | 38 |
| 128 | | 183 | 367 | 24 | 31 |
| 129 | | 194 | 356 | 50 | 51 |
| 130 | | 199 | 351 | 37 | 46 |
| 131 | | 212 | 338 | 53 | 28 |
| 132 | | 191 | 359 | 53 | 25 |
| 133 | | 167 | 383 | 39 | 52 |
| 134 | | 185 | 365 | 36 | 47 |
| 135 | | 201 | 349 | 37 | 33 |
| 136 | | 202 | 348 | 45 | 24 |
| 137 | | 186 | 364 | 33 | 34 |
| 138 | | 192 | 358 | 54 | 43 |
| 139 | | 186 | 364 | 41 | 18 |
| 140 | | 168 | 382 | 31 | 50 |
| 141 | | 192 | 358 | 42 | 36 |
| 142 | | 191 | 359 | 52 | 38 |
| 143 | | 182 | 368 | 48 | 25 |
| 144 | | 164 | 386 | 27 | 38 |
| 145 | | 180 | 370 | 45 | 53 |
| 146 | | 193 | 357 | 23 | 27 |
| 147 | | 203 | 347 | 53 | 46 |

TABLE 7-continued

The statistics at each step of the polling process for the second consensus from 100 reads

| Step | SEQ ID Consensus (omitted after NO:30) | Accepted size | Rejected size | Newly rejected | Newly returned |
|---|---|---|---|---|---|
| 148 | | 202 | 348 | 35 | 20 |
| 149 | | 193 | 357 | 58 | 29 |
| 150 | | 170 | 380 | 33 | 25 |
| 151 | | 168 | 382 | 27 | 41 |
| 152 | | 188 | 362 | 54 | 25 |
| 153 | | 165 | 385 | 35 | 26 |
| 154 | | 162 | 388 | 34 | 52 |
| 155 | | 186 | 364 | 46 | 36 |
| 156 | | 182 | 368 | 48 | 41 |
| 157 | | 181 | 369 | 45 | 26 |
| 158 | | 168 | 382 | 23 | 44 |
| 159 | | 195 | 355 | 69 | 23 |
| 160 | | 155 | 395 | 28 | 24 |
| 161 | | 157 | 393 | 37 | 64 |
| 162 | | 190 | 360 | 42 | 25 |
| 163 | | 179 | 371 | 50 | 35 |
| 164 | | 171 | 379 | 34 | 37 |

The examples and embodiments described herein are for illustrative purposes only. Various modifications or changes thereof are apparent and are included within the spirit and purview of this application and scope of the appended claims. All publications, patents, patent applications, web sites, accession numbers and the like cited herein are hereby incorporated by reference in their entirety for all purposes. If different versions of any such citation are available, the most recent version at the effective filing date of the present application, the effective filing date meaning the filing date of the earliest priority application disclosing the sequence. Unless otherwise apparent from the context, any embodiment, aspect, step, feature, element or the like can be used in combination with any other.

What is claimed is:

1. A method of developing a consensus sequence from a plurality of sequencing reads of a nucleic acid target, comprising:
   (i) ligating a target nucleic acid and an anchor segment of known sequence and thereby forming a nucleic acid target template, which is a circular molecule in which the target nucleic acid forms an adjacent segment adjacent the anchor segment,
   (ii) generating raw target sequencing reads by synthesis directed by a polymerase reading around the nucleic acid target template multiple times primed from a primer binding to the anchor segment, the raw target sequencing reads comprise alternating reads of the anchor segment and the target nucleic acid; and at least some of the raw target sequencing reads containing sequencing errors;
   (iii) performing the following computer-implemented steps:
   (a) receiving a population of raw target sequencing reads of the nucleic acid target template ;
   (b) evaluating the accuracy of sequencing of the anchor segment in different raw target sequencing reads by comparing raw target sequencing reads of the anchor segment with the known sequence of the anchor segment;
   (c) assigning a subset of the raw target sequencing reads into an accepted class based on reaching at least a threshold level of accuracy of the sequencing of the anchor segment;
   (d) polling nucleobases at a position equidistant to the anchor segment sequence in raw target sequencing reads in the accepted class to determine a consensus nucleobase, which consensus nucleobase is assigned as the first nucleobase of a nascent sequence of the adjacent segment;
   (e) assigning raw target sequencing reads having the consensus nucleobase determined in the prior polling step to remain in the accepted class and assigning raw target sequencing reads lacking the consensus nucleobase determined in the prior polling step to a rejected class;
   (f) optionally reassigning a raw target sequencing read from the rejected class to the accepted class by scoring similarity of the raw target sequencing read to the nascent sequence and reintroducing the raw target sequencing read if the sequence similarity reaches at least a threshold level of similarity; and
   (g) repeating steps (d), (e) and optionally (f), except that a repetition polls a position adjacent the position poled in the previous polling step for raw target sequencing reads having the consensus nucleobase polled in the previous step or in the case of a raw target sequencing read reassigned from the rejected class to the accepted class and not polled in the previous polling step or if polled and not having the consensus nucleobase in the previous polling step, the polling polls a position adjacent the position aligned with the last nucleobase of the nascent sequence to determine a consensus nucleobase, and the consensus nucleobases determined in successive repetitions are assigned as successive nucleobases in the nascent sequence of the adjacent segment; wherein step (f) is performed at least once.

2. The method of claim 1, wherein step (g) is performed at least 20 times and step (f) at least 5 times.

3. The method of claim 1, wherein step (g) is performed at least 100 times and step (f) at least 20 times.

4. The method of claim 1, wherein the threshold for step (f) is at least 80% identity between the raw target sequencing read and nascent sequence when maximally aligned and a match between the last assigned nucleobase of the nascent sequence and corresponding nucleobase of the raw targeting sequencing read.

5. The method of claim 1, wherein the threshold level of accuracy of the sequencing the anchor segment is based on percentage of sequence identity and/or location of matched nucleobases between a raw target sequencing read and the known anchor segment.

6. The method of claim 1, wherein the threshold level of accuracy requires a raw target sequencing read to have the correct nucleobase corresponding to the nucleobase of the anchor segment immediately adjacent the adjacent segment.

7. The method of claim 1, wherein the nucleic acid target template includes a nucleobase variation at a position and when step (g) polls the position it determines two consensus nucleobases for the position, wherein the nascent sequence is branched into two nascent sequences differing between the two consensus nucleobases and the consensus nucleobase determined in further repetitions of step (g) is assigned to both nascent sequences.

8. The method of any of claims 1 wherein the nucleic acid target template comprises first and second anchor segments at opposing ends of the nucleic acid target template and the raw target sequencing reads include a first group of raw target sequencing reads of the first anchor segment and an adjacent target nucleic acid segment and a second group of raw target sequencing reads of the second anchor segment and an adjacent segment; the first and second groups being raw sequencing reads of opposing strands of the nucleic acid target template and the method is performed on the first and second groups of raw target sequencing reads to determine consensus sequences of opposing strands of the target nucleic acid template.

9. The method of claim 1, wherein the raw sequencing reads comprise raw sequencing reads of first and second nucleic acid target templates, the first nucleic acid target template comprising the anchor segment linked to a first adjacent segment and the second nucleic acid target template comprising the anchor segment linked to a second adjacent segment.

10. The method of claim 9, wherein the first and second adjacent segments are overlapping segments.

11. The method of claim 10, wherein the first and second adjacent segments are fragments of the same contiguous polynucleotide.

12. The method of claim 9, wherein the first and second adjacent segments are nonoverlapping segments.

13. The method of claim 1, wherein the raw sequencing reads comprising raw sequence reads of a plurality of nucleic acid target templates, the different nucleic acid targets templates comprising the anchor segment linked to different adjacent segments; the different adjacent segments including overlapping and nonoverlapping segments.

14. The method of claim 1, wherein a strand of the anchor segment is a primer or primer binding site incorporated into the nucleic acid target template.

15. The method of claim 1, wherein a strand of the anchor segment has 4-120 nucleobases.

16. The method of claim 1, further comprising experimentally determining the population of raw target sequencing reads of the target nucleic acid.

17. The method of claim 1, further comprising, designating a segment of the nascent sequence of the adjacent segment as a new anchor segment and repeating the method to determine a consensus sequence of an adjacent segment adjacent the new anchor segment.

18. A method of developing a consensus sequence from a plurality of sequencing reads of a nucleic acid target, comprising:
(i) ligating a target nucleic acid of unknown sequence to a hairpin structure of known sequence to a form a circular nucleic acid target template in which the target nucleic acid forms an adjacent segment adjacent an anchor segment of known sequence:
(ii) performing sequencing by synthesis by extending a primer bound to the anchor segment with a polymerase reading around the circular nucleic acid target template multiple times to generate a population of raw target sequence reads comprising alternating reads of the anchor segment and the adjacent segment; and at least some of the raw target sequencing reads containing sequencing errors; and
(iii) performing the following computer implemented steps:
(a) receiving the population of raw target sequencing reads generated in step (ii);
(b) evaluating the accuracy of sequencing of the anchor segment in different raw target sequencing reads by comparing raw target sequencing reads of the anchor segment with the known sequence of the anchor segment;
(c) assigning a subset of the raw target sequencing reads into an accepted class based on reaching at least a threshold level of accuracy of the sequencing of the anchor segment;
(d) polling nucleobases at a position equidistant to the anchor segment sequence in raw target sequencing reads in the accepted class to determine a consensus nucleobase, which consensus nucleobase is assigned as the first nucleobase of a nascent sequence of the adjacent segment;
(e) assigning raw target sequencing reads having the consensus nucleobase determined in the prior polling step to remain in the accepted class and assigning raw target sequencing reads lacking the consensus nucleobase determined in the prior polling step to a rejected class;
(f) optionally reassigning a raw target sequencing read from the rejected class to the accepted class by scoring similarity of the raw target sequencing read to the nascent sequence and reintroducing the raw target sequencing read if the sequence similarity reaches at least a threshold level of similarity; and
(g) repeating steps (d), (e) and optionally (f), except that a repetition polls a position adjacent the position poled in the previous polling step for raw target sequencing reads having the consensus nucleobase polled in the previous step or in the case of a raw target sequencing read reassigned from the rejected class to the accepted class and not polled in the previous polling step or if polled and not having the consensus nucleobase in the previous polling step, the polling polls a position adjacent the position aligned with the last nucleobase of the nascent sequence to determine a consensus nucleobase, and the consensus nucleobases determined in successive repetitions are assigned as successive nucleobases in the nascent sequence of the adjacent segment; wherein step (f) is performed at least once (h) outputting the sequence of at least part of the target nucleic acid.

19. The method of claim 18, wherein step (g) is performed at least 20 times and step (f) at least 5 times.

20. The method of claim 18, wherein step (g) is performed at least 100 times and step (f) at least 20 times.

21. The method of claim 18, wherein the threshold for step (f) is at least 80% identity between the raw target sequencing read and nascent sequence when maximally aligned and a match between the last assigned nucleobase of the nascent sequence and corresponding nucleobase of the raw targeting sequencing read.

22. The method of claim 18, wherein the threshold level of accuracy of the sequencing the anchor segment is based on percentage of sequence identity and/or location of matched nucleobases between a raw target sequencing read and the known anchor segment.

23. The method of claim 18, wherein the threshold level of accuracy requires a raw target sequencing read to have the correct nucleobase corresponding to the nucleobase of the anchor segment immediately adjacent the adjacent segment.

24. The method of claim 18, wherein the nucleic acid target template includes a nucleobase variation at a position and when step (g) polls the position it determines two consensus nucleobases for the position, wherein the nascent sequence is branched into two nascent sequences differing between the two consensus nucleobases and the consensus nucleobase determined in further repetitions of step (g) is assigned to both nascent sequences.

25. The method of any of claims 18, wherein the nucleic acid target template comprises first and second anchor segments at opposing ends of the nucleic acid target template and the raw target sequencing reads include a first group of raw target sequencing reads of the first anchor segment and an adjacent segment and a second group of raw target sequencing reads of the second anchor segment and an adjacent segment; the first and second groups being raw sequencing reads of opposing strands of the nucleic acid target template and the method is performed on the first and second groups of raw target sequencing reads to determine consensus sequences of opposing strands of the target nucleic acid template.

26. The method of claim 18, wherein the raw sequencing reads comprise raw sequencing reads of first and second nucleic acid target templates, the first nucleic acid target template comprising the anchor segment linked to a first adjacent segment and the second nucleic acid target template comprising the anchor segment linked to a second adjacent segment.

27. The method of claim 26, wherein the first and second adjacent segments are overlapping segments.

28. The method of claim 27, wherein the first and second adjacent segments are fragments of the same contiguous polynucleotide.

29. The method of claim 26, wherein the first and second adjacent segments are nonoverlapping segments.

30. The method of claim 18, wherein the raw sequencing reads comprising raw sequence reads of a plurality of nucleic acid target templates, the different nucleic acid targets templates comprising the anchor segment linked to different adjacent segments; the different adjacent segments including overlapping and nonoverlapping segments.

31. The method of claim 18, wherein a strand of the anchor segment is a primer or primer binding site incorporated into the nucleic acid target template.

32. The method of claim 18, wherein a strand of the anchor segment has 4-120 nucleobases.

33. The method of claim 18, further comprising experimentally determining the population of raw target sequencing reads of the target nucleic acid.

34. The method of claim 18, further comprising, designating a segment of the nascent sequence of the adjacent segment as a new anchor segment and repeating the method to determine a consensus sequence of an adjacent segment adjacent the new anchor segment.

* * * * *

SEQUENCE LISTING

<160> NUMBER OF SEQ ID NOS: 74

<210> SEQ ID NO 1
<211> LENGTH: 12
<212> TYPE: DNA
<213> ORGANISM: Artificial Sequence
<220> FEATURE:
<223> OTHER INFORMATION: Synthesized

<400> SEQUENCE: 1
cgcggaaacc gg                                                    12

<210> SEQ ID NO 2
<211> LENGTH: 13
<212> TYPE: DNA
<213> ORGANISM: Artificial Sequence
<220> FEATURE:
<223> OTHER INFORMATION: Synthesized

<400> SEQUENCE: 2
cgactgaacc tgg                                                         13

<210> SEQ ID NO 3
<211> LENGTH: 10
<212> TYPE: DNA
<213> ORGANISM: Artificial Sequence
<220> FEATURE:
<223> OTHER INFORMATION: Synthesized

<400> SEQUENCE: 3
ctgcggtgag                                                             10

<210> SEQ ID NO 4
<211> LENGTH: 12
<212> TYPE: DNA
<213> ORGANISM: Artificial Sequence
<220> FEATURE:
<223> OTHER INFORMATION: Synthesized

<400> SEQUENCE: 4
cctgcgaacc gg                                                          12

<210> SEQ ID NO 5
<211> LENGTH: 14
<212> TYPE: DNA
<213> ORGANISM: Artificial Sequence
<220> FEATURE:
<223> OTHER INFORMATION: Synthesized

<400> SEQUENCE: 5
tctgcggaca ccgg                                                        14

<210> SEQ ID NO 6
<211> LENGTH: 14
<212> TYPE: DNA
<213> ORGANISM: Artificial Sequence
<220> FEATURE:
<223> OTHER INFORMATION: Synthesized

<400> SEQUENCE: 6
ctggcggaac acag                                                        14

<210> SEQ ID NO 7
<211> LENGTH: 15
<212> TYPE: DNA
<213> ORGANISM: Artificial Sequence
<220> FEATURE:
<223> OTHER INFORMATION: Synthesized

<400> SEQUENCE: 7
ctttcggaac gcagg                                                       15

<210> SEQ ID NO 8
<211> LENGTH: 15
<212> TYPE: DNA
<213> ORGANISM: Artificial Sequence
<220> FEATURE:
<223> OTHER INFORMATION: Synthesized

<400> SEQUENCE: 8
ctgacggaaa cccgg                                                       15

<210> SEQ ID NO 9
<211> LENGTH: 11
<212> TYPE: DNA
<213> ORGANISM: Artificial Sequence
<220> FEATURE:
<223> OTHER INFORMATION: Synthesized

<400> SEQUENCE: 9

```
ctgcgggacg g                                                          11
```

<210> SEQ ID NO 10
<211> LENGTH: 164
<212> TYPE: DNA
<213> ORGANISM: Hepatitis C virus

<400> SEQUENCE: 10

```
ctgcggaacc ggtgagtaca ccggaattgc caggacgacc gggtcctttc gtggataaac     60
ccgctcaatg cctggagatt tgggcgtgcc cccgcaagac tgctagccga gtagtgttgg    120
gtcgcgaaag gccttgtggt actgcctgat agggtgcttg cgag                     164
```

<210> SEQ ID NO 11
<211> LENGTH: 45
<212> TYPE: DNA
<213> ORGANISM: Artificial Sequence
<220> FEATURE:
<223> OTHER INFORMATION: Synthesized

<400> SEQUENCE: 11

```
atctctctca acaacaacaa cggaggagga ggaaaagaga gagat                     45
```

<210> SEQ ID NO 12
<211> LENGTH: 16
<212> TYPE: DNA
<213> ORGANISM: Artificial Sequence
<220> FEATURE:
<223> OTHER INFORMATION: Synthesized

<400> SEQUENCE: 12

```
aaaaaaaaaa aaaaaa                                                     16
```

<210> SEQ ID NO 13
<211> LENGTH: 482
<212> TYPE: DNA
<213> ORGANISM: Artificial Sequence
<220> FEATURE:
<223> OTHER INFORMATION: Synthesized

<400> SEQUENCE: 13

```
tgcagcaggg cggctgctga gagtgatggt cgcgacactt gactcgcagg gtgacaagaa     60
agcgcctctc ccccattgcc tcttgtaaaa tccacgagaa caagaccgcc atccgaccca    120
aacaaaaacg acactcaaaa aacagccacc aaaaaaacaa gcacagaagc aaccaaaaga    180
aaccaccaac cacacccagg aaaaaaaaaa caaaaaaaaa caaaaaaaaa acaaaaaaaa    240
aaccacaccc acacatcatc tacaaacaac aaaaaagacc gaaaaaaaaa aaagatcgga    300
cccaccacca ataacctata caaccactta agaacgcgca gccaccccca tccacgaaca    360 aaaacacaa cagccaaaga acaccaaaaa aaaaaaacaa aaaaaaaaaa aaaaaaaaa     420 aaaaaaaaaa aaaacaacaa aaaaaaaagc tggacgtgct tgccgaatgc gcggtggcgc    480
tt                                                                   482
```

<210> SEQ ID NO 14
<211> LENGTH: 4664
<212> TYPE: DNA
<213> ORGANISM: Artificial Sequence
<220> FEATURE:

<223> OTHER INFORMATION: Synthesized

<400> SEQUENCE: 14

```
ggccgctctg tccagcgatt cgccgtgtta ccgtaatcgc tcaaggcagc cctcacgctt      60
cagcgcggtg tctgtaggat agatctttcc gagcgacaga gtggacggcc ctcgaagagg     120
actggcccgg cctcgagcct gagatctgcg ttaatggctc ccgatagagt ccgtcggcta     180
gtggttggag ctctcgcgcg ctcctaataa ctcgctgcgc ttcctcgcag cagcaatcta     240
cgcgtccact cttcagctca gactaacaac ctcgcgaaga cggaaggaga agaggcagta     300
tagggatgag gtcatcgcga aggccgcatc tatgcgcgag gaaaccggtg agtaacaccg     360
cgggtgcatc cgtgtattgt atagatctct gtgccgagca ccacaacaac ggaagggtcg     420
ccgttacggg aaaagcagaa acgagaactc ggataaacct ttatcttggc tcattcgcac     480
ggctctcggg acctgcctct cgagatagag gaatatgcgg tagacgcgct cgcgaaagga     540
cctcagcggc attcttttct tacacataca gctctttta ttctgcgcca cgccgacagg     600
tctcccccag atcccttctt caacctaacc agagctacaa gctcttggcg gggaaggcgg     660
cggcgacgcg catctgtaga tacgcggcgg cggtgtatag ttctccgacg cggtacgcgg     720
tcactcctgg catgctcgca agggtgtaac ttagatagct ccgggtttcc cccgacttcc     780
ccaggcctgg cagtaggagt aggcgtcctt tgcgttagat tcttcgtttc tgcctacaaa     840
caaaccacaa acacgccaga tcgaggaatg tgaggaacca cgagccgcaa gaactccatc     900
cgcacgcgcc tacacccgag tactatttgg ttcggggcgt gggtgaccca ttccaccggc     960
ctgtgatcga caggacccct ataggcatct atactctcgg agcctggata tcgtacggtg    1020
gctttggcgg gggtcggacc ggcatatatc tctccatgcg tcatcttaga gcacaggcag    1080
tatttcggta cacagaaaaa ggacgagaca ggacgagtcg tcctgtgcaa ttctggctcg    1140
tagctcacac cggtcagtcc gcagactgct ctctcaacca aacacgagac gcaggtaggt    1200
tatgccaaaa ggaagaccg aggatttcaa actctctggc cggaaccgcg tgggacagtt    1260
caccctttcgg cgcacgccaa tctggcagtg ctattgtcgc aggcgcccgg ggttcatcta    1320
aacggatcgc tcgatatctt aaatcctcgc gctacaatgc cttccggtgg aatgtaactt    1380
caccgtcctt ctggggccag atagcccctc accgccaaga accaaccaac gagggaggag    1440
aaagaactgg acatttaccc agaccgtgtg gatgtgcatc cgcgaccggc ttagatggtc    1500
ctcaaggctg agcctggatt cctgtgtcgg tgcttaatcg cgccgctcac attccttctc    1560
gatatctgga gacaacagga cggaggtagg agggaaaaga gcgagggaag gtccctcgcc    1620
aagcacccta tcaggcagta ccacaggcct ttcgcgaccc aacactactt cgggcaagac    1680
ttctaacgca gtaccttgag tgacggggggc acggtccaaa tctcccaggc attgagcggg    1740
tatccacgaa aaaggacccg gtcgtcctgg caatttccgg tgtctcaccg gttccgcaga    1800
atcttctctc aaacaacaac aacgaggag gaggaaatcg gcaggagaag acgtgcgtgt    1860
ttacacgggt gtgtattaca caccggaatt gccaggacga accctggtcc ttgtcggtga    1920
gtgaatacct ttcggcgtct acacactcgt cactcgagcg agaatctaaa ctaggcagag    1980
gaaagcgtaa ggaagagctc tccaaaagca ccttcctgca ctccgcaacg aacgtgctcg    2040
cttgttgtcg cagctcctgg gaaccactcg ccgaaggcct tcggtgggta ctctcttagg    2100
tcaggtgtgt cgcggttggg aggatcccct ctcaaacatc cacatttgag gcgttttttt    2160
aattcacgga aaaggaccg tcggttccac ccaaattccg ggtgtactca ccggtccccca    2220
gattcttcta ttcaacaaaa aacgagagga accaacggag gaggaggaaa agagagaaga    2280
```

```
tctcgcaagc accctaatca gagcaaggga tacggcgagg aacctacttg gcctttccgc    2340
ggccgaaccc gtggagttaa cccgaattca acacctagga cctggcggct aagcagtctt    2400
gcggggcgca tcgccagata ctaccacgcg ccttgcaacg gttctcacga aggaggaccc    2460
ggtcggtcct gggcaattcc ggtcgtactc acgccgagtg cacgcgatac tcaatgccgt    2520
caacgcaaca agcagaacgg aggccaggga ccgccgtttt gagttagatg agacgaggaa    2580
tctgcggacc ggtgagtaca ccgcataatt cgtgggccat ggatcgacac gctcaaggca    2640
agcatctgat tcgtggaatg gataaaaaga aaaccttctt ccgcaacgct caactgcctg    2700
gcagatttgg ctgacgttca ggcccccagc tcgcacagac actgcctttt cgcgacgcgt    2760
acgtctaccg agtagtcgtt gcgaggcgtt cttggtcggc cgaaggcccc aaactccagg    2820
gttgctcggt tggaagcctg ttttatccac cgaaggaacc gccgtcggtc ctgcatgctc    2880
cgtgataggc tcacgcgctt cctcgggca tgtatggatc tttctccata cacaaagcaa    2940
caagcggaga ggcagggaaa gagagagcta atccccgcaa gcacaccgct atgcggcagt    3000
tgacgcaaga acagagagac agcgggcctt ctcgcttgga cgccaattca cactcagcct    3060
cggctagcaa gtcttgcggg gcacgccacc atctcaggtg cttgcatttg agcggtctga    3120
ttcccactgt atagcgaccc gcgctcgtcc tgggcaattc cgtgtaccccc accggttccg    3180 cagatctctc tcaaccaaca acaaacggag gaggcagggg aaaagagaga gatgctgagg    3240
cggaagccgg tgagtaggcc accggaattg ccaggacgac gccggtcctt tcgtggataa    3300
aacccgctca atgcctgaag ttctgggcgt gcccgcaaga ctgctagccg agttagtgtt    3360
gtggtcgcga aatgggaggc ctgtggtact cggcctgata gggtgcttgc gagatctctc    3420
tcaacaaaca acaacggagg agaggaggaa agagacggca ggatccgcaa gcacccctac    3480
tcaggccagg tacgcacaag gcgctgttcg ccgaacgccc cacacctact ccggctagca    3540
gtcttggcgg ggggcagcgc ccaaatctcc aggcattgag cgggtttaat gccacgaaag    3600
gaccgccggt cgtcctggca attccgcgtg tactcagccg gtttcgcaga tctctcatca    3660
acaacaagca acgcgaggag gaggaaaagg agatgatctg cggacgcgtg aagtacaccg    3720
gaattgccag gacgaccggt ccttcctcgt ggataaacgc ccggcttcca aatgcgctgg    3780
ccagatttgg cggcgatggc ccgcaagact gctagccgag ttagtgttgg gtcgcgaagg    3840
ccttgtggta ctagccgtga gtagggtgct tgccagatc tctctcccaa acaaccaaca    3900
acggaggagg aggaaaaaga gagagatcct cggcaagcac gccttatgca ggccagtacc    3960
acgaaggcct tcgcgacggc ggcaacaact actcggctac aaagactctt gggcgggggg    4020
gcacggccaa atctccaggc attgagcggg tttatccaac gaaaggacgc gcggtcgtcc    4080
tgggcaattc cggtgtagct cacggtttcc gccagaatct gctctcaaca agcaacacgg    4140
aggagggagg aaaaggggg gaaagagaga tctgcggaac cggtgagtac agccggaatt    4200
gccaggacgc aaccggggt cctttcgtgg ataaacccgt caatgcctgg aagaatttgg    4260
gggcgtgccc ccgcaagact cgctaggccg agtagctgtt gggctgcggg cgaaaggcct    4320
tgtggtatct cgcctgatag gcgtcgcctt ggcgagatct ctgctcagcc caacagacag    4380
acggaggcag agaggaaaag agagagaatc ccttcgcaag cacgcctatc aggccagtac    4440
cacaaaggcc tttcgcgagc gcgtcaacac tagcctcgct aagcagtctt ggcgggggggc    4500 agccaaatct cgcaggcatg aggcgggttt atccacgaaa ggaccggtc gtcgctgagc    4560 aattccgggt tagctcaccg gttccgcaga tctctctcaa caacaacaag ccaccaaacg    4620
```

-continued

```
gaggaggagg aaagagagag atctggcgga acgcgtgagt accg                   4664
```

<210> SEQ ID NO 15
<211> LENGTH: 3694
<212> TYPE: DNA
<213> ORGANISM: Artificial Sequence
<220> FEATURE:
<223> OTHER INFORMATION: Synthesized

<400> SEQUENCE: 15

```
ggtggagtac aagccacgga attggccacc gggacgacgc acgcagcacg acccgggtcc    60
atttcgtgga ataacccgct catgcctgga gatttgggcg tgcccccac cccgcaagac    120
tgctgccgag tagtgttggt cgccgaaagc gccttgtggc taagcctgcc gccctgatca   180
agcacgggtg cttgcgagat tcctctcaca acaacaccac ggatgaggag gccaaaagag   240
cagaactctc gccagcaccc tacttcaagg cagtaccacc aaggccttcc gcgacagccc   300
gcaacaccta ctccggccta gccagtcttg aagcgggcgg gcaaggcgcc caacgatcct   360
ccagggcatt ggccgggttt tatcccacga aaggactccg gcgtgcctgg cccattccgt   420
tgtactccac gcggcttccg cagctcctct cctccaaaca accaaccaaa acgaagagg    480
aaggaggcaa aagagagaga tcatgcggaa ccaaggtgag tacaaaccag agaatataac   540
acaaggacag aaccaaaaaa gaagagaacc cattcataat cgatgataac acaaaccgct   600
ccacagacat ataagaaga acgcacgaac acgcggcgcg tcgccaaacg ccaagatagc    660
gagtaagcca atagataaga gagcaaaaca aagtcagaca gagaagacca taatagagat   720
aacaaaaaaa aaaaaaaaa aacataaaag ctgataagag aaaaaaaaga tgctacagag   780
aaaatatcat ctccatcaca caacacaaca cagagaggaa ggaaggaaa agaagaagag    840
aagatacatg cagcacacta aatcaagaga aaaaaaccaa aaaaaagaca agataacaaa   900
aaaaaaaaa aaaaaataca cacaaaaaca ccaaacacac acaacaaaca cacaccaaac    960
aacacacaaa caaaaaaaca aacaaaaaca ccaaaaaaaa agaaaaaaaa aaaaaacaaa   1020
aaacaagac acaaacaaac aacaaaaaac caaacaaaa aacaaaaaa aaacaaaggc    1080
ctttcgccaa aagaaccaca acaactacaa aacagactag aacagatacc atataagcgg   1140
aggagcaaaa gcacaaatac aaaaaatacc aggcatattg aaagacaaag gcgataataa   1200
taaaccacga aaggaccggt cgtaaaacct ggcaatttcc ggcgtgtact caccgttccg   1260
cagatctctc ctcacccaac acaaccggac ggcaggaggc aaaagagaga gagatctgcg   1320
gaaccgcgcg tacaccggaa ttgccagccg gacgaccggc gtccttttcg tggactacac   1380
ccagctcaat ccgcctctgg agatttgggc gtgcccccg ccaaggccgg acggaccact    1440
gctagccgag tcagtgtgat ggggcgcctc tggccctccg gcccttttggc ggggcgggtt   1500
tgccttccga ccgtggacgg gtcgccgaaa ggccgccgtg tgctcggtca ctccgccgcc   1560
tgaaataggc gctgggcttg gggagatctt ctcctcaacg cgtccgtctg gcaattcggg   1620
tgggcgcccc gggagcggga gtgacgcgca ggaaagagag agcgctctgc atgccgcccc   1680
tattccccag gcgagggcgc gacagagaag ggccgctgtg ttctgctgcg gccacgagca   1740
tactgcggcc tatgtagtcg tggcggggcg cccagatctc ccaggcattg agcgggttat   1800
ccacgaagct tatctcccgt cgtggccttg gccaacgccc ttccggtgta ctcatctggg   1860
tgacggcgat ctcgcgccac gccattataa gagcggcagg agggagacgc gccgagagca   1920
tgctgctgga accgctgagc gcgttaacag ccggagtttt ctgtgcctag acgggctgt    1980
cgagaccgtg gtcctttgtc gtcgctacat acccgctcaa tgccttcgga gattggtggg   2040
```

```
cgtctgccgg cccgcgaagg cacgggcctc tccggaggta agccgctgtg gtgggattcg    2100
cgaaagggcc ttgtggtact ggcctgatag cgcgtttccg cgcttgcgcg agcgatctcg    2160
tctgcgaaca taaccaaaac ggggaggcgg cggcggaaca gagagagcag agtcctgcgc    2220 gccccctct cacccggtcg cggcgcggcg atcgatgcac cacaggcgcc gctttcgcgg     2280
cccaacatct cactactgcg cgctagcgct ctgtgcggcg gctatactgt ccaagatgcg    2340
tcctaccggg caggccgccg cccggcacca gtcgcagcat cctggagccc gcgggtttca    2400
gtccacggca gcaggtggac gcccccgggc tcgtggccct cgcgactctc cgggtacgca    2460
cccggttccg gcaggatccc tccatcagcg cgggccgggc gccggccaca acagacgggg    2520
ccgcggcagg aagggccggg acccaagaag agagagatct gcggaaccgg tgagtacacg    2580
gaattgccag gacgaccggg tccttcgtgg ataaacgctc gcttcaatgc ctggagattt    2640
tgggcgtgcc ccgaactgct agccgagtag tgttgggctc gcgaagccct tgtgggtact    2700
ccgcctgata ggcgtgcctt gcgagatctc tctcaacaac aagcaagcgg aggaaggagg    2760
gaaaagaaag gagatcgctc cggcaaggca ccctaatcag gcagtaccac gagagggcct    2820
ttcgcgacca agcactactc gcgctagcag tctttgcggg ggcacgccaa atcctccgag    2880
aggcatctga gggcgggttt attccaacga aaggacccgg tcgtcgcctg gcaattcccc    2940
ggtgtagatc acgcgtttcg cgggcagaat tctctctcac aacgacagca acggagagag    3000
caaaagaaga gagatcgtgg cggaaccggt gagtacaccc ggaattggca ggaacgaccg    3060
gtcctttcgt ggataaaccc cgtccaatgc cgtcggagaa tttgggcgtg cccgcaagac    3120
tgcttaggcc gagtagtgtt ggtcgccgaa aggccttgtt tgtgactcgc ctgatagggt    3180
gcttgcgggg atgctctctc caaacaaggc acacggagga gggaggcaaa agagagagat    3240
cttcgcaagc ccgagcctat caagtggcgc agtacccaac aaggcttcgg cgagcccacc    3300
aacactactc gggctaggca gtccttgcgg ggcacgccca atccggcag cattgaggcg    3360 ggtttttttc tttttttaaaa tccagggtgc ggctaaagga cccggtcgtc ctggcaatcc    3420
gtgtgtacct cccggtccgc agatctgctc caaacagaca acaacgggag gcagaggaaa    3480
agagagagat ctgcggaacg tcgtgtgagt acgaaccgga attgcgcagg acgacctggt    3540
cccttcttcg tggatagaac ccgcctcaat gcactggaga tttggggcgt ggcccgccgc    3600
aaagactccg gcttagccga gtagatggtt gggtcgcgga tgcgcgaaag gccttgtggt    3660
acctcgcgtt tttttttttt atttgttctt ccaa                               3694
```

<210> SEQ ID NO 16
<211> LENGTH: 3893
<212> TYPE: DNA
<213> ORGANISM: Artificial Sequence
<220> FEATURE:
<223> OTHER INFORMATION: Synthesized

<400> SEQUENCE: 16

```
cttgttgggt cgcgcaacag tgggcctgtg gtaactgagt tttgttcagg cctgcatagg     60
ttgtgctgcg agtctctctc gtgaagcaga gacagacggg aggcggagga aaagagacgc    120
cggatatgat ccgaagttgt tatctgcagc acctatcggc agtaccacag tgcctttcgc    180
gacccatagc actactcggc tagccagttc tgcggggca cgccaaatct caggcattga    240
gcgggttatc cacgaagacg gaacccggcg tctggcaatc ggtgctactc cggttcgcag    300
catcttctca cacaaacaac gggggagaca ggaaagagag aaagatcaat gcgaaccggt    360
```

| | | | | |
|---|---|---|---|---|
| gagtcacacc | aggattcgcc | aggcgtaccg | ggtcccttc | gtggataaac | ccagctcaat | 420 |
| gcctggagat | tttggcgtgc | caccgccaga | cctgctcagc | cgagtatgtt | gggtcggaaa | 480 |
| ggccattgtg | gtactagcct | gataggggtg | ctgtgcgaga | tctctcttca | acacacaacg | 540 |
| cagcgagaac | ggttaaggta | aacgagagt | tctcggaagc | acccatcgg | gggcaagtcc | 600 |
| acaggaggcc | cttttcgcga | ccccatgaca | ctactcgggg | gggtcttcgc | agtcttagcc | 660 |
| gggggccgcc | caaatctctc | aggcatttgg | gcgggttttt | tttatccacg | aatgacctgg | 720 |
| cgggcggtcg | tctggcaatg | tcggtggtac | tacaccgttt | ctcgcagagt | ctctctccaa | 780 |
| catccacaca | agcggaggag | gaggaaaaga | gaagagatct | ggcggagccc | ggtggtactc | 840 |
| ggaattgcca | ggacgaccgg | ggtctttcgt | gataaaccgc | tcaatgcctg | gaaatttggg | 900 |
| cgtgcccccg | caagactgct | agccgagtag | tgttggcggt | cgcgaatggc | ttgtgtactg | 960 |
| gcctgaatag | ggttgcttgc | ggacgatctt | cgtctcgaaa | caacaacaaa | cggaggaggg | 1020 |
| agggaaaaga | gagagatcgt | cgcagcaccc | tatcagccgc | agctaccaca | agcctttcgc | 1080 |
| gacgggcaac | gactactttg | cggggagcag | tcgttgcggg | ccacgccaat | ctcgcccagg | 1140 |
| catattcgag | gcgggtttta | tcccgcggag | ggagcccggt | cggtctggca | attcggtgta | 1200 |
| ctcgcacggt | ttcgcagatc | tccttctcaa | gcaacagggg | gggggaaca | gaggggagg | 1260 |
| gaggcaggac | caagaggagg | atgatcctgc | ggaaaccggt | gagtacagcc | gggacattgc | 1320 |
| ccaggacgac | cgcgcagccg | gccgcaccgc | cccccggtg | cggtccttct | cgtggccgca | 1380 |
| gacgccccgc | ccaccggcgc | ccgtcagtcc | gcccgtgccg | gagaagtatt | gggatgggcg | 1440 |
| tgccgcccgc | aagacgtgct | cacgccgaag | tagttgtgtt | ggtggcgctg | gagggtactt | 1500 |
| gtcggcgaaa | ggcgctttcg | ggtagctgcc | tgataggccg | tgcttggaga | tctcctctca | 1560 |
| acaacaacaa | cggaggccac | ggaggcaaag | agagctagat | gctcgcagcg | actatcccgg | 1620 |
| cgcaagggcc | tcatgtatgg | agccgaacac | tcagctcggg | ccgctaaggc | ggctctggcg | 1680 |
| gggccgacgc | ctcgcgcgcg | ctcgaggctc | gggtttatcc | gcaccgacgg | tacgccggtc | 1740 |
| gtcctggcat | cggtgtcacc | tcaccgttcc | gcagatctct | cgctgccgac | caagcaagcc | 1800 |
| aaccggggag | gccggggaaa | agatgatcga | gatcgtgcgg | acgcctggtg | acgtacaccg | 1860 |
| gattgccagg | gactacgacc | tcccttccc | gggctcctct | tcgtggtatc | aagaccagca | 1920 |
| acgaaaccag | agcgctcaca | tggcctggac | gggtttgcgc | gtgtccggca | agactgctag | 1980 |
| gcgcgagata | ggtgttgggc | gtgcgcgaag | gaaaccttag | tggtactaag | aagcctgata | 2040 |
| gggcgtgcct | tagcgagatc | tctcgtcac | agagattta | cttcgcccac | cacaaacaac | 2100 |
| cggaagaagg | acggccaaca | gagacgagat | cctctcgcaa | gcacccctat | caggcagtat | 2160 |
| agcgcacaag | gcctttcgcg | acccagcact | actcggtcg | ctcggcagag | tctttggggc | 2220 |
| gcgccaaatg | tgccaggcat | tggacggcgt | tatccccgaa | agggacacca | cggtcgtcct | 2280 |
| gcagaagcgt | gccggtgtca | ctgcaccggt | tccgcgcagt | ctctcttcgc | tcaacaagca | 2340 |
| gacaacggaa | gcggaggaaa | agagagtaga | tctggcaccg | ggtgagtact | acgcaatttt | 2400 |
| gcgccaggca | gcacgggtcc | cttcgtggat | agaacccggc | tcatgcctgg | gactttgggc | 2460 |
| gtcggccccc | gcaagactgc | tagcccgag | tagtgttggg | tcgcgaaaat | ggccttgtgg | 2520 |
| tactactcgc | cttaggagta | cgcttgtgag | atcttctctc | gcaacaaacc | acgacggagg | 2580 |
| cgggaggaaa | agagagagaa | tcggtcgcaa | agcccacta | catcaggcag | taccctacaa | 2640 |
| gggcctttcg | cgactccaac | actacttcgg | ctctacgtca | gtcttgcgcg | ggggcagggc | 2700 |
| cgaatctcaa | gacattgacg | cggggttct | ccacggagga | cgagatccgt | tccttgtgca | 2760 |

| | |
|---|---|
| attccgtgta ctacagccgg tttcgcagat cctctcccaa caagcaacgc gaggcggcaa | 2820 |
| cggaacatga gagagatctg gcaccgtgag tgtacgcacg gaattgcagg cacgacgggt | 2880 |
| ctttcgtgga tagtcaaccc gctattgctg gagatttgtg cgttgcaccc agcaatgact | 2940 |
| gctagcggcc gacgtacgac gggggttagga aaaaggggtc gcgaaggcct ttgtggtaac | 3000 |
| taccggctga taggcgtgct tggcgagatc ctgctctcct ctcgcactaa caacagcggg | 3060 |
| gaggcctgga agaggagaat tcttcgccag ccgcccgatc cagacagcat agtactacac | 3120 |
| ccggtggctt cttcgcgccc acactactcg gctcgacgat cttgcggggc acgcccaaaa | 3180 |
| tcgtccgcag ggccttgagg cgggttatcc acgtaaaggc cacgaccggt cgtcctggcg | 3240 |
| acatatctcg gtgtactccg cgagttccgc tcgatctctt ctcgatatca ccaacgtgag | 3300 |
| gccaggcggc aaaaagagag agtctgcgaa cgcggctgac gatacaccgg attgcaggac | 3360 |
| gaccgggtct ttatccgtgg atagacaccc gccatgcctg gagatttggc gcgttgcccg | 3420 |
| caagactgct agcgagtagc tcgttgggcg tcggccgaac ggccttgtgg tactggctga | 3480 |
| taaggggtgc ttgcgacgat ctcttccttc acaacaacaa ccggaggagg aggaaaagag | 3540 |
| aggaaggatc tcgcagcacc cctacctcag gcaagtacca caaggctttc ggacccaacc | 3600 |
| tacctcgcta gcaggtcttg cgggggccac gccaaatctc cccaggcatt gagcaggcgt | 3660 |
| ttatccaacc gacaagcctc gcccgggcgg cgcccgcccg cccagcctgt ctcctcttct | 3720 |
| ctttctcttt cttctggcgc tcgcctcctc gtcggtcccc ggcgttccgg cccggcgtcc | 3780 |
| cctcatgtct cgccgcgcgc cccctcctc ctttgcctgc ccgctctcgc ccctgtttc | 3840 |
| cttccacgct ggctcgcgcg tgcgctgtca ctcccgccct cccggtccgc aga | 3893 |

<210> SEQ ID NO 17
<211> LENGTH: 1833
<212> TYPE: DNA
<213> ORGANISM: Artificial Sequence
<220> FEATURE:
<223> OTHER INFORMATION: Synthesized

<400> SEQUENCE: 17

| | |
|---|---|
| cccgcagact gctagccgag tagtgttggg tcgcgaaggg ccttgtggta ctctccgcct | 60 |
| gatgggggtgg cttgcgagaa cgcccccgcg ccaaaaaaac atgctctcct ccacaacaac | 120 |
| aacgaggag ggtgctgctt taggaaaaga gagagattcg cagccccacg cagccctagt | 180 |
| cccgcagcag cgtacccacc caccccagcg cctgttcgcc gaccgccaca ctaccggctt | 240 |
| agcaagtctt gcggggcacg cccaaatctc ccgggcattg agcgcgtttt actccaccgg | 300 |
| aaagaccaga cctcgggcgt ctgggcattc ggttgctaac tgcaccggtt ttccccgcag | 360 |
| atctttctc acacaaccac ggggcggagg aaaagagaga gatctggcgg tgaaccggct | 420 |
| tggtacaccc ggaattggcc cagggacgac cccgggtccc tttctcgtgg atagaacccg | 480 |
| cctccatgcc tggagatttg gcgtccccc cgccagactg ctagccgagg tagctgtttg | 540 |
| ggctccgcga agggctttgt ggtactgctg aatagggtgc ttgcgagatc tccgtctcca | 600 |
| acaacaacaa caacggagga ggaggaaaca tgaagagaga tccttcgcaa gcaccctag | 660 |
| tccagcggca gtaccaacaa ggcctttcgg cgacccaaca cgttactcgg ctagcagtcc | 720 |
| ttgcggggc acgcccaaat ctcccaggca tttgagccga cgcgcgtttt ttttatgccc | 780 |
| accgaaaggg gacccggccg tcctgtgcca aattccggt gtactgccac ccggttccgc | 840 |
| agattcgtct ctccaacaac aacaacggag gaggaaggga aaagagagag atctgcggac | 900 |

| | |
|---|---|
| ccggtgaagc tcaccggaaa ttgccaaaag gagacccggg tcctttttc gtttggataa | 960 |
| actccgctca tgcctggaga tttgggcgcg tgcccgcccc gcaagactgc ttaactagcc | 1020 |
| gagtagtgtt gggtcggcga aaggccttgg tggtaactgc ctgatagggt gggcgttggc | 1080 |
| gagatctcct ttcaacaaca acaacggag ggaggaggaa aagagagaga tctcgcaagc | 1140 |
| aagccctatc aggcgtacca cacggccttt tcgcggaacc aaacacctac tccggctagc | 1200 |
| aagcttcctg cgggggggcca cggccaatct ccagccattt gagcgggttt ttatcacacg | 1260 |
| aagacccggc cggtctggca atctccggtg tagctgcaac gcggttccgc agatctcttg | 1320 |
| ctcaacaaca acaacggagg aggcaaagga aacagagaga gatctgcgga accggtgagt | 1380 |
| caccggaaat ttgcccagga cgacacgggt cctttcgtgg ataacaccgc caatgccgtg | 1440 |
| ggagatttgg gcgtgccccg caagaaactc tgcctagccg agtacgtgtt tgggtccggc | 1500 |
| gaaagggcct tgtggtaatt cgcctgatag ggtgcttggc ggagcatctc tctcaacaac | 1560 |
| ggaaaaacgg aggaggaggg aaagagagga gatcctcgca aagcaccta tcaggcagtg | 1620 |
| acaacaaggc ctttcgcgac ctaacactac ttcggcgtta gcatctttgc cgggggcagg | 1680 |
| cccaaatctc atacaggcat tggaggcgcg ggttttatcc acccgaaaag acccgccggt | 1740 |
| ctggcggggc aattccggtg gtacttcaac ggtttcccgc caagaatttc tcctcaaaca | 1800 |
| acaacaacgg ggaggaggaa aagagagaga tcc | 1833 |

<210> SEQ ID NO 18
<211> LENGTH: 3527
<212> TYPE: DNA
<213> ORGANISM: Artificial Sequence
<220> FEATURE:
<223> OTHER INFORMATION: Synthesized

<400> SEQUENCE: 18

| | |
|---|---|
| cccgtctgag cccggcgttc ctatccacga ccccggaccc ccgcgcctcg tcccctgcgc | 60 |
| cgcaactgtc cggccctgct caaccctccg gttccggcca gatctcctct aacaacacca | 120 |
| acggaaggag gaggaaaaga gatgacgatc tgcggaaccg gttgagtaca ccggaattgc | 180 |
| caggacgacc gggtcctttc gtggataaac ccgctcatgc ccggagaatt tgggcggtgc | 240 |
| ccacgcaaga cctcgctccg attcagcgat agtcgttggg tcgcgaaagg cctttgtggt | 300 |
| actgcctgat aagggtgcct gcgagatctt ctcaaccagc acaagcggca gggaggcgag | 360 |
| gaaaagagag aagatctcgc acgcaccccc gcctatcagc gcagtaccac aaggcctttc | 420 |
| gcgaccaaca acctactcgg cccgcctagc agtcttgccg ggggcacgca aatctccagg | 480 |
| catgagcggg ttatccaccg acaggaccgt cgcgtcgtcc tggcaattcc ggtgtactgc | 540 |
| acaaggcttc cgcaggcatc tctctcaacc cacaccgcaa cgaggaggag gaaatacaga | 600 |
| gagagatctg cggaaccggt gagtacaccc ggattgcagg acaccgggtc ctttccgtgg | 660 |
| ataaccgtc gaatgccccg gagactttgg gcgtgccacg caagatgctc agcccgagta | 720 |
| gtgtctgggt cgcgaaaggc cttgtgtact gctgataggg tgcttgcgaa gatctctctc | 780 |
| aacaacaaca cggggagga ggaaagagat gagatctcgc aagcaacccc tatcagggca | 840 |
| ggtcaccaca agggcctcgt atcgcgaccc acactactcg gcctagcagt cttgcggggg | 900 |
| ggcacgccga aatctccagg catgtgagcg ggtttatccc gcgaaagggc cacgcggctc | 960 |
| gtgctggccg aattccggtg tacactcacc ggttccgcag atctcttctc catcagcaca | 1020 |
| acaacgagga ggaggaaaag agcaggaaga tctgcggaac cggtgaccgt acaccggatt | 1080 |
| gccaggacga ccagggtcct tctcgtggat atacccgctc aatgccctcg gagattttg | 1140 |

```
gccgtgccca cgcaagaatg ctagccgagt attgtttggg ttcgcgaaag gccttgtggt    1200
ctgcgcctga tagggtgctt gcgagtctct ctcaacaaca acaccggagg gaggacaaga    1260
gagagatctc gcaagcaccc tatgccaggg ccgtaccccc acggggcggg gcctggttcg    1320
cgagcccaaa cacctactcg gctaggcagg tcttgcgggg cacgcccaaa tctccaggca    1380
ttgagcgggt ttatcacgac aggacccgcg tcgtcctggc attccgtgtg tactccaacc    1440
ggtttcccgc agatctatct caacaacaca acggaggaag gtaaggaaca gaggagagat    1500
ctgaggagaa acgccgcgtg gagtacacgg attgccagga cggaccgggt cctttcgtgg    1560
ataaacccgc tcaaatccgg agatttgggg cgtcggccca ccgcagactg ctagccgagt    1620
actgttgggt cgcgaaaggc cttgtgggta ctgcctatag ggtggctgcc gagatcttct    1680
ctcaacacac acggagggca gcgaggaaaa gagagacagc tctcggaacg cccctattca    1740
ggggccaagg ccttcccgct cggcgacccc acactactcg gatagccagt cttgcggggc    1800
cacgcccaaa atctccagcc attcggagcg gtttaatcc acgaaaggac cccggtcgtc    1860
ctgcaattcc ggtgtactca ccggttccgc agattctctc tcaacaacaa caaccgagag    1920
gagggacgga aaagagagac gatctgcgga accggtgagg ctacagcccg gaattgccag    1980
gacgaccggt ccttctcgtg atacaacccg cctcaatgcc gaagaatttg ggcgttgccc    2040
acgcaacgac tcgctagccc gacgtagtgt tgggtccgac gaaaggcttg tttgcgtact    2100
gctgtagggt gctttgcgag atcttcgctc tcacaacaac aacggaggca ggaagggaaa    2160
agagagagtc ctcgcaagca ccgcctagtc aggcagtacc acaaggcctt tccgcgaccg    2220
caacaactat cgggccgcta gcagtcttgc ggggcacgcc caattctcca ggcttgagcg    2280
ggttttatca ccgaaggacc cggtcgtcct ggcaattccg gttgtacgct caccggtccg    2340
cagatctcct ctcacacaca caacggagga ggaggaaaga cgagagatct gcggaaccgg    2400
ggtgagtaca cggacattgc caggacgccg ggttctttcg tggataaacc gctcaatgcc    2460
cggagatttg ggcgtgcccc acgcaatgac tgctagccag tagtgttggg ctcgcgaaag    2520
gcccttgtgg gtactgcgcc tgataagggt gcttgcgaga tcttctcaac aacacaacga    2580
gaggagggaa aagagagaga tctcgcaagc acctatcagg cgtacacaac ggccttcaat    2640
cagaaaaaag acccagacac tactcggcta gacagtcttg cggggcacg ccccaaatct    2700 caggcattga acgggtttat ccacgaaagg accgcgtcg tccctggca atctcggtgt    2760 actccagcgg tttccgcaca gatcctctcc tcccacacgc caacaacaa caacgcgagg    2820 aggaggcgaa aagacgagag attctgcgaa ccggtgagta caccggaatt gccaggccgg    2880
accgggtcct ttcgtggcta aaccccgctc aatgccgcgg agatttgggg cgttcgccac    2940
gcacgactcg ctagccgagt agtgttgggc tccgccccgg aaaggccttg gtggctactg    3000
cctgataggg tgctgcgaga tctctctcaa gcaacaacaa cggaggacgg gaggaaaaga    3060
cgacgacgca tctcgccacg cagccctaat caggggggcag tcaccgggca aaggcgctt    3120 tcgcgcaccc catcacactc aatgcgcgcc tggagcagtc cacccgcttg ccgggaggcc    3180
tcggcacggc caaacgcgcc agatctcgca cggcatccgt ggagccgcgg tttactccca    3240
cgaagaggat cccccggtcgt gcgctggca attccggtgt acctcgcttg cagccccggct    3300 tccgcatgat ctcctctcca atcaacaaca acggaggagg gaggaaaaaa cgaggagcag    3360
atccgtggcg gacaacgccg gtgaggtaca acccgggaaa ttccgccgaa gcaaacggcg    3420
accggtctct tccccacgca acaccacgcg atcaatccaa acaaaaaaaa aaaaaaaaaa    3480
```
aaaaaacgtg gaaaccaaga ggaacaccac ccgcccccg ggcaccc            3527

<210> SEQ ID NO 19
<211> LENGTH: 5
<212> TYPE: DNA
<213> ORGANISM: Artificial Sequence
<220> FEATURE:
<223> OTHER INFORMATION: Synthesized

<400> SEQUENCE: 19 ctgcg            5

<210> SEQ ID NO 20
<211> LENGTH: 6
<212> TYPE: DNA
<213> ORGANISM: Artificial Sequence
<220> FEATURE:
<223> OTHER INFORMATION: Synthesized

<400> SEQUENCE: 20 ctggcg            6

<210> SEQ ID NO 21
<211> LENGTH: 6
<212> TYPE: DNA
<213> ORGANISM: Artificial Sequence
<220> FEATURE:
<223> OTHER INFORMATION: Synthesized

<400> SEQUENCE: 21 ctggca            6

<210> SEQ ID NO 22
<211> LENGTH: 4
<212> TYPE: DNA
<213> ORGANISM: Artificial Sequence
<220> FEATURE:
<223> OTHER INFORMATION: Synthesized

<400> SEQUENCE: 22 ctgc            4

<210> SEQ ID NO 23
<211> LENGTH: 6
<212> TYPE: DNA
<213> ORGANISM: Artificial Sequence
<220> FEATURE:
<223> OTHER INFORMATION: Synthesized

<400> SEQUENCE: 23 ctgcgg            6

<210> SEQ ID NO 24
<211> LENGTH: 7
<212> TYPE: DNA
<213> ORGANISM: Artificial Sequence
<220> FEATURE:
<223> OTHER INFORMATION: Synthesized

<400> SEQUENCE: 24 ctgcgga            7

<210> SEQ ID NO 25
<211> LENGTH: 8
<212> TYPE: DNA
<213> ORGANISM: Artificial Sequence -continued

```
<220> FEATURE:
<223> OTHER INFORMATION: Synthesized

<400> SEQUENCE: 25 ctgcggaa                                                                8

<210> SEQ ID NO 26
<211> LENGTH: 9
<212> TYPE: DNA
<213> ORGANISM: Artificial Sequence
<220> FEATURE:
<223> OTHER INFORMATION: Synthesized

<400> SEQUENCE: 26 ctgcggaac                                                               9

<210> SEQ ID NO 27
<211> LENGTH: 10
<212> TYPE: DNA
<213> ORGANISM: Artificial Sequence
<220> FEATURE:
<223> OTHER INFORMATION: Synthesized

<400> SEQUENCE: 27
ctgcggaacc                                                             10

<210> SEQ ID NO 28
<211> LENGTH: 11
<212> TYPE: DNA
<213> ORGANISM: Artificial Sequence
<220> FEATURE:
<223> OTHER INFORMATION: Synthesized

<400> SEQUENCE: 28
ctgcggaacc g                                                           11

<210> SEQ ID NO 29
<211> LENGTH: 12
<212> TYPE: DNA
<213> ORGANISM: Artificial Sequence
<220> FEATURE:
<223> OTHER INFORMATION: Synthesized

<400> SEQUENCE: 29
ctgcggaacc gg                                                          12

<210> SEQ ID NO 30
<211> LENGTH: 13
<212> TYPE: DNA
<213> ORGANISM: Artificial Sequence
<220> FEATURE:
<223> OTHER INFORMATION: Synthesized

<400> SEQUENCE: 30
ctgcggaacc ggt                                                         13

<210> SEQ ID NO 31
<211> LENGTH: 14
<212> TYPE: DNA
<213> ORGANISM: Artificial Sequence
<220> FEATURE:
<223> OTHER INFORMATION: Synthesized

<400> SEQUENCE: 31
ctgcggaacc ggtg                                                        14
```

<210> SEQ ID NO 32
<211> LENGTH: 15
<212> TYPE: DNA
<213> ORGANISM: Artificial Sequence
<220> FEATURE:
<223> OTHER INFORMATION: Synthesized

<400> SEQUENCE: 32
ctgcggaacc ggtga                                                    15

<210> SEQ ID NO 33
<211> LENGTH: 16
<212> TYPE: DNA
<213> ORGANISM: Artificial Sequence
<220> FEATURE:
<223> OTHER INFORMATION: Synthesized

<400> SEQUENCE: 33
ctgcggaacc ggtgag                                                   16

<210> SEQ ID NO 34
<211> LENGTH: 17
<212> TYPE: DNA
<213> ORGANISM: Artificial Sequence
<220> FEATURE:
<223> OTHER INFORMATION: Synthesized

<400> SEQUENCE: 34
ctgcggaacc ggtgagt                                                  17

<210> SEQ ID NO 35
<211> LENGTH: 18
<212> TYPE: DNA
<213> ORGANISM: Artificial Sequence
<220> FEATURE:
<223> OTHER INFORMATION: Synthesized

<400> SEQUENCE: 35
ctgcggaacc ggtgagta                                                 18

<210> SEQ ID NO 36
<211> LENGTH: 19
<212> TYPE: DNA
<213> ORGANISM: Artificial Sequence
<220> FEATURE:
<223> OTHER INFORMATION: Synthesized

<400> SEQUENCE: 36
ctgcggaacc ggtgagtac                                                19

<210> SEQ ID NO 37
<211> LENGTH: 20
<212> TYPE: DNA
<213> ORGANISM: Artificial Sequence
<220> FEATURE:
<223> OTHER INFORMATION: Synthesized

<400> SEQUENCE: 37
ctgcggaacc ggtgagtaca                                               20

<210> SEQ ID NO 38
<211> LENGTH: 21
<212> TYPE: DNA
<213> ORGANISM: Artificial Sequence
<220> FEATURE:
<223> OTHER INFORMATION: Synthesized

```
<400> SEQUENCE: 38
ctgcggaacc ggtgagtaca c                                              21

<210> SEQ ID NO 39
<211> LENGTH: 22
<212> TYPE: DNA
<213> ORGANISM: Artificial Sequence
<220> FEATURE:
<223> OTHER INFORMATION: Synthesized

<400> SEQUENCE: 39
ctgcggaacc ggtgagtaca cc                                             22

<210> SEQ ID NO 40
<211> LENGTH: 23
<212> TYPE: DNA
<213> ORGANISM: Artificial Sequence
<220> FEATURE:
<223> OTHER INFORMATION: Synthesized

<400> SEQUENCE: 40
ctgcggaacc ggtgagtaca ccg                                            23

<210> SEQ ID NO 41
<211> LENGTH: 24
<212> TYPE: DNA
<213> ORGANISM: Artificial Sequence
<220> FEATURE:
<223> OTHER INFORMATION: Synthesized

<400> SEQUENCE: 41
ctgcggaacc ggtgagtaca ccgg                                           24

<210> SEQ ID NO 42
<211> LENGTH: 25
<212> TYPE: DNA
<213> ORGANISM: Artificial Sequence
<220> FEATURE:
<223> OTHER INFORMATION: Synthesized

<400> SEQUENCE: 42
ctgcggaacc ggtgagtaca ccgga                                          25

<210> SEQ ID NO 43
<211> LENGTH: 26
<212> TYPE: DNA
<213> ORGANISM: Artificial Sequence
<220> FEATURE:
<223> OTHER INFORMATION: Synthesized

<400> SEQUENCE: 43
ctgcggaacc ggtgagtaca ccggaa                                         26

<210> SEQ ID NO 44
<211> LENGTH: 27
<212> TYPE: DNA
<213> ORGANISM: Artificial Sequence
<220> FEATURE:
<223> OTHER INFORMATION: Synthesized

<400> SEQUENCE: 44
ctgcggaacc ggtgagtaca ccggaat                                        27

<210> SEQ ID NO 45
```

```
<211> LENGTH: 28
<212> TYPE: DNA
<213> ORGANISM: Artificial Sequence
<220> FEATURE:
<223> OTHER INFORMATION: Synthesized

<400> SEQUENCE: 45
ctgcggaacc ggtgagtaca ccggaatt                                          28

<210> SEQ ID NO 46
<211> LENGTH: 29
<212> TYPE: DNA
<213> ORGANISM: Artificial Sequence
<220> FEATURE:
<223> OTHER INFORMATION: Synthesized

<400> SEQUENCE: 46
ctgcggaacc ggtgagtaca ccggaattg                                         29

<210> SEQ ID NO 47
<211> LENGTH: 30
<212> TYPE: DNA
<213> ORGANISM: Artificial Sequence
<220> FEATURE:
<223> OTHER INFORMATION: Synthesized

<400> SEQUENCE: 47
ctgcggaacc ggtgagtaca ccggaattgc                                        30

<210> SEQ ID NO 48
<211> LENGTH: 4
<212> TYPE: DNA
<213> ORGANISM: Artificial Sequence
<220> FEATURE:
<223> OTHER INFORMATION: Synthesized

<400> SEQUENCE: 48 ctcg                                                                     4

<210> SEQ ID NO 49
<211> LENGTH: 5
<212> TYPE: DNA
<213> ORGANISM: Artificial Sequence
<220> FEATURE:
<223> OTHER INFORMATION: Synthesized

<400> SEQUENCE: 49 ctcgc                                                                    5

<210> SEQ ID NO 50
<211> LENGTH: 6
<212> TYPE: DNA
<213> ORGANISM: Artificial Sequence
<220> FEATURE:
<223> OTHER INFORMATION: Synthesized

<400> SEQUENCE: 50 ctcgca                                                                   6

<210> SEQ ID NO 51
<211> LENGTH: 7
<212> TYPE: DNA
<213> ORGANISM: Artificial Sequence
<220> FEATURE:
<223> OTHER INFORMATION: Synthesized

<400> SEQUENCE: 51
```

```
ctcgcaa                                                           7

<210> SEQ ID NO 52
<211> LENGTH: 8
<212> TYPE: DNA
<213> ORGANISM: Artificial Sequence
<220> FEATURE:
<223> OTHER INFORMATION: Synthesized

<400> SEQUENCE: 52 ctcgcaag                                                          8

<210> SEQ ID NO 53
<211> LENGTH: 9
<212> TYPE: DNA
<213> ORGANISM: Artificial Sequence
<220> FEATURE:
<223> OTHER INFORMATION: Synthesized

<400> SEQUENCE: 53 ctcgcaagc                                                         9

<210> SEQ ID NO 54
<211> LENGTH: 10
<212> TYPE: DNA
<213> ORGANISM: Artificial Sequence
<220> FEATURE:
<223> OTHER INFORMATION: Synthesized

<400> SEQUENCE: 54
ctcgcaagca                                                       10

<210> SEQ ID NO 55
<211> LENGTH: 11
<212> TYPE: DNA
<213> ORGANISM: Artificial Sequence
<220> FEATURE:
<223> OTHER INFORMATION: Synthesized

<400> SEQUENCE: 55
ctcgcaagca c                                                     11

<210> SEQ ID NO 56
<211> LENGTH: 12
<212> TYPE: DNA
<213> ORGANISM: Artificial Sequence
<220> FEATURE:
<223> OTHER INFORMATION: Synthesized

<400> SEQUENCE: 56
ctcgcaagca cc                                                    12

<210> SEQ ID NO 57
<211> LENGTH: 13
<212> TYPE: DNA
<213> ORGANISM: Artificial Sequence
<220> FEATURE:
<223> OTHER INFORMATION: Synthesized

<400> SEQUENCE: 57
ctcgcaagca ccc                                                   13

<210> SEQ ID NO 58
<211> LENGTH: 14
<212> TYPE: DNA
```

```
<213> ORGANISM: Artificial Sequence
<220> FEATURE:
<223> OTHER INFORMATION: Synthesized

<400> SEQUENCE: 58
ctcgcaagca ccct                                                         14

<210> SEQ ID NO 59
<211> LENGTH: 15
<212> TYPE: DNA
<213> ORGANISM: Artificial Sequence
<220> FEATURE:
<223> OTHER INFORMATION: Synthesized

<400> SEQUENCE: 59
ctcgcaagca cccta                                                        15

<210> SEQ ID NO 60
<211> LENGTH: 16
<212> TYPE: DNA
<213> ORGANISM: Artificial Sequence
<220> FEATURE:
<223> OTHER INFORMATION: Synthesized

<400> SEQUENCE: 60
ctcgcaagca ccctat                                                       16

<210> SEQ ID NO 61
<211> LENGTH: 17
<212> TYPE: DNA
<213> ORGANISM: Artificial Sequence
<220> FEATURE:
<223> OTHER INFORMATION: Synthesized

<400> SEQUENCE: 61
ctcgcaagca ccctatc                                                      17

<210> SEQ ID NO 62
<211> LENGTH: 18
<212> TYPE: DNA
<213> ORGANISM: Artificial Sequence
<220> FEATURE:
<223> OTHER INFORMATION: Synthesized

<400> SEQUENCE: 62
ctcgcaagca ccctatca                                                     18

<210> SEQ ID NO 63
<211> LENGTH: 19
<212> TYPE: DNA
<213> ORGANISM: Artificial Sequence
<220> FEATURE:
<223> OTHER INFORMATION: Synthesized

<400> SEQUENCE: 63
ctcgcaagca ccctatcag                                                    19

<210> SEQ ID NO 64
<211> LENGTH: 20
<212> TYPE: DNA
<213> ORGANISM: Artificial Sequence
<220> FEATURE:
<223> OTHER INFORMATION: Synthesized

<400> SEQUENCE: 64
ctcgcaagca ccctatcagg                                                   20
```

<210> SEQ ID NO 65
<211> LENGTH: 21
<212> TYPE: DNA
<213> ORGANISM: Artificial Sequence
<220> FEATURE:
<223> OTHER INFORMATION: Synthesized

<400> SEQUENCE: 65
ctcgcaagca ccctatcagg c                                              21

<210> SEQ ID NO 66
<211> LENGTH: 22
<212> TYPE: DNA
<213> ORGANISM: Artificial Sequence
<220> FEATURE:
<223> OTHER INFORMATION: Synthesized

<400> SEQUENCE: 66
ctcgcaagca ccctatcagg ca                                             22

<210> SEQ ID NO 67
<211> LENGTH: 23
<212> TYPE: DNA
<213> ORGANISM: Artificial Sequence
<220> FEATURE:
<223> OTHER INFORMATION: Synthesized

<400> SEQUENCE: 67
ctcgcaagca ccctatcagg cag                                            23

<210> SEQ ID NO 68
<211> LENGTH: 24
<212> TYPE: DNA
<213> ORGANISM: Artificial Sequence
<220> FEATURE:
<223> OTHER INFORMATION: Synthesized

<400> SEQUENCE: 68
ctcgcaagca ccctatcagg cagt                                           24

<210> SEQ ID NO 69
<211> LENGTH: 25
<212> TYPE: DNA
<213> ORGANISM: Artificial Sequence
<220> FEATURE:
<223> OTHER INFORMATION: Synthesized

<400> SEQUENCE: 69
ctcgcaagca ccctatcagg cagta                                          25

<210> SEQ ID NO 70
<211> LENGTH: 26
<212> TYPE: DNA
<213> ORGANISM: Artificial Sequence
<220> FEATURE:
<223> OTHER INFORMATION: Synthesized

<400> SEQUENCE: 70
ctcgcaagca ccctatcagg cagtac                                         26

<210> SEQ ID NO 71
<211> LENGTH: 27
<212> TYPE: DNA
<213> ORGANISM: Artificial Sequence
<220> FEATURE:

```
<223> OTHER INFORMATION: Synthesized

<400> SEQUENCE: 71
ctcgcaagca ccctatcagg cagtacc                                      27

<210> SEQ ID NO 72
<211> LENGTH: 28
<212> TYPE: DNA
<213> ORGANISM: Artificial Sequence
<220> FEATURE:
<223> OTHER INFORMATION: Synthesized

<400> SEQUENCE: 72
ctcgcaagca ccctatcagg cagtacca                                     28

<210> SEQ ID NO 73
<211> LENGTH: 29
<212> TYPE: DNA
<213> ORGANISM: Artificial Sequence
<220> FEATURE:
<223> OTHER INFORMATION: Synthesized

<400> SEQUENCE: 73
ctcgcaagca ccctatcagg cagtaccac                                    29

<210> SEQ ID NO 74
<211> LENGTH: 30
<212> TYPE: DNA
<213> ORGANISM: Artificial Sequence
<220> FEATURE:
<223> OTHER INFORMATION: Synthesized

<400> SEQUENCE: 74
ctcgcaagca ccctatcagg cagtaccaca                                   30
```